(12) United States Patent
Wen et al.

(10) Patent No.: US 10,292,991 B2
(45) Date of Patent: May 21, 2019

(54) SMALL MOLECULE THERAPEUTIC COMPOUNDS THAT REDUCE THE INCIDENCE OF INTRACEREBRAL HEMORRHAGE AND BRAIN MICROHEMORRHAGES

(71) Applicant: St. Michaels Hospital, Toronto (CA)

(72) Inventors: Xiao-Yan Wen, Toronto (CA); R. Loch Macdonald, Scottsdale, AZ (US); Andrew Baker, Toronto (CA); Tom A. Schweizer, Oakville (CA)

(73) Assignee: Unity Health Toronto, Toronto (CA)

( * ) Notice: Subject to any disclaimer, the term of this patent is extended or adjusted under 35 U.S.C. 154(b) by 0 days.

(21) Appl. No.: 15/667,423

(22) Filed: Aug. 2, 2017

(65) Prior Publication Data
US 2018/0064731 A1  Mar. 8, 2018

Related U.S. Application Data

(60) Provisional application No. 62/370,077, filed on Aug. 2, 2016.

(51) Int. Cl.
| | | |
|---|---|---|
| *A61K 31/585* | (2006.01) | |
| *A61K 31/357* | (2006.01) | |
| *A61P 9/14* | (2006.01) | |
| *A61K 31/58* | (2006.01) | |
| *A61K 31/366* | (2006.01) | |
| *A61K 31/4422* | (2006.01) | |
| *A61K 31/4545* | (2006.01) | |
| *A61K 31/567* | (2006.01) | |
| *A61P 9/00* | (2006.01) | |
| *C07J 1/00* | (2006.01) | |
| *C07J 73/00* | (2006.01) | |

(52) U.S. Cl.
CPC .......... *A61K 31/585* (2013.01); *A61K 31/357* (2013.01); *A61K 31/366* (2013.01); *A61K 31/4422* (2013.01); *A61K 31/4545* (2013.01); *A61K 31/567* (2013.01); *A61K 31/58* (2013.01); *A61P 9/00* (2018.01); *A61P 9/14* (2018.01); *C07J 1/0096* (2013.01); *C07J 73/003* (2013.01)

(58) Field of Classification Search
None
See application file for complete search history.

(56) References Cited

U.S. PATENT DOCUMENTS

2011/0077258 A1* 3/2011 Carvalho ............. A61K 9/0004
514/269

FOREIGN PATENT DOCUMENTS

WO     2012/168450 A1   12/2012
WO  WO 2012/168450   * 12/2012

OTHER PUBLICATIONS

Li et al. (Stroke, 2010, 41[suppl 1]:S02-S94).*
Aguilar, et al; "Update in Intracerebral Hemorrhage", The Neurohospitalist, 1(3), 148-159, Jul. 2011.
Alharbi BM, et al. (2016) Animal models of spontaneous intracerebral hemorrhage. Neurol Res 38:448-455.
Altschul, S.F., et al., "Gapped BLAST and PSI-BLAST: a new generation of protein database search programs", (1997) Nucleic Acids Res. 25:3389-3402.
Auer, RN, Sutherland, GR (2005) "Primary intracerebral hemorrhage: pathophysiology," Can. J.Neurol. Sci. 32 Suppl. 2: 3-12 (abstract).
Avdesh A, et al. Regular care and maintenance of a zebrafish (*Danio rerio*) laboratory: an introduction. J Vis Exp 2012;e4196.
Barker FG, et al (2001) "Temporal clustering of hemorrhages from untreated cavernous malformations of the central nervous system," Neurosurgery 49:15-24.
Benjamin, Le et al. (1999) "Selective ablation of immature blood vessels in established human tumors follows vascular endothelial growth factor withdrawal." J Clin Invest 103: 159-165.
Boesiger J, et al (1998) Mast cells can secrete vascular permeability factor/vascular endothelial cell growth factor and exhibit enhanced release after immunoglobulin E-dependent upregulation of fc epsilon receptor I expression. J Exp Med 188:1135-1145.
Bridges E, et al (2011) "Notch regulation of tumor angiogenesis." Future Oncol. 7:569-588.
Broman, MT et al (2006) "Cdc42 regulates adherens junction stability and endothelial permeability by inducing alpha-catenin interaction with the vascular endothelial cadherin complex," Cir. Res. 98: 73-80.
Brooks, PC et al, "Requirement of vascular integrin alpha v beta 3 for angiogenesis," Science (1994) vol. 264, Issue 5158, pp. 569-571.
Brooks, PC et al, "Integrin ?v?3 antagonists promote tumor regression by inducing apoptosis of angiogenic blood vessels," (1994) Cell 79(7): 1157-64.
Brown LF, et al (1992) Expression of vascular permeability factor (vascular endothelial growth factor) by epidermal keratinocytes during wound healing. J Exp Med 176:1375-1379.
Brown LF, et al (1997) Vascular permeability factor/vascular endothelial growth factor: a multifunctional angiogenic cytokine. Exs 79:233-269.
Buchner DA, et al (2007) "pak2a mutations cause cerebral hemorrhage in redhead zebrafish," Proc Natl Acad Sci USA 104:13996-14001.
Butler MG, et al (2011) "Zebrafish as a model for hemorrhagic stroke," Methods Cell Biol 105:137-161.
Carmeliet P, Jain RK. (2011) Molecular mechanisms and clinical applications of angiogenesis. Nature. 473:298-307.
Carmeliet P. (2005) Angiogenesis in life, disease and medicine. Nature. 438:932-936.

(Continued)

*Primary Examiner* — Bong-Sook Baek
(74) *Attorney, Agent, or Firm* — McCarter & English, LLP; Beverly W. Lubit

(57) ABSTRACT

The described invention relates to small molecule therapeutic compounds capable of reducing the incidence of intracerebral hemorrhage and brain microhemorrhages identified using zebrafish and mouse models of intracerebral hemorrhage and brain microhemorrhages.

8 Claims, 16 Drawing Sheets
(12 of 16 Drawing Sheet(s) Filed in Color)
Specification includes a Sequence Listing.

(56) References Cited

OTHER PUBLICATIONS

Carmeliet P., et al (1999) "Targeted deficiency or cytosolic truncation of the VE-cadherin gene in mice impairs VEGF-mediated endothelial survival and angiogenesis," Cell 98:147-157.
Chan AC, et al (2010) "Recent insights into cerebral cavernous malformations: animal models of CCM and the human phenotype," FEBS J 277:1076-1083.
Chang SH et al. (2009) "VEGF-A induces angiogenesis by perturbing the cathepsin-cysteine protease inhibitor balance in venules, causing basement membrane degradation and mother vessel formation," Cancer Res 69: 4537-4544.
Chen, P. et al., "Animal model of fetal and neonatal immune thrombocytopenia: role of neonatal Fc receptor in the pathogenesis and therapy," Blood (2010) 116 (18): 3660-68.
Chrzanowska-Wodnicka M (2013) "Distinct functions for Rap1 signaling in vascular morphogenesis and dysfunction," Exp Cell Res 319:2350-2359.
Claverie, JM, et al, "Information Enhancement Methods for Large Scale Sequence Analysis", (1993) Comput. Chem., 17:191-201.
Collins R, et al, (2004) "Effects of cholesterol-lowering with simvastatin on stroke and other major vascular events in 20536 people with cerebrovascular disease or other high-risk conditions," Lancet 363:757-767.
Cordonnier C, et al (2010) "Radiological investigation of spontaneous intracerebral hemorrhage: systematic review and trinational survey," Stroke 41:685-690.
Corey, D.R. and J.M. Abrams (2001) "Morpholino antisense oligonucleotides: tools for investigating vertebrate development," Genome Biol. 2(5): 1015.1-1015.3.
Corpet, F., "Multiple sequence alignment with hierarchical clustering", (1988) Nucleic Acids Research 16:10881-90.
Coultas L, et al (2005) "Endothelial cells and VEGF in vascular development." Nature. 438:937-945.
D'Abbondanza JA, et al. Robust effects of genetic background on responses to subarachnoid hemorrhage in mice. J Cereb Blood Flow Metab 2016;36:1942-1954.
Dai, et al; "The novel ETA receptor antagonist HJP-272 prevents cerebral microvascular hemmorage in cerebral malaria and synergistically improves survival in combination with an artemisinin derivative".; Life Sciences. 91, 687-692, Oct. 15, 2012.
Dejana E (2004) Endothelial cell-cell junctions: happy together. Nat Rev Mol Cell Biol 5:261-270.
Dewhirst MW, et al. (2008) "Cycling hypoxia and free radicals regulate angiogenesis and radiotherapy response." Nat Rev Cancer. 8:425-437.
Di Q, et al, "Impaired cross-activation of ?3 integrin and VEGFR-2 on endothelial progenitor cells with aging decrases angiogenesis in response to hypoxia," Intl J. Cardiol. (2013) 168(3): 2167-76.
Diehl AM. (2012) "Neighborhood watch orchestrates liver regeneration." Nat Med. 18:497-499.
Dvorak AM, et al (1996) The vesiculo-vacuolar organelle (VVO): a distinct endothelial cell structure that provides a transcellular pathway for macromolecular extravasation. J Leukoc Biol 59:100-115.
Dvorak HF (2003) Rous-Whipple award lecture. How tumors make bad blood vessels and stroma. Am J Pathol 162:1747-1757.
Dvorak HF, et al (1979) Fibrin gel investment associated with line 1 and line 10 solid tumor growth, angiogenesis, and fibroplasia in guinea pigs. Role of cellular immunity, myofibroblasts, microvascular damage, and infarction in line 1 tumor regression. J Natl Cancer Inst 62:1459-1472.
Dvorak HF, et al (1979) Induction of a fibrin-gel investment: an early event in line 10 hepatocarcinoma growth mediated by tumor-secreted products. J Immunol 122:166-174.
Dvorak HF, et al (1981) Tumor shedding and coagulation. Science 212:923-924.

Eisa-Beygi S, et al (2013) "The 3-hydroxy-3-methylglutaryl-CoA reductase (HMGCR) pathway regulates developmental cerebral-vascular stability via prenylation-dependent signaling pathway," Dev Biol 373:258-266.
Eisa-Beygi S, et al. (2014) "A Call for Rigorous Study of Statins in Resolution of Cerebral Cavernous Malformation Pathology." Stroke 45(6):1859-61.
Fagiani E, Christofori G. (2013) "Angiopoietins in angiogenesis." Cancer Lett. 328:18-26.
Feng D, et al (1996) Vesiculo-vacuolar organelles and the regulation of venule permeability to macromolecules by vascular permeability factor, histamine, and serotonin. J Exp Med 183:1981-1986.
Feng D, et al (1997) Reinterpretation of endothelial cell gaps induced by vasoactive mediators in guinea-pig, mouse and rat: many are transcellular pores. J Physiol 504 (Pt 3):747-761.
Feng D, et al (1999) Pathways of macromolecular extravasation across microvascular endothelium in response to VPF/VEGF and other vasoactive mediators. Microcirculation 6:23-44.
Feng D, et al (2000) Different pathways of macromolecule extravasation from hyperpermeable tumor vessels. Microvascular Research 59:24-37.
Ferrara N, Kerbel RS. (2005) Angiogenesis as a therapeutic target. Nature. 438:967-974.
Finney, et al; "S1P is Associated with Protection in Human and Experimental Cerebral Malaria", Molecular Medicine, 17, 717-725, May 5, 2011.
Fisher M, et al. Therapeutic modulation of cerebral microhemorrhage in a mouse model of cerebral amyloid angiopathy. Stroke. 2011;42(11):3300-3.
Nagy JA, et al (2006) Permeability properties of tumor surrogate blood vessels induced by VEGF-A. Lab Invest 86:767-780.
Nagy, J.A.,et al., (2008) "Vascular permeability, vascular hyperpermeability and angiogenesis," Angiogenesis 11(2): 109-119.
Needleman, S., et al, "A General Method Applicable to the Search for Similarities in the Amino Acid Sequence of Two Proteins", (1970), J. Mol. Biol. 48:443.
Ni H, et al, "A novel murine model of fetal and neonatal alloimmune thrombocytopenia: respons to intravenous IgG therapy," Blood (2006) 107(7): 2976-83.
Nicosia, RF and Madri, JA (1987) "The microvascular extracellular matrix. Developmental changes during angiogenesis in the aortic ring-plasma clot model." Am J Pathol 128: 78-90.
Nieswandt, B. et al, "Targeting of platelet integrin ?IIb?3 determines systemic reaction and bleeding in murine thrombocytopenia regulated by activating and inhibitory Fc?R," Intl Immunol. (2003) 15(3): 341-49.
Nieswandt, B. et al., "Identification of critical antigen-specific mechanisms in the development of immune thrombocytopenic purpura in mice," Blood (2000) 96(7): 2520-27.
Oh P, et al (2007) Live dynamic imaging of caveolae pumping targeted antibody rapidly and specifically across endothelium in the lung. Nat Biotechnol 25:327-337.
Olsson AK, et al (2006) "VEGF receptor signaling-in control of vascular function." Nat Rev Mol Cell Biol. 7:359-371.
PCT/IB2017/001100 International Search Reoprt and Written Opinion, dated Jan. 4, 2018, 15 pages.
Pearson, W. R., et al, "Improved tools for biological sequence comparison", (1988), Proc. Natl. Acad. Sci. 85:2444-2448.
Pearson, W.R., et al., Using the FASTA Program to Search Protein and DNA Sequence Databases, (1994) Methods in Molecular Biology 24:307-331 (Abstract).
Peterson RT, Fishman MC (2011) "Designing zebrafish chemical screens," Methods Cell Biol 105:525-541.
Peterson YK, et al (2006) "A novel protein geranylgeranyltransferase-I inhibitor with high potency, selectivity, and cellular activity," J Biol Chem 281:12445-12450.
Pettersson A, et al (2000) Heterogeneity of the angiogenic response induced in different normal adult tissues by vascular permeability factor/vascular endothelial growth factor. Lab Invest 80:99-115.
Presta M, et al. (2005) "Fibroblast growth factor/fibroblast growth factor receptor system in angiogenesis." Cytokine Growth Factor Rev. 16:159-178.

(56) References Cited

OTHER PUBLICATIONS

Radu M, et al (2014) "PAK signalling during the development and progression of cancer," Nat Rev Cancer 14:13-25.
Ramchandran, R. et al (2008) "Critical role of Cdc42 in mediating endothelial barrier protection in vivo," Am. J. Physiol. Lung Cell Mol. Physiol. 295: 363-69.
Ren G, et al (2002) Morphological characteristics of the microvasculature in healing myocardial infarcts. J Histochem Cytochem 50:71-79.
Richardson BT, et al (2013) "Cerebral cavernous malformation is a vascular disease associated with activated RhoA signaling," Biol Chem 394:35-42.
Rivkin E, et al. (2013) "The linear ubiquitin-specific deubiquitinase gumby regulates angiogenesis." Nature 498:318-324.
Robinson, SD, et al, "?v?3 integrin limits the contribution of neuropilin-1 to vascular endothelial growth factor-induced angiogenesis," J. Biol. Chem. (2009) 284(49): 33966-81.
Roger VL, et al (2011) "Heart disease and stroke statistics—2011 update: a report from the American Heart Association," Circulation 123:e18-e209.
Rowe, RG and Weiss, SJ (2008) "Breaching the basement membrane: Who, when and how?" Trends Cell Biol 18: 560-574.
Sabri M, et al Dissociation of vasospasm and secondary effects of experimental subarachnoid hemorrhage by clazosentan. Stroke 2011;42:1454-1460.
Sabri M, et al. Anterior circulation mouse model of subarachnoid hemorrhage. Brain Res 2009;1295:179-185.
Sabri M, et al. Simvastatin re-couples dysfunctional endothelial nitric oxide synthase in experimental subarachnoid hemorrhage. PLoS One 2011;6:e17062.
Sabri M, et al., Genetic elimination of eNOS reduces secondary complications of experimental subarachnoid hemorrhage. J Cereb Blood Flow Metab 2013;33:1008-1014.
Sabri M, et al., Mechanisms of microthrombi formation after experimental subarachnoid hemorrhage. Neuroscience 2012;224:26-37.
Sabri M, et al., Neuronal and astrocytic apoptosis after subarachnoid hemorrhage: a possible cause for poor prognosis. Brain Res 2008;1238:163-171.
Senger, DR (1996) "Cell migration promoted by a potent GRGDS-containing thrombin-cleavage fragment of osteopontin." Biochim Biophys Acta 1314: 13-24.
Senger, DR, and David, GE, (2011) "Angiogenesis," Cold Spring Haiti Perspect. Biol. Aug. 3(8): a005090.
Smith and Waterman, "Comparison of Biosequences", (1981), Adv. Appl. Math. 2:482-489.
Smith MCP, et al, (2010) "Mechanisms of vascular stability and the relationship to human disease," Curr. Opin. Hematol. 17(30: 237-44).
Soldi, R. et al, "Role of ?v?3 integrin in the activation of vascular endothelial growth factor receptor-2," EMBO J. (1999)18(4): 882-92.
Spindler, V. et al (2010) "Role of GTPases in control of microvascular permeability," Cardiovasc. Res. 87(2): 243-53.
Stan, RV, et al, (2004), "PV1 is a key structural component for the formation of the stomatal and fenestral diaphragms," Mol. Biol. Cell 15(8): 3615-30.
Stratman, AN et al. (2009) "Pericyte recruitment during vasculogenic tube assembly stimulates endothelial basement membrane matrix formation." Blood 114: 5091-5101.
Stratman, AN et al. (2010) "Endothelial-derived PDGF-BB and HB-EGF coordinately regulate pericyte recruitment during vasculogenic tube assembly and stabilization." Blood 116: 4720-4730.
Stupack, DC, Cheresh, DA, "Integrins and angiogenesis," Curr. Top. Dev. Bio. (2004) 64: 207-38.
Sumbria RK, et al. A murine model of inflammation-induced cerebral microbleeds. J Neuroinflammation 2016;13:218.
Sundberg C, et al (2001) Glomeruloid microvascular proliferation follows adenoviral vascular permeability factor/vascular endothelial growth factor-164 gene delivery. Am J Pathol 158:1145-1160.
Sutherland GR, Auer RN (2006) "Primary intracerebral hemorrhage," J Clin Neurosci 13:511-517.
Tang, AT, et al, "Endothelial TLR4 and the microbiome drive cerebral cavernous malformations," Nature (2017) 545 (7654): 305-310.
Umemoto, et al; "Effects of a benidipine-based combination therapy on the risk of stroke according to stroke subtype: The COPE trial.", Hypertension Research, 36, 1088-1095, Aug. 29, 2013.
Van Der Flier A, et al (2001) "Function and interactions of integrins," Cell Tissue Res 305:285-298.
Vandewater L, et al (1985) Tumor cell generation of thrombin via functional prothrombinase assembly. Cancer Res 45:5521-5525.
Wada, T. et al (2012) "Antisense morpholino targeting just upstream from a poly(A) tail junction of material mRNA remoes the tail and inhibits translation," Nucleic Acids Res. 40 (22): e173.
Wakisaka Y, et al (2010) "Spontaneous intracerebral hemorrhage during acute and chronic hypertension in mice,". J Cereb Blood Flow Metab 30:56-69.
Wang, C. et al, (2010) "Rossuvastatin, identified from a zebrafish chemical genetic screen for anti-angiogenic compounds, suppresses the growth of prostate cancer," Eur. Urol. 58: 418-26.
Fisher MJ (2013) "Brain regulation of thrombosis and hemostasis: from theory to practice," Stroke 44:3275-3285.
Flaster, M., et al, (2011) "Statins in hemorrhagic stroke," Expert Rev Neurother 11:1141-1149.
Folkman J. (2007) Angiogenesis: an organizing principle for drug discovery? Nat Rev Drug Discov. 6:273-286.
Frank SR, Hansen SH (2008) "The PIX-GIT complex: a G protein signaling cassette in control of cell shape," Semin Cell Dev Biol 19:234-244.
Gaengel K, et al (2009) "Endothelial-mural cell signaling in vascular development and angiogenesis." Arterioscler Thromb Vasc Biol. 29:630-638.
Galli SJ (1997) The Paul Kallos Memorial Lecture. The mast cell: a versatile effector cell for a challenging world. Int Arch Allergy Immunol 113:14-22.
Galli SJ (2000) Mast cells and basophils., Curr Opin Hematol 7:32-39.
Gao, J. et al (2009) "CAAX-box protein, prenylation process and carcinogenesis," Am. J. Trans. Res. 1(3): 312-25.
Gjini E, et al. Zebrafish Tie-2 shares a redundant role with Tie-1 in heart development and regulates vessel integrity. Dis Model Mech 2011;4:57-66.
Goldstein LB, et al (2008) "Hemorrhagic stroke in the Stroke Prevention by Aggressive Reduction in Cholesterol Levels study," Neurology 70:2364-2370.
Gore AV, et al (2008) "Combinatorial interaction between CCM pathway genes precipitates hemorrhagic stroke," Dis Model Mech 1:275-281.
Grant, DS and Kleinman, HK (1997) "Regulation of capillary formation by laminin and other components of the extracellular matrix." EXS 79: 317-333.
Greenberg SM, et al (2004) "Hemorrhage burden predicts recurrent intracerebral hemorrhage after lobar hemorrhage," Stroke 35:1415-1420.
Haussen DC, et al (2012) "Statin use and microhemorrhages in patients with spontaneous intracerebral hemorrhage," Stroke 43:2677-2681.
Hemphill JC, 3rd, et al. Guidelines for the management of spontaneous intracerebral hemorrhage: A guideline for healthcare professionals from the American Heart Association/American Stroke Association. Stroke. 2015;46:2032-2060.
Henikoff, S, et al, "Amino Acid Substitution Matrices From Protein Blocks", (1989) Proc. Natl. Acad. Sci. USA 89:10915-10919.
Herzig MC, et al. Abeta is targeted to the vasculature in a mouse model of hereditary cerebral hemorrhage with amyloidosis. Nat Neurosci. 2004;7(9):954-60.
Higgins, D. G., et al, "Fast and sensitive multiple sequence alignments on a microcomputer", (1989) CABIOS 6:151-153.
Higgins, D.G., et al, "Clustal: a package for performing multiple sequence alignment on a microcomputer", (1988), Gene 73:237-244.

(56) References Cited

OTHER PUBLICATIONS

Huang, X., et al., "Parallelization of a local similarity algorithm", (1992) Computer Applications in the Biosciences 8:155-165.
Imaizumi T, et al (2004) "Dotlike hemosiderin spots on T2*—weighted magnetic resonance imaging as a predictor of stroke recurrence: a prospective study," J Neurosurg 101:915-920.
Ioannidou S, et al (2006) An in vitro assay reveals a role for the diaphragm protein PV-1 in endothelial fenestra morphogenesis. Proc Natl Acad Sci U S A 103:16770-16775.
Jain RK (1988) Determinants of tumor blood flow: a review. Cancer Res 48:2641-2658.
Karlin, S., et al, "Applications and Statistics for Multiple High-scoring Segments in Molecular Sequences", (1993) Proc. Natl. Acad. Sci. USA 90:5873-5787.
Katoh M, Katoh M. (2007) "WNT signaling pathway and stem cell signaling network." Clin Cancer Res. 13:4042-4045.
Katoh Y, Katoh M. (2008) "Hedgehog signaling, epithelial-to-mesenchymal transition and miRNA," Int J Mol Med. 22:271-275.
Katoh, M., (2013) "Therapeutics targeting angiogenesis: genetics and epigenetics, extracellular miRNAs and signaling networks," Intl J. Mol. Med. 32(4): 763-67.
Katoh, M., Nakagama, H., (2014) "FGF receptors: cancer biology and therapeutics," Med. Res. Rev. 34(2): 280-300.
Kitamura, T et al, "Regulation of VEGF-mediated angiogenesis by the Akt/PKB substrate Girdin," Nat. Cell Biol. (2008): 10(3): 329-337.
Kohn S, et al (1992) Pathways of macromolecular tracer transport across venules and small veins. Structural basis for the hyperpermeability of tumor blood vessels. Lab Invest 67:596-607.
Kouklis, P. et al (2003) VE-cadherin-induced Cdc42 signaling regulates formation of membrane protrusions in endothelial cells, J. Biol. Chem. 278: 16230-36.
Leblanc, AJ et al, (2012) "Microvascular repair—post-angiogenesis vascular dynamics," Microcirculation 19(8): 10.1111/j.1549-8719.2012.00207.x.
Li DY, Whitehead KJ (2010) "Evaluating strategies for the treatment of cerebral cavernous malformations," Stroke 41:S92-S94.
Li Q, Mattingly RR (2008) "Restoration of E-cadherin cell—cell junctions requires both expression of E-cadherin and suppression of ERK MAP kinase activation in Ras-transformed breast epithelial cells," Neoplasia 10:1444-1458.
Li, C. et al,"The maternal immune response to fetal platelet GpIb? causes frequent miscarriage in mice that can be prevented by intravenous IgG and anti-FcRn therapies," J. Clin. Invest. (2011) 121(11): 4537-47.
Liu J, et al (2007) "A betaPix Pak2a signaling pathway regulates cerebral vascular stability in zebrafish," Proc Natl Acad Sci U S A 104:13990-13995.
Liu J, et al (2012) "βPix plays a dual role in cerebral vascular stability and angiogenesis, and interacts with integrin alphavbeta8," Dev Biol 363:95-105.
Liu S, et al (2013) "A mouse model of cerebral microhemorrhages," Stroke 44:AWP297 (Abstract).
Liu S, et al. (2014) "Comparative analysis of H & E and prussian blue staining in a mouse model of cerebral microbleeds." J Histochem Cytochem. 62:767-773.

Loberg, RD, et al. (2002), "Enhanced Glycogen Synthase Kinase-3β Activity Mediates Hypoxia-induced Apoptosis of Vascular Smooth Muscle Cells and Is Prevented by Glucose Transport and Metabolism", J. Biol. Chem. 277 (44): 41667-416673.
Majno G, et al, (1961) Studies on inflammation. II. The site of action of histamine and serotonin along the vascular tree: a topographic study. J Biophys Biochem Cytol 11:607-626.
Majno G, et al, (1969) Endothelial contraction induced by histamine-type mediators: an electron microscopic study. J Cell Biol 42:647-672.
Mayrovitz HN, et al. (1975) "Microvascular hemodynamic variations accompanying microvessel dimensional changes." Microvasc Res. 10:322-29 Box 1.
Mayrovitz HN, et al. (1977) "Relationship between microvascular blood velocity and pressure distribution." Am J Physiol.;232:H400-5.
Mazein, A. et al. (2013) "A comprehensive machine-readable view of the mammalian cholesterol biosynthesis pathway," Biochemical Pharmacol. 86: 56-66.
McDonald DA, et al, (2012) "Fasudil decreases lesion burden in a murine model of cerebral cavernous malformation disease," Stroke 43:571-574.
Miscevic F, et al (2012) "Advances in zebrafish high content and high throughput technologies," Comb Chem High Throughput Screen 15:515-521.
Montero-Balaguer M, et al (2009) "Stable vascular connections and remodeling require full expression of VE-cadherin in zebrafish embryos," PLoS One 4:e5772.
Morgenstern LB, et al (2010) "Guidelines for the management of spontaneous intracerebral hemorrhage: a guideline for healthcare professionals from the American Heart Association/American Stroke Association," Stroke 41:2108-2129.
Nagy JA, et al (1995) Pathogenesis of ascites tumor growth: vascular permeability factor, vascular hyperpermeability, and ascites fluid accumulation. Cancer Res 55:360-368.
Weis, M. et al (2002) "Statins have biphasic effects on angiogenesis," Cir. Res. 105: 739-45.
Wootton, J.C., et al, "Statistics of Local Complexity in Amino Acid Sequences and Sequence Databases", (1993), Comput. Chem., 17:149-163.
Yakushiji Y, et al (2012) "Distributional impact of brain microhemorrhages on global cognitive function in adults without neurological disorder," Stroke 43:1800-1805.
Yougbare, I. et al., "Maternal anti-platelet ?3 integrins impair angiogenesis and cause intracranial hemorrhage," (2015) J. Clin. Invest. 125(4): 1545-1556.
Zhang, F.L. and Casey, PJ (1996) "Protein Prenylation: Molecular Mechanisms and Functional Consequences," Ann. Rev. Biochem. 65: 241-69.
Zhu J, et al (2002) "?8 integrins are required for vascular morphogenesis in mouse embryos," Development 129:2891-2903.
Zuo, et al "The Potential Therapeutic Effects of Artesunate on Stroke and Other Central Nervous System Diseases", BioMed Research International, Nov. 20, 2016.

* cited by examiner

Figure 4
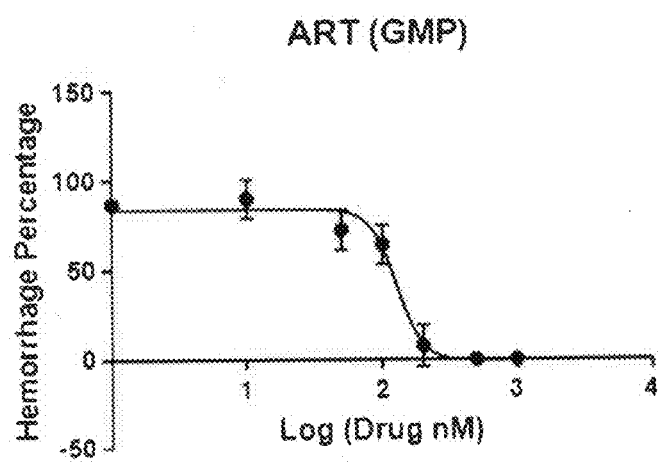
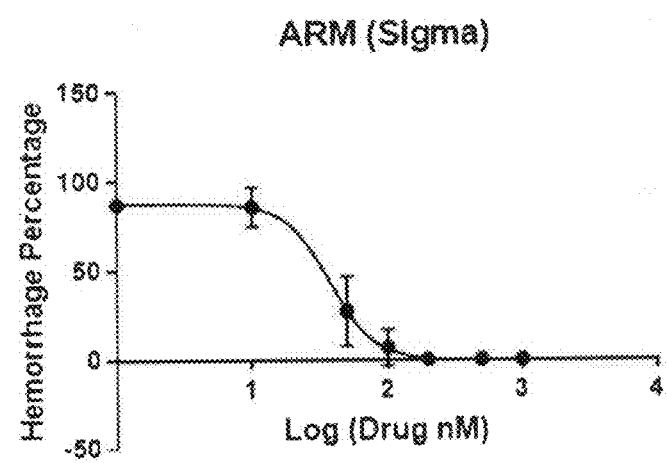

Figure 5
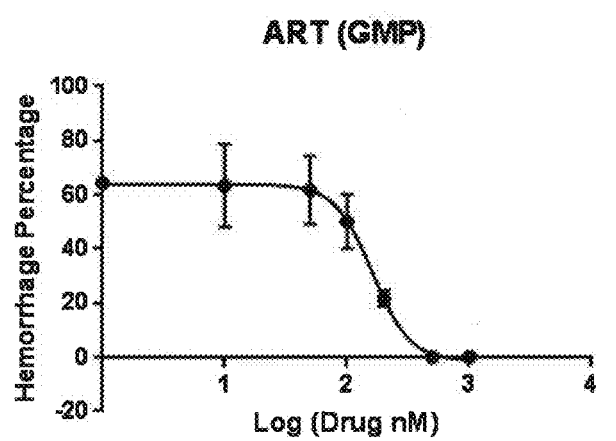
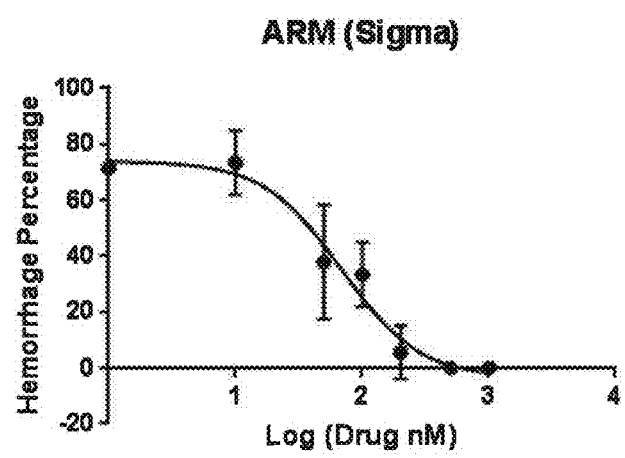

Figure 8
A
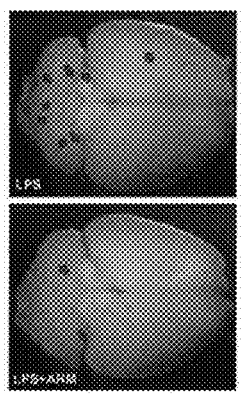
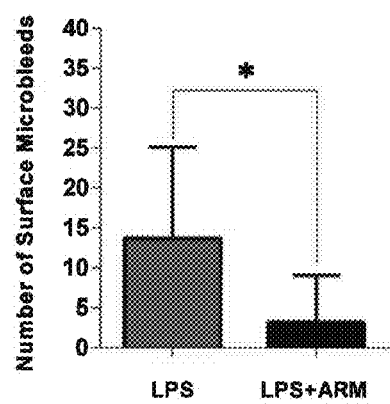
B
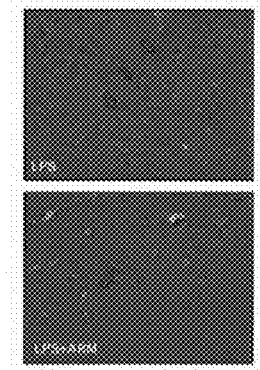
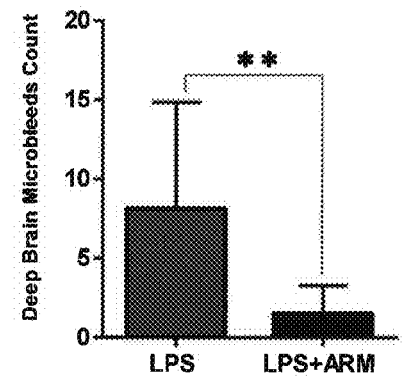

FIGURE 13
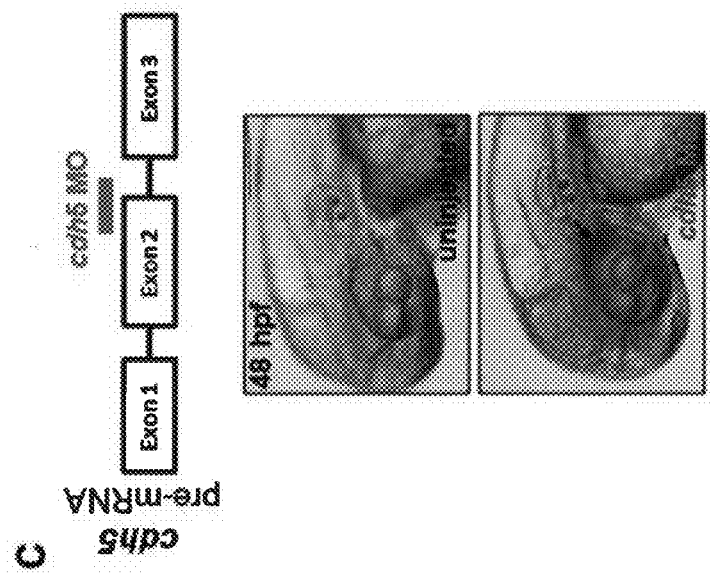
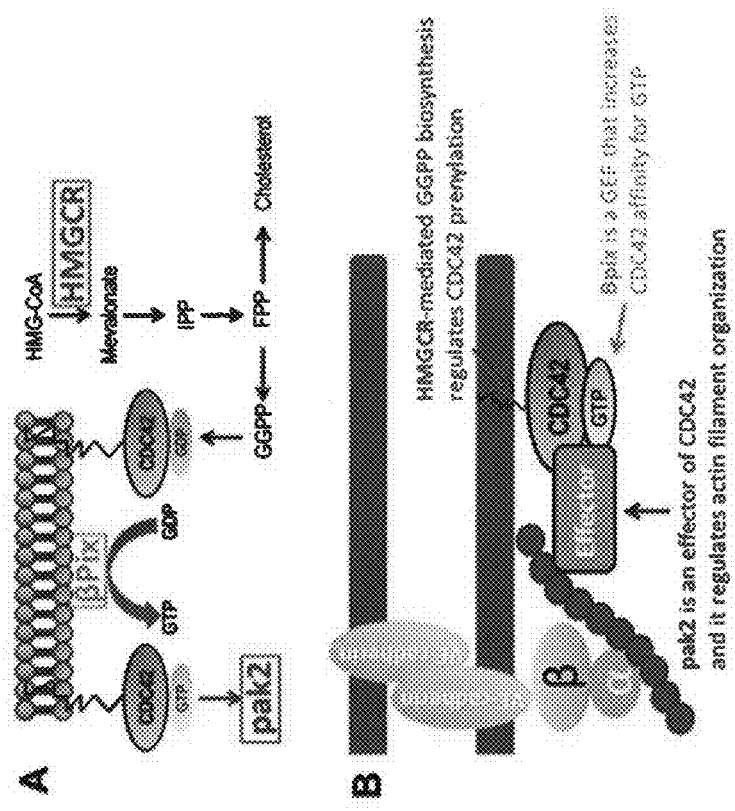

FIGURE 15
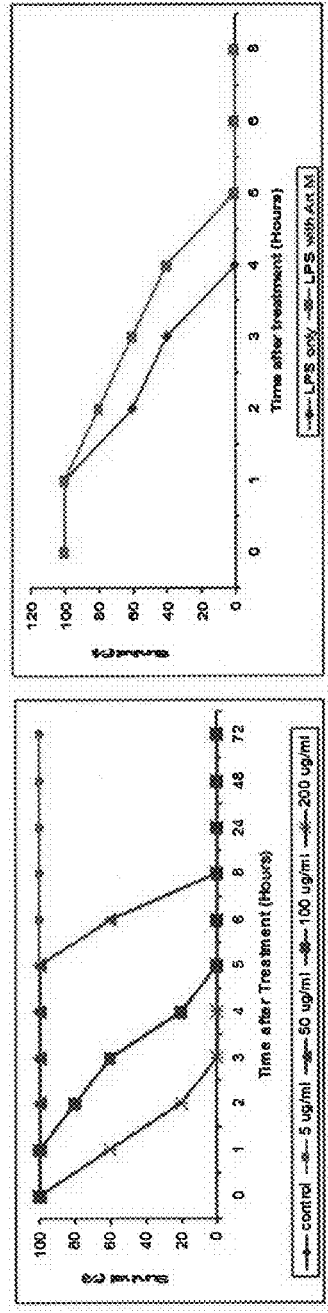
A. Survival curve of larval zebrafish on various concentrations of LPS  B. Artemether has protective effect on LPS-induced mortality
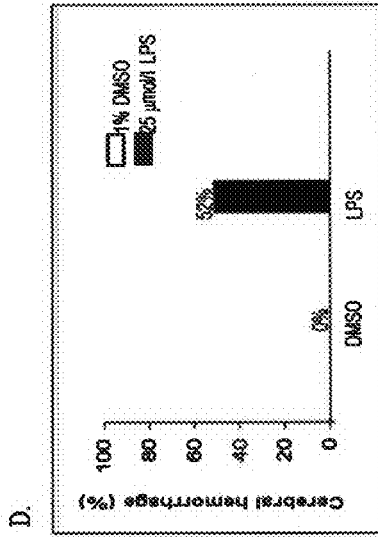
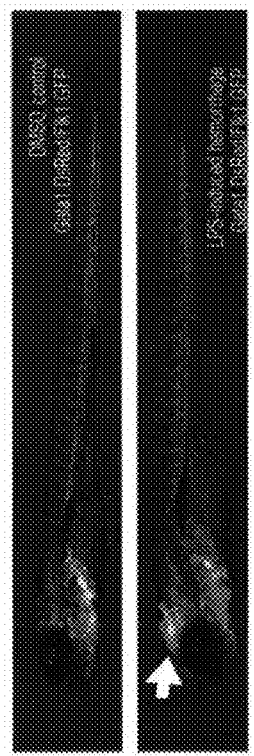
C. LPS induced brain hemorrhage in developing zebrafish embryos

SMALL MOLECULE THERAPEUTIC COMPOUNDS THAT REDUCE THE INCIDENCE OF INTRACEREBRAL HEMORRHAGE AND BRAIN MICROHEMORRHAGES

CROSS-REFERENCE TO RELATED APPLICATIONS

This application claims the benefit of priority to U.S. provisional application No. 62/370,077 (filed Aug. 2, 2016), entitled SMALL MOLECULE THERAPEUTIC COMPOUNDS THAT REDUCE THE INCIDENCE OF INTRACEREBRAL HEMORRHAGE AND BRAIN MICROHEMORRHAGES, which is incorporated by reference herein in its entirety.

FIELD OF THE INVENTION

The described invention relates to small molecule therapeutic compounds capable of reducing the incidence of intracerebral hemorrhage and brain microhemorrhages.

BACKGROUND

Many pathologic conditions cause a destabilization of the vascular network resulting in endothelial hyperpermeability, excessive vascular sprouting, and angiogenesis. (Smith M C P, Li, D Y, Whitehead, K J (2010) "Mechanisms of vascular stability and the relationship to human disease," Curr. Opin. Hematol. 17(30: 237-44).

Vascular Permeability

Vascular permeability is an extremely complex process that, in different settings, involves distinctly different types of blood vessels and makes use of different anatomic and molecular pathways.

While the vascular system of higher organisms is often described as "closed", it needs to be sufficiently "open" (i.e., "permeable") to allow the ready exchange of small molecules (gases, nutrients, waste products) with the tissues. (Nagy, J. A., Benjamin, L., Zeng, H., Dvorak, A. M., Dvorak, H. F. (2008) "Vascular permeability, vascular hyperpermeability and angiogenesis," Angiogenesis 11(2): 109-119). Plasma proteins also need to cross the normal vascular barrier, at least in small amounts.

Permeability, meaning the net amount of a solute, typically a macromolecule, that has crossed a vascular bed and accumulated in the interstitium in response to a vascular permeabilizing agent or at a site of pathological angiogenesis, is an extremely complicated process that is affected by many different variables. Id. These include the intrinsic properties of the different types of microvessels involved (capillaries, venules, mother vessels (MV)); the size, shape, and charge of extravasating molecules; the anatomic pathways molecules take in crossing the endothelial cell barrier; the time course over which permeability is measured; and the animals and vascular beds that are being investigated. Id.

Basal Vascular Permeability (BVP)

Molecular exchange in normal tissues takes place primarily in capillaries, largely by diffusion. The molecules exchanged consist largely of gases ($O_2$ and $CO_2$), water, small molecules such as salts and sugars, and only small amounts of plasma proteins. Id. The extent of BVP varies considerably in different normal tissues and is subject to substantial change in response to changes in hydrostatic pressure, opening of closed vessels, surface area available for exchange, blood flow, etc. Id.

Water and lipophilic solutes (e.g., gases such as $O_2$ and $CO_2$) are able to diffuse through endothelial cells; they also pass readily through inter-endothelial cell junctions and through endothelial fenestrae. Id. Small lipophilic molecules can also dissolve in endothelial cell membranes and so pass from the vascular lumen to the interstitium. Id. Capillary endothelial cells contain large numbers of small (about 70 nm diameter) vesicles (caveolae) the majority of which are found connected to the luminal and abluminal plasma membranes by means of stomata that are generally closed by thin diaphragms containing plasmalemmal vesicle associated protein (PV-1), an endothelial-specific integral membrane glycoprotein associated with the stomatal diaphragms of vaveolae, transendothelial channels, and vesiculo-vacuolar organelles and the diaphragms of endothelial fenestrae. (Stan, R V, Tkachenko, E., Niesman, I R, (2004), "PV1 is a key structural component for the formation of the stomatal and fenestral diaphragms," Mol. Biol. Cell 15(8): 3615-30). Others are in the cytoplasm.

Acute Vascular Hyperpermeability (AVH)

A rapid increase in vascular permeability occurs when the microvasculature is exposed acutely to any of a number of vascular permeabilizing factors, for example, VEGF-A, histamine, serotonin, PAF, etc. Some of these agents (e.g., histamine, serotonin, VEGF-A) are normally stored in tissue mast cells (Nagy, J. A., Benjamin, L., Zeng, H., Dvorak, A. M., Dvorak, H. F. (2008) "Vascular permeability, vascular hyperpermeability and angiogenesis," Angiogenesis 11(2): 109-119, citing Boesiger J, Tsai M, Maurer M et al (1998) Mast cells can secrete vascular permeability factor/vascular endothelial cell growth factor and exhibit enhanced release after immunoglobulin E-dependent upregulation of fc epsilon receptor I expression. J Exp Med 188:1135-1145; Galli S J (2000) Mast cells and basophils. Curr Opin Hematol 7:32-39; Galli S J (1997) The Paul Kallos Memorial Lecture. The mast cell: a versatile effector cell for a challenging world. Int Arch Allergy Immunol 113:14-22) and so may be released by agents that cause mast cell degranulation, e.g., allergy, insect bites, etc. Single exposure to any of these permeability factors results in a rapid but self-limited (complete by 20-30 min) influx of plasma into the tissues.

The quantity of extravasated fluid in AVH is greatly increased above that found in BVP and its composition is greatly changed. The fluid that extravasates in AVH is rich in plasma proteins, approaching the levels found in plasma, and is referred to as an exudate. Id. Among the plasma proteins that extravasate are fibrinogen and various members of the blood clotting cascade. Id. When these come into contact with tissue factor, a protein that is normally expressed by many interstitial cells, the clotting system is activated and the exudate clots to deposit fibrin (Id. Citing Dvorak H F, Quay S C, Orenstein N S et al (1981) Tumor shedding and coagulation. Science 212:923-924; VanDeWater L, Tracy P B, Aronson D et al (1985) Tumor cell generation of thrombin via functional prothrombinase assembly. Cancer Res 45:5521-5525). Fibrin forms a gel that traps water and other solutes, restraining their clearance by lymphatics or capillaries and resulting in tissue swelling (edema). Id. As long as the permeability stimulus is not continuous, the deposited fibrin is rapidly degraded without further consequences. Id.

AVH also differs from BVP in that the vascular leakage takes place from post-capillary venules, highly specific vessels just downstream of capillaries (Id. Citing Majno G, Palade G E, Schoefl G I (1961) Studies on inflammation. II. The site of action of histamine and serotonin along the vascular tree: a topographic study. J Biophys Biochem Cytol 11:607-626; Majno G, Shea S M, Leventhal M (1969) Endothelial contraction induced by histamine-type mediators: an electron microscopic study. J Cell Biol 42:647-672). It has been proposed that histamine and other vascular permeabilizing agents induce endothelial cells to contract and pull apart to form intercellular (paracellular) gaps of sufficient size to permit plasma-protein extravasation. Id. In addition, venular epithelium contains a structure, the vesiculo-vacuolar organelle (VVO), that offers an alternative, trans-endothelial cell route for plasma extravasation in response to permeability factors (Id. citing Kohn S, Nagy J A, Dvorak H F et al (1992) Pathways of macromolecular tracer transport across venules and small veins. Structural basis for the hyperpermeability of tumor blood vessels. Lab Invest 67:596-607; Dvorak A M, Kohn S, Morgan E S et al (1996) The vesiculo-vacuolar organelle (VVO): a distinct endothelial cell structure that provides a transcellular pathway for macromolecular extravasation. J Leukoc Biol 59:100-115; Feng D, Nagy J, Dvorak A et al (2000) Different pathways of macromolecule extravasation from hyperpermeable tumor vessels. Microvascular Research 59:24-37; Feng D, Nagy J A, Hipp J et al (1996) Vesiculo-vacuolar organelles and the regulation of venule permeability to macromolecules by vascular permeability factor, histamine, and serotonin. J Exp Med 183:1981-1986; Feng D, Nagy J A, Hipp J et al (1997) Reinterpretation of endothelial cell gaps induced by vasoactive mediators in guinea-pig, mouse and rat: many are transcellular pores. J Physiol 504(Pt 3):747-761). VVOs, which are grape-like clusters comprised of hundreds of uncoated, cytoplasmic vesicles and vacuoles that together form an organelle that traverses venular endothelial cytoplasm, often extend to inter-endothelial cell interfaces and their individual vesicles (unlike caveolae) commonly open to the inter-endothelial cell cleft. Id. The vesicles and vacuoles comprising VVOs vary in size from those the size of caveolae to vacuoles with volumes as much as 10-fold larger (Feng D, Nagy J A, Pyne K et al (1999) Pathways of macromolecular extravasation across microvascular endothelium in response to VPF/VEGF and other vasoactive mediators. Microcirculation 6:23-44). These vesicles and vacuoles are linked to each other and to the luminal and abluminal plasma membranes by stomata that are normally closed by thin diaphragms that appear similar to those found in caveolae. Id. It has been proposed that vascular permeability inducing agents cause the diaphragms interconnecting vesicles and vacuoles to open, thereby providing a transcellular pathway for plasma and plasma-protein extravasation. Id.

Chronic Vascular Hyperpermeability (CVH)

Chronic exposure to permeability factors results in profound changes in venular structure and function that lead to the chronic hyperpermeability of pathological angiogenesis as found in tumors, healing wounds, and chronic inflammatory diseases such as rheumatoid arthritis, psoriasis, cellular immunity, etc. (Id. Citing Dvorak H F (2003) Rous-Whipple award lecture. How tumors make bad blood vessels and stroma. Am J Pathol 162:1747-1757; Nagy J A, Masse E M, Herzberg K T et al (1995) Pathogenesis of ascites tumor growth: vascular permeability factor, vascular hyperpermeability, and ascites fluid accumulation. Cancer Res 55:360-368). As in AVH, the fluid that extravasates is an exudate that approaches the overall composition of plasma. In tumors fluid accumulation is generally associated with increased interstitial pressure (Id. Citing Jain R K (1988) Determinants of tumor blood flow: a review. Cancer Res 48:2641-2658); this increased pressure results from persistent vascular hyperpermeability, clotting of the exudate with deposition of a fluid-trapping fibrin gel, inadequate lymphatic drainage, and the restraints imposed by surrounding tissues that together limit fluid dissipation. Id. These restraints are nearly absent when tumors grow in or around body cavities such as the peritoneum where massive amounts of ascites fluid can accumulate. Id.

In contrast to BVP and AVH, fluid leakage in CVH does not take place from any type of normal blood vessel. Instead, whether in tumors or wounds, the blood vessels that leak are newly formed, angiogenic blood vessels; these are primarily mother vessels (MV), and also, to a lesser extent, glomeruloid microvascular proliferations (GMP) that form from MV (Id. Citing Nagy J A, Feng D, Vasile E et al (2006) Permeability properties of tumor surrogate blood vessels induced by VEGF-A. Lab Invest 86:767-780; Pettersson A, Nagy J A, Brown L F et al (2000) Heterogeneity of the angiogenic response induced in different normal adult tissues by vascular permeability factor/vascular endothelial growth factor. Lab Invest 80:99-115; Sundberg C, Nagy J A, Brown L F et al (2001) Glomeruloid microvascular proliferation follows adenoviral vascular permeability factor/vascular endothelial growth factor-164 gene delivery. Am J Pathol 158:1145-1160; Brown L F, Detmar M, Claffey K et al (1997) Vascular permeability factor/vascular endothelial growth factor: a multifunctional angiogenic cytokine. Exs 79:233-269; Brown L F, Yeo K T, Berse B et al (1992) Expression of vascular permeability factor (vascular endothelial growth factor) by epidermal keratinocytes during wound healing. J Exp Med 176:1375-1379; Ren G, Michael L H, Entman M L et al (2002) Morphological characteristics of the microvasculature in healing myocardial infarcts. J Histochem Cytochem 50:71-79. Mother Vessels are greatly enlarged sinusoids that arise from preexisting normal venules by a process that involves pericyte detachment, vascular basal lamina degradation, and a 4-5-fold increase in lumen size that is accompanied by extensive endothelial cell thinning. Id. Notwithstanding that Poiseuille's law indicates that blood flow (flow rate) is proportional to the fourth power of the vascular radius, MV exhibit sluggish blood flow because of their hyperpermeability to plasma which results in a striking increase in hematocrit. Id. The protein-rich exudates in CVH interact with tissue factor to trigger the clotting system and deposit fibrin (Id. Citing Dvorak H F, Quay S C, Orenstein N S et al (1981) Tumor shedding and coagulation. Science 212:923-924; VanDeWater L, Tracy P B, Aronson D et al (1985) Tumor cell generation of thrombin via functional prothrombinase assembly. Cancer Res 45:5521-5525).

Tissue factor is expressed on many tumor cells as well as host interstitial cells and is induced in endothelial cells by VEGF-A (Id). In addition to its fluid trapping properties, fibrin also has a number of other properties when it persists over time as in tumors and healing wounds. It provides a pro-angiogenic provisional stroma that induces and is later replaced by the ingrowth of new blood vessels and fibroblasts and the laying down of mature fibro-vascular stroma (Id. Citing Dvorak H F (2003) Rous-Whipple award lecture. How tumors make bad blood vessels and stroma. Am J Pathol 162:1747-1757; Dvorak H F, Orenstein N S, Carvalho A C et al (1979) Induction of a fibrin-gel investment: an early event in line 10 hepatocarcinoma growth mediated by tumor-secreted products. J Immunol 122:166-174; Dvorak H F, Dvorak A M, Manseau E J et al (1979) Fibrin gel investment associated with line 1 and line 10 solid tumor growth, angiogenesis, and fibroplasia in guinea pigs. Role of cellular immunity, myofibroblasts, microvascular damage, and infarction in line 1 tumor regression. J Natl Cancer Inst 62:1459-1472). Fibrin interacts with integrins expressed by multiple cell types, thereby supporting the migration of tumor cells as well as host mesenchymal cells (endothelial cells, pericytes, fibroblasts) and inflammatory cells (neutrophils, monocytes). Id. Fibrin also sequesters growth factors, protecting them from degradation, and induces the expression of proangiogenic molecules such as IL-8 and tissue factor. Id. Fragment E, a fibrin breakdown product, is directly pro-angiogenic (Id.). Macromolecules extravasate from MV and GMP largely via a transcellular route (Id. Citing Nagy J A, Feng D, Vasile E et al (2006) Permeability properties of tumor surrogate blood vessels induced by VEGF-A. Lab Invest 86:767-780).

In short, while agents such as VEGF-A have long been known to induce AVH and CVH, apart from hemodynamic factors, much less is known about the molecular events that are responsible for the normal permeability of BVP, and even less is known about the molecules that are involved in regulating permeability, and the molecular mechanisms that govern each of the different types of permeability may well be different. The signaling pathways by which even such well-studied molecules as eNOS and caveolin-1 act to induce permeability are poorly understood. Id. Little is known about the molecular mechanisms that regulate such critical events as caveolar shuttling, the opening of VVO diaphragms, the formation of fenestrae, changes in endothelial cell junctions, etc. (Id. Citing Dejana E (2004) Endothelial cell-cell junctions: happy together. Nat Rev Mol Cell Biol 5:261-270; Oh P, Borgstrom P, Witkiewicz H et al (2007) Live dynamic imaging of caveolae pumping targeted antibody rapidly and specifically across endothelium in the lung. Nat Biotechno125:327-337; Ioannidou S, Deinhardt K, Miotla J et al (2006) An in vitro assay reveals a role for the diaphragm protein PV-1 in endothelial fenestra morphogenesis. Proc Natl Acad Sci USA 103:16770-16775).

Angiogenesis

Angiogenesis is a process of neovascular formation from pre-existing blood vessels during embryogenesis, adult tissue homeostasis and carcinogenesis. (Katoh, M., (2013) "Therapeutics targeting angiogenesis: genetics and epigenetics, extracellular miRNAs and signaling networks," Intl J. Mol. Med. 32(4): 763-67, citing Carmeliet P. (2005) Angiogenesis in life, disease and medicine. Nature. 438:932-936; Ferrara N, Kerbel R S. (2005) Angiogenesis as a therapeutic target. Nature. 438:967-974; Folkman J. (2007) Angiogenesis: an organizing principle for drug discovery? Nat Rev Drug Discov. 6:273-286; Carmeliet P, Jain R K. (2011) Molecular mechanisms and clinical applications of angiogenesis. Nature. 473:298-307). It is distinct from vasculogenesis which is the developmental in situ differentiation and growth of blood vessels from mesodermal derived hemangioblasts.

Angiogenesis occurs in multiple steps as follows: i) vascular destabilization induced by degradation of the basement membrane and decreased adhesion of endothelial cells; ii) angiogenic sprouting resulting from the migration of endothelial tip cells and the proliferation of endothelial stalk cells; iii) lumen formation by endothelial cells and the recruitment of pericytes to the surrounding region of the endothelial lumen; iv) vascular stabilization depending on tight junctions and basement membrane. (Katoh, M., (2013) "Therapeutics targeting angiogenesis—genetics and epigenetics, extracellular miRNAs and signaling networks," Intl J. Mol. Med. 32(4): 763-67, citing Carmeliet P. (2005) Angiogenesis in life, disease and medicine. Nature. 438:932-936).

Vascular endothelial growth factor (VEGF), fibroblast growth factor (FGF2), angiopoietins (ANGPT1 and ANGPT2), Notch ligands [jagged 1 (JAG1) and Delta like ligand 4 (DLL4)] and transforming growth factor-β (TGF-β) regulate angiogenesis through their receptors on vascular endothelial cells. VEGF activates the endothelial nitric acid oxide synthase (eNOS), SRC, RAS-ERK and PI3K-AKT signaling cascades through VEGFR2 receptor on endothelial cells, which induce vascular permeability, endothelial migration, proliferation and survival, respectively (Id. Citing Coultas L, Chawengsaksophak K, Rossant J. (2005) "Endothelial cells and VEGF in vascular development." Nature. 438:937-945; Olsson A K, Dimberg A, Kreuger J, Claesson-Welsh L. (2006) "VEGF receptor signaling-in control of vascular function." Nat Rev Mol Cell Biol. 7:359-371). FGF2 promotes angiogenesis directly through FGFR1 receptor on endothelial cells via signaling cascades similar to VEGF, or indirectly through VEGF secretion from endothelial cells, cardiomyocytes and stromal cells (Id. Citing Presta M, Dell'Era P, Mitola S, et al. (2005) "Fibroblast growth factor/fibroblast growth factor receptor system in angiogenesis." Cytokine Growth Factor Rev. 16:159-178). ANGPT1, secreted from pericytes, activates TEK/TIE2 receptor to maintain endothelial quiescence or stabilization, whereas ANGPT2, secreted from endothelial cells themselves by VEGF or hypoxia signaling, inhibits TEK to promote endothelial activation or sprouting (Id. Citing Fagiani E, Christofori G. (2013) "Angiopoietins in angiogenesis." Cancer Lett. 328:18-26). JAG1-Notch signaling promotes angiogenic sprouting, whereas DLL4-Notch signaling inhibits angiogenic sprouting (Id. Citing Bridges E, Oon C E, Harris A. (2011) "Notch regulation of tumor angiogenesis." Future Oncol. 7:569-588). TGF-β signaling through TGFBR1/ALK5 receptor to the Smad2/3 cascade inhibits endothelial cell activation, maintaining endothelial quiescence, whereas TGF-β signaling through the ACVRL1/ALK1 receptor to the Smad1/5 cascade promotes the migration and proliferation of endothelial cells (Id. Citing Gaengel K, Genové G, Armulik A, Betsholtz C. (2009) "Endothelial-mural cell signaling in vascular development and angiogenesis." Arterioscler Thromb Vasc Biol. 29:630-638). The VEGF, FGF, Notch and TGF-β signaling cascades are directly involved in the angiogenic signaling of endothelial cells (Id).

The VEGF, FGF, Notch and TGF-β signaling cascades cross-talk with WNT and Hedgehog signaling cascades to constitute the stem-cell signaling network (Id. Citing Katoh M, Katoh M. (2007) "WNT signaling pathway and stem cell signaling network." Clin Cancer Res. 13:4042-4045; Katoh Y, Katoh M. (2008) "Hedgehog signaling, epithelial-to-mesenchymal transition and miRNA," Int J Mol Med. 22:271-275). DVL2-binding deubiquitinase FAM105B regulates WNT signaling and angiogenesis (Id. Citing Rivkin E, Almeida S M, Ceccarelli D F, et al. (2013) "The linear ubiquitin-specific deubiquitinase gumby regulates angiogenesis." Nature 498:318-324), while Hedgehog signaling is involved in the regulation of liver sinusoidal endothelial cells (Id. Citing Diehl A M. (2012) "Neighborhood watch orchestrates liver regeneration." Nat Med. 18:497-499). FGF, Notch and canonical WNT signaling are involved in cell-fate determination based on mutual transcriptional regulation, whereas FGF, Notch, TGF-β, Hedgehog and non-canonical WNT signaling are involved in epithelial-to-mesenchymal transition (EMT) due to the upregulation of SNAI1 (Snail), SNAI2 (Slug), ZEB1, ZEB2 and TWIST (Katoh, M., Nakagama, H., (2014) "FGF receptors: cancer biology and therapeutics," Med. Res. Rev. 34(2): 280-300). EMT is a cellular process similar to endothelial-to-mesenchymal transition (EndMT). Hypoxia induces angiogenesis as a result of VEGF upregulation (Dewhirst M W, Cao Y, Moeller B. (2008) "Cycling hypoxia and free radicals regulate angiogenesis and radiotherapy response." Nat Rev Cancer. 8:425-437). Angiogenesis is orchestrated by the VEGF, FGF, Notch, TGF-β, Hedgehog and WNT signaling cascades, which directly or indirectly regulate the quiescence, migration and proliferation of endothelial cells.

During the earliest stages of angiogenesis, such as in response to the angiogenic cytokine VEGF induced by wounding and ischemia, vascular basement membrane is degraded (Senger, D R, and David, G E, (2011) "Angiogenesis," Cold Spring Harb. Perspect. Biol. Aug. 3(8): a005090 citing Sundberg, C. et al. (2001) "Glomeruloid microvascular proliferation follows adenoviral vascular permeability factor/VEGF-164 gene delivery," Am J Pathol 158: 1145-1160; Rowe, R G and Weiss, S J (2008) "Breaching the basement membrane: Who, when and how?" Trends Cell Biol 18: 560-574; Chang S H et al. (2009) "VEGF-A induces angiogenesis by perturbing the cathepsin-cysteine protease inhibitor balance in venules, causing basement membrane degradation and mother vessel formation," Cancer Res 69: 4537-4544). Following disruption of basement membrane, and with the ensuing stage known as vascular sprouting (Id. Citing Nicosia, R F and Madri, J A (1987) "The microvascular extracellular matrix. Developmental changes during angiogenesis in the aortic ring-plasma clot model." Am J Pathol 128: 78-90)), vessels become leaky and hyperpermeable to blood plasma proteins (Id. Citing Sundberg, C. et al. (2001) "Glomeruloid microvascular proliferation follows adenoviral vascular permeability factor/vascular endothelial growth factor-164 gene delivery." Am J Pathol 158: 1145-1160). This vascular hyperpermeability causes leakage of the plasma proteins fibrinogen, vitronectin, and fibronectin from the blood (Id. Citing Senger, D R (1996) "Cell migration promoted by a potent GRGDS-containing thrombin-cleavage fragment of osteopontin." Biochim Biophys Acta 1314: 13-24; Sundberg, C. et al. (2001) "Glomeruloid microvascular proliferation follows adenoviral vascular permeability factor/vascular endothelial growth factor-164 gene delivery." Am J Pathol 158: 1145-1160). Fibrinogen is subsequently converted to fibrin through enzymatic coagulation, and together with extravasated vitronectin and fibronectin instantly transform the interstitial collagen matrix to form a new, provisional ECM. Thus, the early stages of sprouting angiogenesis are generally believed to proceed in an environment rich in preexisting interstitial collagens in combination with fibrin, vitronectin, and fibronectin derived from the blood plasma. As vascular morphogenesis proceeds and vascular sprouts acquire lumens and mature, neovessels are again enshrouded in vascular basement membrane with associated pericytes and thereby achieve stability (Id. Citing Grant, D S and Kleinman, H K (1997) "Regulation of capillary formation by laminin and other components of the extracellular matrix." EXS 79: 317-333; Benjamin, L E et al. (1999) "Selective ablation of immature blood vessels in established human tumors follows vascular endothelial growth factor withdrawal." J Clin Invest 103: 159-165). Pericyte recruitment to vascular tubes directly controls this basement membrane assembly step in vitro and in vivo (Id. Citing Stratman, A N et al. (2009) "Pericyte recruitment during vasculogenic tube assembly stimulates endothelial basement membrane matrix formation." Blood 114: 5091-5101; Stratman, A N et al. (2010) "Endothelial-derived PDGF-BB and HB-EGF coordinately regulate pericyte recruitment during vasculogenic tube assembly and stabilization." Blood 116: 4720-4730).

Thus, in response to stimulation with angiogenic cytokines, angiogenesis in the adult is generally believed to proceed through the following basic stages: (1) degradation of vascular basement membrane and activation of quiescent endothelial cells (ECs); (2) sprouting and proliferation of ECs within provisional ECM; (3) lumen formation within the vascular sprouts, thereby creating vascular tubes; and (4) coverage of vascular tubes with mature vascular basement membrane in association with supporting pericytes.

Neovascularization

While often considered synonymous with angiogenesis (formation of new vessels from existing vessels), neovascularization involves a much broader series of temporally controlled vascular processes beginning with angiogenesis and progressing through multiple phases resulting in the formation of a new functional circulatory network (LeBlanc, A J et al, (2012) "Microvascular repair—post-angiogenesis vascular dynamics," Microcirculation 19(8): 10.1111/j.1549-8719.2012.00207.x). At the onset of neovascularization, relevant microvessel segments relax their stable vessel structure and initiate vessel sprouting leading to the formation of new vessel segments. (Id). Subsequently, the newly formed neovessels remodel via vascular cell differentiation and incorporation of perivascular cells into the newly formed vessel walls resulting in the appropriate density and distribution of arterioles, venules, and capillaries. (Id). Finally, the newly formed vascular network matures and remodels into a more efficient perfusion circuit that meets tissue perfusion needs and function. (Id).

Effective adult tissue neovascularization, whether by native or therapeutic means, results in an expanded vascular network and increased blood perfusion pathway length resulting in the appropriate delivery of more blood to tissues (Id).

While there is no one stereotypical vascular architecture, microvascular networks generally involve a branched network of progressively smaller caliber small arteries/arterioles at the inflow side delivering blood to the distal capillaries which subsequently drain into a branched network of increasingly larger caliber outflow venules/small veins, although there are variations of this basic network organization, often reflecting tissue and/or organ specific function (Id). Each of the three general vascular compartments (arterioles, capillaries, and venules) performs different functions in the microcirculation due to their structural and functional characteristics and their locations within the vasculature (Id). Arterioles provide the greatest resistance to blood flow in the vascular circuit with most of this resistance attributed to 1st and 2nd branch order arterioles (Id. Citing Mayrovitz H N, Wiedeman M P, Noordergraaf A. (1975) "Microvascular hemodynamic variations accompanying microvessel dimensional changes." Microvasc Res. 10:322-29 Box 1). This is primarily due to the relative larger diameter differences between the feeding arteries and the smaller arterioles and the relative fewer numbers of these proximal arterioles. The more prevalent downstream and terminal arterioles act to broadly distribute blood throughout the tissue and control, via vessel tone dynamics, blood flow into the most distal capillaries. The very small diameters and large numbers of capillaries make them ideal for supporting effective blood-tissue exchange of oxygen and other blood nutrients and molecules. Finally, venules, due in part to a relatively more compliant wall, serve as a high capacitance drainage system. Importantly, in a competent microcirculatory bed, as vessel diameters reduce within a vascular compartment the number of vessels in that compartment increase due to branching. This results in a sufficiently large enough cross-sectional area to keep resistance to blood flow across the compartment relatively low even though resistance within a single vessel segment might be high (due to the inverse relationship between resistance and the 4th power of the radius). Thus, to maintain proper resistances across the microvasculature, and therefore effective perfusion, proper branch ordering is critical. In addition, blood flow distribution in a tissue depends on the extent of branching in a logarithmic fashion (Mayrovitz H N, Tuma R F, Wiedeman M P. (1977) "Relationship between microvascular blood velocity and pressure distribution." Am J Physiol.; 232:H400-5). This normalized relationship between vessel caliber and vessel numbers (i.e. branching) is a critical feature of functional microvascular network architectures. Mismatches in this relationship lead to poor hemodynamic function typically observed as hypoperfusion and/or hypoxia within the tissue. Deficits in blood perfusion (e.g. ischemia, hypoxia) are a cause of and/or complication associated with a number of disease states including tissue infarction, necrosis, wound healing, tissue grafting, and organ dysfunction.

Microvascular Stability: Rho GTPase Cdc42 has been Implicated in the Mediation of Endothelial Barrier Function Endothelial adherens junctions (AJs) consist of transoligomers of membrane spanning vascular endothelial (VE)-cadherin proteins, which bind β-catenin through their cytoplasmic domain (Broman, M T et al (2006) "Cdc42 regulates adherens junction stability and endothelial permeability by inducing alpha-catenin interaction with the vascular endothelial cadherin complex," Cir. Res. 98: 73-80). β-catenin in turn binds α-catenin and connects the AJ complex with the actin cytoskeleton (Id). Rho GTPase Cdc42 regulates AJ permeability by controlling the binding of α-catenin with β-catenin and the consequent interaction of the VE-cadherin/catenin complex with the actin cytoskeleton (Id). β-catenin and the associated α-catenin may then serve as support sites for actin polymerization, leading to formation of long endothelial plasma membrane protrusions (Kouklis, P. et al (2003) VE-cadherin-induced Cdc42 signaling regulates formation of membrane protrusions in endothelial cells," J. Biol. Chem. 278: 16230-36). Non-junctional VE-cadherin thus actively participates in inside-out signaling at the plasma membrane, leading to the development of endothelial membrane protrusions (Id).

During inflammation, inflammatory mediators increase vascular permeability primarily by formation of intercellular gaps between endothelial cells of post-capillary venules. Spindler, V. et al (2010) "Role of GTPases in control of microvascular permeability," Cardiovasc. Res. 87(2): 243-53). Adherens junctions of endothelial cells need to be dynamic when endothelial junctions transiently open to allow passage of leukocytes from the blood into tissues. Rac1 and Cdc42 are the main GTPases required for barrier maintenance and stabilization. RhoA negatively regulates barrier properties (i.e., renders the barrier more permeable) under both resting and inflammatory conditions (Id). Rho GTPases (RhoA, Rac1 and Cdc42) or Rap1 are known to regulate cell adhesion in part by reorganization of the junction-associated cortical actin cytoskeleton (Id). Activated Cdc42 functions by counteracting the canonical RhoA-mediated mechanism of endothelial hyperpermeability (Ramchandran, R. et al (2008) "Critical role of Cdc42 in mediating endothelial barrier protection in vivo," Am. J. Physiol. Lung Cell Mol. Physiol. 295: 363-69), while Rac1-mediated barrier destabilization in microvascular endothelium appears to be largely restricted to conditions of enhanced endothelial cell migration and thus to be more closely related to angiogenesis rather than to inflammation. (Spindler, V. et al (2010) "Role of GTPases in control of microvascular permeability," Cardiovasc. Res. 87(2): 243-53)). Recent studies revealed that cAMP signaling, which is well known to be barrier protective, enhances barrier functions in part via Rap1-mediated activation of Rac1 and Cdc42 as well as by inhibition of RhoA. Moreover, barrier-stabilizing mediators directly activate Rac1 and Cdc42 or increase cAMP levels (Id). On the other hand, several barrier-disruptive components appear to increase permeability by reduced formation of cAMP, leading to both inactivation of Rac1 and activation of RhoA (Id).

The Cholesterol Biosynthesis Pathway

The mevalonate arm of the cholesterol biosynthesis pathway, which includes enzymatic activity in the mitochondria, peroxisome, cytoplasm and endoplasmic reticulum, starts with the consumption of acetyl-CoA, which occurs in parallel in 3 cell compartments (the mitochondria, cytoplasm, and peroxisome) and terminates with the production of squalene in the endoplasmic reticulum (Mazein, A. et al. (2013) "A comprehensive machine-readable view of the mammalian cholesterol biosynthesis pathway," Biochemical Pharmacol. 86: 56-66). The following are enzymes of the mevalonate arm:

Acetyl-CoA acetyltransferase (ACAT1; ACAT2; acetoacetyl-CoA thiolase; EC 2.3.1.9) catalyzes the reversible condensation of two molecules of acetylcoA and forms acetoacetyl-CoA (Id).

Hydroxymethylglutaryl-CoA synthase (HMGCS1 (cytoplasmic); HMGCS2 (mitochondria and peroxisome); EC 2.3.3.10 catalyzes the formation of 3-hydroxy-3-methylglutaryl CoA (3HMG-CoA) from acetyl CoA and acetoacetyl Co A (Id).

Hydroxymethylglutaryl-CoA lysase (mitochondrial, HMGCL; EC 4.1.3.4) transforms HMG-CoA into Acetyl-CoA and acetoacetate.

3-hydroxy-3-methylglutaryl-coenzyme A reductase (HMGCR; EC 1.1.34) catalyzes the conversion of 3HMG-CoA into mevalonic acid. This step is the committed step in cholesterol formation. HMGCR is highly regulated by signaling pathways, including the SREBP pathway (Id).

Mevalonate kinase (MVK; ATP: mevalonate 5-phosphotransferase; EC 2.7.1.36) catalyzes conversion of mevalonate into phosphomevalonate (Id).

Phosphomevalonate kinase (PMVK; EC 2.7.4.2) catalyzes formation of mevalonate 5-diphosphate from mevalonate 5-phosphate (Id).

Diphosphomevalonate decarboxylase (MVD; mevalonate (diphospho) decarboxylase; EC 4.1.1.33) decarboxylates mevalonate 5-diphosphate, forming isopentenyldiphosphate while hydrolyzing ATP (Id).

Isopentenyl-diphosphate delta-isomerases (ID11; ID12; EC 5.3.3.2) isomerize isopentenyl diphosphate into dimethylallyl diphosphate, the fundamental building blocks of isoprenoids (Id).

Farnesyl diphosphate synthase (FDPS; EC2.5.1.10; EC 2.5.1.1; dimethylallyltranstransferase) catalyzes two reactions that lead to farnesyl diphosphate formation. In the first (EC 2.5.1.1 activity), isopentyl diphosphate and dimethylallyl diphosphate are condensed to form geranyl disphosphate. Next, geranyl diphosphate and isopentenyl diphosphate are condensed to form farnesyl diphosphate (EC 2.5.1.10 activity) (Id).

Geranylgeranyl pyrophosphate synthase (GGPS1; EC 1.5.1.29; EC 2.5.1.10; farnesyl diphosphate synthase; EC 2.5.1.1; dimethylallyltranstransferase) catalyzes the two reactions of farnesyl diphosphate formation and the addition of three molecules of isopentenyl diphosphate to dimethylallyl diphosphate to form geranylgeranyl diphosphate (Id).

Farnesyl-diphosphate farnesyltransferase 1 (FDFT1; EC 2.5.1.21; squalene synthase) catalyzes a two-step reductive dimerization of two farnesyl diphosphate molecules (C15) to form squalene (C30). The FDFT1 expression level is regulated by cholesterol status; the human FDFT1 gene has a complex promoter with multiple binding sites for SREBP-1a and SREBP-2 (Id).

The sterol arms of the pathway start with Squalene and terminate with cholesterol production on the Bloch and Kandutsch-Russell pathways and with 24 (S),25-epoxycholesterol on the shunt pathway (Id). The following are enzymes of the sterol arms:

Squalene epoxidase (SQLE; EC 1.14.13.132, squalene monooxygenase) catalyzes the conversion of squalene into squalene-2,3-epoxide and the conversion of squalene-2,3-epoxide (2,3-oxidosqualene) into 2,3:22,23-diepoxysqualene (2,3:22,23-dioxidosqualene). The first reaction is the first oxygenation step in the cholesterol biosynthesis pathway. The second is the first step in 24(S),25-epoxycholesterol formation from squalene 2,3-epoxide (Id).

Lanosterol synthase (LSS; OLC; OSC; 2,3-oxidosqualene:lanosterol cyclase; EC 5.4.99.7) catalyzes cyclization of squalene-2,3-epoxide to lanosterol and 2,3:22,23-depoxysqualene to 24(S),25-epoxylanosterol (Id).

Δ(24)-sterol reductase (DHCR24; 24-dehydrocholesterol reductase; EC 1.3.1.72) catalyzes the reduction of the Δ-24 double bond of intermediate metabolites. In particular it converts lanosterol into 24, 25-dihydrolanosterol, the initial metabolite of the Kandutsch-Russel pathway and also provides the last step of the Bloch pathway converting desmosterol into cholesterol. Intermediates of the Bloch pathway are converted by DHCR24 into intermediates of the Kandutsch-Russell pathway (Id).

Lanosterol 14-α demethylase (CYP51A1; cytochrome P450, family 51, subfamily A, polypeptide 1; EC 1.14.13.70) converts lanosterol into 4,4-dimethyl-5α-cholesta-8,14,24-trien-3β-ol and 24,25-dihydrolanosterol into 4,4-dimethyl-5α-cholesta-8,14-dien-3β-ol in three steps (Id).

Delta (14)-sterol reductase (TM7F2; transmembrane 7 superfamily member 2, EC 1.3.1.70) catalyzes reactions on the three branches of the cholesterol and 24(S),25-epoxycholesterol pathways (Id).

Methylsterol monooxygenase 1 (MSM01; SC4MOL; C-4 methylsterol oxidase; EC 1.14.13.72) catalyzes demethylation of C4 methylsterols (Id).

Sterol-4-alpha-carboxylate 3-dehydrogenase, decarboxylating (NSDHL; NAD(P) dependent steroid dehydrogenase-like; EC 1.1.1.170) participates in several steps of post-squalene cholesterol and 24(S),25-epoxycholeseterol synthesis (Id).

3-keto-steroid reductase (HSD17B7; 17-beta-hydroxysteroid dehydrogenase 7; EC 1.1.1.270) converts zymosterone into zymosterol in the Bloch pathway (Id).

3-β-hydroxysteroid-Δ(8), Δ(7)-isomerase (EBP; emopamil-binding protein; EC5.3.3.5) catalyzes the conversion of Δ(8)-sterols into Δ(7)-sterols (Id).

Lathosterol oxidase (SC5DL; sterol-C5-desaturase (ERG3 Δ-5-desaturase homolog, S. cerevisiae-like; EC 1.14.21.6) catalyzes the production of 7-dehydrocholesterol, 7-dehydrodesmosterol and 24(S),25-epoxy-7-dehydrocholesterol (Id).

7-dehydrocholesterol reductase (DHCR7; EC 1.3.1.21) catalyzes reduction of the C7-C8 double bond of 7-dehydrocholesterol and formation of cholesterol, and produces desmosterol from 7-dehydrodesmosterol and 24(S),25-epoxycholesterol from 24(S),25-epoxy-7-dehydrocholesterol (Id).

Cytochrome P450, family 3, subfamily A, polypeptide 4 (CYP3A4; 1,8-cineole 2-exo-monooxygenase; taurochenodeoxycholate 6α-hydroxylase; EC 1.14.13.97)) catalyzes the hydroxylation of cholesterol leading to 25-hydroxycholesterol and 4β-hydroxycholesterol (Id).

Cholesterol 25-hydroxylase (CH25H; cholesterol 25-monooxygenase; EC 1.14.99.38) uses di-iron cofactors to catalyze the hydroxylation of cholesterol to produce 25-hydroxycholesterol, and has the capacity to catalyze the transition of 24-hydroxycholesterol to 24, 25-dihydroxycholesterol (Id).

Cytochrome P450, family 7, subfamily A, polypeptide 1 (CYP7A1; cholesterol 7-alpha-hydroxylase; EC 1.14.13.17) is responsible for introducing a hydrophilic moiety at position 7 of cholesterol to form 7α-hydroxycholesterol (Id).

Cytochrome P450, family 27, subfamily A, polypeptide 1 (CYP27A1; Sterol 27-hydroxylase; EC 1.14.13.15) catalyzes the transition of mitochondrial cholesterol to 27-hydroxycholesterol and 25-hydroxycholesterol (Id).

Cytochrome P450 46A1 (CYP46A1, cholesterol 24-hydroxylase, EC 1.14.13.98) catalyzes transformation of cholesterol into 24(S)-hydroxycholesterol (Id).

Statins

The term "statin" as used herein refers to a competitive inhibitor of HMG-CoA reductase in the mevalonate arm of the cholesterol biosynthesis pathway. Exemplary statins include, without limitation, mevastatin, lovastatin, simvastatin, and pravastatin, which are fungal metabolites, and fluvastatin, atorvastatin, and verivastatin, which are synthetic compounds. Statins exert their major effect—reduction of low density lipoprotein cholesterol levels—through a mevalonic acid-like moiety that competitively inhibits HMGCR by product inhibition. Higher doses of the more potent statins (e.g., atorvastatin and simvastatin) also can reduce triglyceride levels caused by elevated very low density lipoprotein levels (Goodman & Gilman's The Pharmacological Basis of Therapeutics, Ed. Joel G. Hardman, Lee E. Limbird, Eds., 10th Ed., McGraw Hill, New York (2001), p. 984).

HMG-CoA reductase inhibition by the statins cerivastatin and atorvastatin has been shown to have a biphasic dose-dependent effect on angiogenesis that is lipid independent and associated with alterations in endothelial apoptosis and VEGF signaling. (Weis, M. et al (2002) "Statins have biphasic effects on angiogenesis," Cir. Res. 105: 739-45). Endothelial cell proliferation, migration, and differentiation of an immortalized human dermal microvascular endothelial cell line (HMEC-1) in vitro were enhanced at low statin concentrations (0.005 to 0.01 μmol/L) but significantly inhibited at high statin concentrations (0.05 to 1 μmol/L). Antiangiogenic effects at high concentrations were associated with decreased endothelial release of VEGF and increased endothelial apoptosis and were reversed by geranylgeranyl pyrophosphate (GGP). GGP is required for the membrane localization of Rho family members. Other anti-angiogenic effects of statins may include inhibition of the expression or activity of monocyte chemoattractant protein-1, metalloproteinase and angiotensin-2, preproendothelin gene, and actin filament and focal adhesion formation. In a zebrafish anti-angiogenic drug screen, a number of statins (simvastatin, mevastatin, lovastatin, and rosuvastatin) were identified to inhibit angiogenesis in developing zebrafish embryos. The anti-angiogenic effect of rosuvastatin was confirmed in a mouse xenograft prostate cancer model.

(Wang, C. et al, (2010) "Rossuvastatin, identified from a zebrafish chemical genetic screen for anti-angiogenic compounds, suppresses the growth of prostate cancer," Eur. Urol. 58: 418-26). In other murine models, inflammation-induced angiogenesis was enhanced with low-dose statin therapy (0.5 mg/kg/d) but significantly inhibited with high concentrations of cerivastatin or atorvastatin (2.5 mg/kg/d). Despite the fact that high-dose statin treatment was effective at reducing lipid levels in hyperlipidemic apolipoprotein E-deficient mice, it impaired, rather than enhanced angiogenesis.

Prenylation

Prenylation is a class of lipid modification involving covalent addition of either farnesyl (15-carbon) or geranylgeranyl (20-carbon) isoprenoids to conserved cysteine residues at or near the C-terminus of proteins (Zhang, F. L. and Casey, P J (1996) "Protein Prenylation: Molecular Mechanisms and Functional Consequences," Ann. Rev. Biochem. 65: 241-69). Prenylation promotes membrane interactions of prenylated proteins, and plays a major role in several protein-protein interactions involving them.

Both the 15-carbon isoprenoid FPP and the 20-carbon isoprenoid GGP are products of the MVA metabolic pathway; it follows that regulation of HMGCR, FTase and GGTase-I, the key enzymes of the mevalonate pathway, can significantly affect the protein prenylation process. Zhang, F. L. and Casey, P J (1996) "Protein Prenylation: Molecular Mechanisms and Functional Consequences," Ann. Rev. Biochem. 65: 241-69).

Prenylated proteins can be grouped into two major classes: those containing the CAAX motif and the so-called CC- or CxC-containing proteins. CAAX proteins are defined as a group of proteins with a specific amino acid sequence at C-terminal that directs their post translational modification. Gao, J. et al (2009) "CAAX-box protein, prenylation process and carcinogenesis," Am. J. Trans. Res. 1(3): 312-25). C is cysteine residue, AA are two aliphatic residues, and X represents any C-terminal amino acid depending on different substrate specificity. The CAAX proteins encompass a wide variety of molecules that include nuclear lamins (intermediate filaments), Ras and a multitude of GTP-binding proteins (G proteins), and several protein kinases and phosphatases. Most CAAX proteins are found primarily at the cytoplasmic surface of cell membranes and are involved in a tremendous number of cellular signaling processes and regulatory events that play various roles in cell biological functions. These activities include cell proliferation, differentiation, nuclear stability, embryogenesis, spermatogenesis, metabolism, and apoptosis. The proteins that have a CAAX box at the end of the C-terminal always need a prenylation process before the proteins can be sent to plasma membrane or nuclear membrane and thereby exert their different functions.

Prenylation of CAAX proteins includes 3 steps: polyisoprenylation, proteolysis, and carboxyl methylation. Zhang, F. L. and Casey, P J (1996) "Protein Prenylation: Molecular Mechanisms and Functional Consequences," Ann. Rev. Biochem. 65: 241-69). First, an isoprenoid lipid is attached to the CAAX box by a prenyltransferase, for example, FTase or GGTase-I. When the C terminal amino acid "X" is serine, methionine or glutamine, proteins are recognized by FTase, whereas a leucine at this position results in modification by GGTase I. FTase and GGTase-I recognize the CAAX box in the protein, and then add the 15-carbon isoprenoid farnesyl pyrophosphate by FTase or the 20-carbon isoprenoid by GGTase-I to the cysteine residue of the CAAX box. Second, following prenylation, the aaX residues are cleaved by an endoprotease. Third, the carboxyl group of the modified cysteine is methylated by a specific methyl transferase.

GGTase II transfers geranylgeranyl groups from GGPP to both cysteine residues of CC- or CxC-containing proteins in a process mechanistically distinct from that of CAAX proteins. Additionally, proteins containing the CxC motif are methylated at the C-terminal prenylcysteine, whereas CC-containing proteins are not.

HMGCR mediated GGPP biosynthesis regulates Cdc42 prenylation. (Eisa-Beygi S, Hatch G, Noble S, Ekker M, Moon T W (2013) "The 3-hydroxy-3-methylglutaryl-CoA reductase (HMGCR) pathway regulates developmental cerebral-vascular stability via prenylation-dependent signaling pathway," Dev Biol 373:258-266). Cdc42 regulates adherens junction stability and endothelial barrier function.

Intracerebral Hemorrhage (ICH)

Spontaneous intracerebral hemorrhage (ICH) is a severe and debilitating form of stroke that is most commonly due to hypertension, amyloid angiopathy, brain vascular malformations or secondary to medications including antiplatelet and anticoagulant drugs. Spontaneous ICH comprises 10% of strokes and is associated with death or disability in more than 50% of the approximately 90,000 patients affected each year in North America. (Roger V L, Go A S, Lloyd-Jones D M, Adams R J, Berry J D, Brown T M, et al (2011) "Heart disease and stroke statistics—2011 update: a report from the American Heart Association," Circulation 123:e18-e209). Clinical studies also have disclosed a link between cholesterol-lowering HMGCR inhibitors (statins) and increased risk of ICH. (Collins R, Armitage J, Parish S, Sleight P, Peto R: (2004) "Effects of cholesterol-lowering with simvastatin on stroke and other major vascular events in 20536 people with cerebrovascular disease or other high-risk conditions," Lancet 363:757-767); Flaster M, Morales-Vidal S, Schneck M J, Biller J (2011) "Statins in hemorrhagic stroke," Expert Rev Neurother 11:1141-1149; Goldstein L B, Amarenco P, Szarek M, Callahan A, III, Hennerici M, Sillesen H, et al (2008) "Hemorrhagic stroke in the Stroke Prevention by Aggressive Reduction in Cholesterol Levels study," Neurology 70:2364-2370). Another type of brain hemorrhage is brain microhemorrhages (BMH), which are small, usually multiple, ICHs. A systematic review found that 5% of healthy adults, 34% of patients with ischemic stroke and 60% of patients with nontraumatic ICH had BMH. (Cordonnier C, Klijn C J, van B J, Al-Shahi S R (2010) "Radiological investigation of spontaneous intracerebral hemorrhage: systematic review and trinational survey," Stroke 41:685-690). They are more common in patients with hypertension and diabetes mellitus. Other than treatment of hypertension, there is no prophylactic treatment to prevent ICH or BMH.

1. Intracerebral Hemorrhage, Brain Microhemorrhages and other Causes of Intracerebral Hemorrhage Spontaneous ICH accounts for 10% of strokes. There are about 90,000 per year in the U.S. and Canada. Mortality is 30-50%. The most common cause is hypertension, and ICH due to hypertension can be partly reduced by treating hypertension. However, other factors contribute to ICH from hypertension, such as low serum cholesterol (Sutherland G R, Auer R N (2006) "Primary intracerebral hemorrhage," J Clin Neurosci 13:511-517). The second main cause of ICH is amyloid angiopathy, for which there is no specific treatment. The pathophysiology of ICH from amyloid blood vessels is unknown, although it is highly associated with amyloid deposition in brain arteries and arterioles.

Brain microhemorrhages (BMH) are another form of ICH (Fisher M J (2013) "Brain regulation of thrombosis and hemostasis: from theory to practice," Stroke 44:3275-3285). They are associated with increasing age, amyloid angiopathy, hypertension, ischemic/hemorrhagic stroke (mixed cerebrovascular disease) and Alzheimer disease. They are usually attributed to localized bleeding from tears in small arterioles but Fisher proposed that they may be age-dependent, inflammation-mediated leakage from small brain blood vessels (Id). This hypothesis is supported by BMH induced by lipopolysaccharide (LPS) in zebrafish and mice (FIGS. 5, 6 and 9) (Liu S, Vasilevko V, Cribbs D H, Fisher M (2013) "A mouse model of cerebral microhemorrhages," Stroke 44:AWP297 (Abstract)). Furthermore, patients with BMH are at increased risk of ICH and that risk is increased further if they take antiplatelet or anticoagulant drugs (Cordonnier C, Klijn C J, van B J, Al-Shahi S R (2010) "Radiological investigation of spontaneous intracerebral hemorrhage: systematic review and trinational survey," Stroke 41:685-690; Greenberg S M, Eng J A, Ning M, Smith E E, Rosand J (2004) "Hemorrhage burden predicts recurrent intracerebral hemorrhage after lobar hemorrhage," Stroke 35:1415-1420; Imaizumi T, Horita Y, Hashimoto Y, Niwa J (2004) "Dotlike hemosiderin spots on T2*—Weighted magnetic resonance imaging as a predictor of stroke recurrence: a prospective study," J Neurosurg 101:915-920). BMHs also are associated with cognitive impairment (Yakushiji Y, Noguchi T, Hara M, Nishihara M, Eriguchi M, Nanri Y, et al (2012) "Distributional impact of brain microhemorrhages on global cognitive function in adults without neurological disorder," Stroke 43:1800-1805).

While statins reduce the long-term risk of myocardial infarction and ischemic stroke, they increase the risk of ICH (Collins R, Armitage J, Parish S, Sleight P, Peto R (2004) "Effects of cholesterol-lowering with simvastatin on stroke and other major vascular events in 20536 people with cerebrovascular disease or other high-risk conditions," Lancet 363:757-767; Flaster M, Morales-Vidal S, Schneck M J, Biller J (2011) "Statins in hemorrhagic stroke," Expert Rev Neurother 11:1141-1149; Goldstein L B, Amarenco P, Szarek M, Callahan A, III, Hennerici M, Sillesen H, et al (2008) "Hemorrhagic stroke in the Stroke Prevention by Aggressive Reduction in Cholesterol Levels study," Neurology 70:2364-2370, Haussen D C, Henninger N, Kumar S, Selim M (2012) "Statin use and microhemorrhages in patients with spontaneous intracerebral hemorrhage," Stroke 43:2677-2681); Eisa-Beygi S, Wen X Y, Macdonald R L. (2014) "A Call for Rigorous Study of Statins in Resolution of Cerebral Cavernous Malformation Pathology." Stroke 45(6):1859-61. According to the American Heart Association guidelines, statins may not be indicated in these patients. (Morgenstem L B, Hemphill J C, III, Anderson C, Becker K, Broderick J P, Connolly E S, Jr., et al (2010) "Guidelines for the management of spontaneous intracerebral hemorrhage: a guideline for healthcare professionals from the American Heart Association/American Stroke Association," Stroke 41:2108-2129). Statins inhibit cholesterol synthesis, and low serum cholesterol also is an independent risk factor for ICH. (Sutherland G R, Auer R N (2006) "Primary intracerebral hemorrhage," J Clin Neurosci 13:511-517).

Cerebral cavernous malformations (CCM) are the most common brain vascular malformation. They are found in 0.5% of the population and are a cause of spontaneous ICH (Richardson B T, Dibble C F, Borikova A L, Johnson G L (2013) "Cerebral cavernous malformation is a vascular disease associated with activated RhoA signaling," Biol Chem 394:35-42). The hemorrhages tend to cluster in time so a drug that reduced this risk during times of increased hemorrhage risk is actively being sought and is greatly needed (Barker F G, Amin-Hanjani S, Butler W E, Lyons S, Ojemann R G, Chapman P H, et al (2001) "Temporal clustering of hemorrhages from untreated cavernous malformations of the central nervous system," Neurosurgery 49:15-24, Li Q, Mattingly R R (2008) "Restoration of E-cadherin cell-cell junctions requires both expression of E-cadherin and suppression of ERK MAP kinase activation in Ras-transformed breast epithelial cells," Neoplasia 10:1444-1458). CCM may be sporadic or inherited in association with loss-of-function mutations in genes encoding 3 structurally distinct proteins, CCM1 (KRIT1), CCM2 (Osmosensing scaffold for MEKK3 or OSM, MALCAVERIN, or MGC4607), and CCM3 (programmed cell death 10 (PDCD10)(Li D Y, Whitehead K J (2010) "Evaluating strategies for the treatment of cerebral cavernous malformations," Stroke 41:S92-S94). All 3 CCM proteins are involved in cytoskeleton and AJ and the mutations have to be in endothelial cells in order for CCMs to form. Mutations in CCM1 and CCM2 lead to increased RhoA activity, which led to the hypothesis that increased RhoA activity affects the cell cytoskeleton and causes vascular instability, CCMs and possibly ICH/BMH in humans. Drugs that inhibit RhoA activity, such as statins and fasudil, are theorized to reduce the risk of ICH based on data from mouse models of CCMs. (Li D Y, Whitehead K J (2010) "Evaluating strategies for the treatment of cerebral cavernous malformations," Stroke 41:S92-S94; Richardson B T, Dibble C F, Borikova A L, Johnson G L (2013) "Cerebral cavernous malformation is a vascular disease associated with activated RhoA signaling," Biol Chem 394:35-42). This hypothesis is in contrast to studies in zebrafish showing that statins impair vascular stability and give rise to ICH/BMH (Eisa-Beygi S, Hatch G, Noble S, Ekker M, Moon T W (2013) "The 3-hydroxy-3-methylglutaryl-CoA reductase (HMGCR) pathway regulates developmental cerebral-vascular stability via prenylation-dependent signaling pathway," Dev Biol 373:258-266). These effects were shown to be due to defective prenylation of Rho GTPases, particularly Cdc42, a Rho GTPase involved in the regulation of vascular stability, leading to the question as to the cause of the discrepancy between zebrafish and mouse models. In fact, statin treatment of zebrafish induces cerebrovascular defects typified by leaky, dilated cranial vessels with sluggish blood flow, which are analogous to CCMs. Without being limited by theory, it is hypothesized herein that the difference is due to relative degrees of inhibition of RhoA and Cdc42, since the balance of vascular destabilizing RhoA to vascular stabilizing Cdc42 may differ depending on dose and species.

2. Models of ICH and BMH

Zebrafish are emerging as useful model organism for large-scale, phenotype-based chemical and genetic screening. Zebrafish are genetically very similar to humans, easy and fast to breed for high-throughput screening, transparent early on for easy imaging and relatively easy to modify genetically. Some compounds discovered in zebrafish are effective in mammals and already in human studies (Peterson R T, Fishman M C (2011) "Designing zebrafish chemical screens," Methods Cell Biol 105:525-541). Since the screening is performed in vivo, general drug toxicity can be evaluated at the same time as drug efficacy, allowing for a higher success rate as compared to an in vitro drug screens on cultured cells (Miscevic F, Rotstein O, Wen X Y (2012) "Advances in zebrafish high content and high throughput technologies," Comb Chem High Throughput Screen 15:515-521, 2012). Furthermore, an in vivo screen system such as zebrafish can measure the efficacy of the drug as well as its metabolites. The ability to perform high throughput screening of compound libraries in zebrafish is an advantage over testing compounds in rodents where high throughput screening is not possible.

Several models of ICH/BMH have been identified in zebrafish. First, statins cause ICH/BMH in zebrafish (FIG. 7, 9) (Eisa-Beygi S, Hatch G, Noble S, Ekker M, Moon T W (2013) "The 3-hydroxy-3-methylglutaryl-CoA reductase (HMGCR) pathway regulates developmental cerebral-vascular stability via prenylation-dependent signaling pathway," Dev Biol 373:258-266). The mechanism is due to inhibition of protein prenylation since ICH/BMH can also be induced by MO-induced depletion of the β subunit of geranylgeranyltransferase 1 (GGTase 1, pggtlβ) and prevented by downstream metabolic rescue with the product of HMGCR, geranylgeranyl pyrophosphate (GGPP, FIGS. 3, 4 and 8). GGPP is a 20 carbon lipid molecule required for post-translational prenylation of Rho GTPase proteins. The BMH temporal and spatial distribution is similar to ICH/BMH seen in zebrafish bubblehead (bbhm292) and redhead (rhdmi149) mutants. (Buchner D A, Su F, Yamaoka J S, Kamei M, Shavit J A, Barthel L K, et al (2007) "pak2a mutations cause cerebral hemorrhage in redhead zebrafish," Proc Natl Acad Sci USA 104:13996-14001; Butler M G, Gore A V, Weinstein B M (2011) "Zebrafish as a model for hemorrhagic stroke," Methods Cell Biol 105:137-161; Liu J, Fraser S D, Faloon P W, Rollins E L, Vom B J, Starovic-Subota O, et al (2007) "A betaPix Pak2a signaling pathway regulates cerebral vascular stability in zebrafish," Proc Natl Acad Sci USA 104:13990-13995).

Bubblehead ($bbh^{m292}$) develops ICH and brain edema 36 to 52 hours postfertilization (hpf) whereas redhead ($rhd^{mi149}$) develops ICH 2 to 3 days postfertilization. The $bbh^{m292}$ mutation is in the βpix (pak-interacting exchange factor β) gene, whereas the $rhd^{mi149}$ mutation is in pak2a (p21 protein [Cdc42/Rac]-activated kinase 2a) gene. These genes encode proteins that regulate activity of Rho GTPases, Rac and Cdc42. That both of these changes are associated with ICH/BMH is consistent with Rac and Cdc42 requiring GGTase 1-mediated prenylation. GGTase 1 post-translationally modifies Rac and Cdc42 by adding a mevalonate-derived GGPP which is required to activate these GTPases. (Peterson Y K, Kelly P, Weinbaum C A, Casey P J (2006) "A novel protein geranylgeranyltransferase-I inhibitor with high potency, selectivity, and cellular activity," J Biol Chem 281:12445-12450) There are also zebrafish mutants corresponding to the orthologous human CCM1, CCM2 and CCM3 genes (Butler M G, Gore A V, Weinstein B M (2011) "Zebrafish as a model for hemorrhagic stroke," Methods Cell Biol 105:137-161). These develop cardiac dilation and progressively enlarged, dilated blood vessels and it has been suggested the genes have similar function in both species. No ICH phenotype is described in these zebrafish mutants but combined MO-induced reduction in a Ras GTPase effector protein, rap 1b and zebrafish ccm1 did cause ICH (Gore A V, Lampugnani M G, Dye L, Dejana E, Weinstein B M (2008) "Combinatorial interaction between CCM pathway genes precipitates hemorrhagic stroke," Dis Model Mech 1:275-281). In mice, the gene defects for CCMs are suggested to be required in endothelial cells in order for malformations to develop (Chan A C, Li D Y, Berg M J, Whitehead K J (2010) "Recent insights into cerebral cavernous malformations: animal models of CCM and the human phenotype," FEBS J 277:1076-1083).

Mouse models of ICH include direct injection of blood into the brain, or injection of elastase, which degrades vascular collagen and causes bleeding. These models would not be useful for detecting therapeutic agents that stabilize the vasculature. There are two models of spontaneous ICH in mice. One is a model of acute and chronic hypertension induced by a combination of angiotensin 2 and NOS inhibition in mice (Wakisaka Y, Chu Y, Miller J D, Rosenberg G A, Heistad D D (2010) "Spontaneous intracerebral hemorrhage during acute and chronic hypertension in mice,". J Cereb Blood Flow Metab 30:56-69). The mechanism of ICH in hypertension, however, may differ from what we are investigating with statins and CCM genes.

A second model of BMH involves transgenic mice (e.g. Tg2576) that spontaneously overexpress P-amyloid, mimicking cerebral amyloid angiopathy (Herzig M C, Winkler D T, Burgermeister P, Pfeifer M, Kohler E, Schmidt S D, et al. Abeta is targeted to the vasculature in a mouse model of hereditary cerebral hemorrhage with amyloidosis. Nat Neurosci. 2004; 7(9):954-60., Fisher M, Vasilevko V, Passos G F, Ventura C, Quiring D, Cribbs D H. Therapeutic modulation of cerebral microhemorrhage in a mouse model of cerebral amyloid angiopathy. Stroke. 2011; 42(11):3300-3). There are other similar models. (Alharbi B M, Tso M K, Macdonald R L. (2016) Animal models of spontaneous intracerebral hemorrhage. Neurol Res 38:448-455). The limitation is that it takes up to 2 years for animals to develop BMH.

LPS has been used to induce BMH in mice (Tang, A T, et al, "Endothelial TLR4 and the microbiome drive cerebral cavernous malformations," Nature (2017) 545 (7654): 305-310. Doi: 10.1038/nature22075; Liu S, Vasilevko V, Cribbs D H, Fisher M (2013) "A mouse model of cerebral," Stroke 44:AWP297 [Abstract]); Liu S, Grigoryan M M, Vasilevko V, Sumbria R K, Paganini-Hill A, Cribbs D H, et al. (2014) "Comparative analysis of H & E and prussian blue staining in a mouse model of cerebral microbleeds." J Histochem Cytochem. 62:767-773). LPS or vehicle (phosphate buffered saline [PBS]) was injected at baseline and again at 24 hours, and the mice were sacrificed 2 days after the first injection (FIGS. 6 and 9). When the brains were examined, multiple small fresh hemorrhages were found in mice treated with LPS, as was increased blood brain barrier permeability. It has been suggested that this model might be useful to study mechanisms of and interventions for BMH.

Anti-β3 Integrin Mouse Model of Intracerebral Hemorrhage (ICH)

The integrin αIIbβ3 is the most abundant glycoprotein on platelets. The β3 subunit also is coexpressed with the αV subunit (i.e., αVβ3) on proliferating endothelial cells (ECs) during angiogenesis (Yougbare, I. et al., "Maternal anti-platelet β3 integrins impair angiogenesis and cause intracranial hemorrhage," (2015) J. Clin. Invest. 125(4): 1545-56 citing Brooks, P C et al, "Requirement of vascular integrin alpha v beta 3 for angiogenesis," Science (1994) 264 (5158): 569-71; Brooks, P C et al, "Integrin αvβ3 antagonists promote tumor regression by inducing apoptosis of angiogenic blood vessels," (1994) Cell 79(7): 1157-64; Di Q, et al., "Impaired cross-activation of β3 integrin and VEGFR-2 on endothelial progenitor cells with aging decrases angiogenesis in response to hypoxia," Intl J. Cardiol. (2013) 168(3): 2167-76; Stupack, D C, Cheresh, D A, "Integrins and angiogenesis," Curr. Top. Dev. Bio. (2004) 64: 207-38. Several studies have demonstrated that β3 plays an important role in angiogenesis. For example, it has been shown that αVb3 was required for angiogenesis (Id. citing Brooks, P C et al, "Requirement of vascular integrin alpha v beta 3 for angiogenesis," Science (1994) 264 (5158): 569-71), and that αVb3 antagonists promoted tumor regression by inducing apoptosis of angiogenic blood vessels (Id. citing Brooks, P C et al, "Integrin αvβ3 antagonists promote tumor regression by inducing apoptosis of angiogenic blood vessels," (1994) Cell 79(7): 1157-64). Evidence has also shown that integrin αVβ3 cooperated with VEGFR2 in pro-angiogenic signaling (Id., citing Robinson, S D, et al, "αvβ3 integrin limits the contribution of neuropilin-1 to vascular endothelial growth factor-induced angiogenesis," J. Biol. Chem. (2009) 284(49): 33966-81; Soldi, R. et all, "Role of αvβ3 integrin in the activation of vascular endothelial growth factor receptor-2," EMBO J. (1999) 18(4): 882-92) and that AKT phasphorylation was essential in VEGF-mediated post-natal angiogenesis (Id. citing Kitamura, T et al, "Regulation of VEGF-mediated angiogenesis by the Akt/PKB substrate Girdin," Nat. Cell Biol. (2008): 10(3): 329-337).

An established murine model of fetal and neonatal autoimmune thrombocytopenia (FNAIT) has been used to investigate the mechanism of ICH in affected fetuses and neonates (Id., citing Chen, P. et al., "Animal model of fetal and neonatal immune thrombocytopenia: role of neonatal Fc receptor in the pathogenesis and therapy," Blood (2010) 116 (18): 3660-68; Li, C. et al,"The maternal immune response to fetal platelet GpIbα causes frequent miscarriage in mice that can be prevented by intravenous IgG and anti-FcRn therapies," J. Clin. Invest. (2011) 121(11): 4537-47; Ni H, et al, "A novel murine model of fetal and neonatal alloimmune thrombocytopenia: respons to intravenous IgG therapy," Blood (2006) 107(7): 2976-83). Itgb3$^{-/-}$ and Gp1ba$^{-/-}$ mice (referred to hereinafter as β3$^{-/-}$ and GPIbα$^{-/-}$) were transfused with WT platelets to mimic exposure to β3 or to GPIbα during conception. Id. Anti-β3 or anti-GPIbα antibodies were detected; these immunized mice were subsequently bred with WT males. Id. Similar severity of thrombocytopenia in the heterozygote (−/+) neonates delivered from immunized β3$^{-/-}$ and GPIBα$^{-/-}$ mice was found. Id. ICH was found in the β3$^{-/-}$ fetuses starting around EC15.5 as well as in neonates using a high-frequency ultrasound imaging system to detect in utero ICH in pregnant mice, and performing H & E staining of brain sections. Id. Hemorrhage was observed in different areas of the brain, and the frequency of ICH increased in fetuses in accordance with the number of material immunizations. Id. ICH was never found in anti-GPIbα-mediated FNAIT fetuses or neonates. Id.

The following experiments showed that anti-β3 antibodies, but not anti-GPIbα antibodies or thrombocytopenia alone, were the cause of ICH. To confirm that ICH was indeed antibody mediated, β3$^{-/-}$ and GPIBα$^{-/-}$ neonates delivered from naïve mice were passively injected with antisera at P2. Postnatal injection of anti-33 sera into β3$^{-/-}$ neonates induced ICH, but anti-GPIbα sera did not induce any ICH in GPIBα$^{-/-}$ neonates (P<0.01). Id. To further determine whether platelet-mediate cytotoxicity (Id. Citing Nieswandt, B. et al., "Identification of critical antigen-specific mechanisms in the development of immune thrombocytopenic purpura in mice," Blood (2000) 96(7): 2520-27; Nieswandt, B. et al, "Targeting of platelet integrin αIIbβ3 determines systemic reaction and bleeding in murine thrombocytopenia regulated by activating and inhibitory FcγR," Intl Immunol. (2003) 15(3): 341-49) might be involved in the mechanism of ICH, anti-β3 sera were injected into αIIb integrin-deficient pups that did not express αIIbβ3 integrin on their platelets. Id. ICH was observed in Itga2b$^{-/-}$ pups with normal platelet counts, and postnatal injection of anti-β3 sera into β3$^{-/-}$ neonates failed to induce ICH and impair retinal vascular development in these antigen-negative pups. Id.

Mouse models that combine Ccm heterozygotes on a background of homozygous deletion of the mismatch repair complex protein Msh2 (<Ccm1$^{+/-}$Msh$^{-/-}$ and Ccm2+/ 'Msh$^{-/-}$) develop CCMs. (McDonald D A, Shi C, Shenkar R, Stockton R A, Liu F, Ginsberg M H, et al, (2012) "Fasudil decreases lesion burden in a murine model of cerebral cavernous malformation disease," Stroke 43:571-574. Another important gene is Rap1b, mouse mutants of which develop normally until embryonic day 12.5, at which point 50% die due to hemorrhage (Id); Chrzanowska-Wodnicka M (2013) "Distinct functions for Rap1 signaling in vascular morphogenesis and dysfunction," Exp Cell Res 319:2350-2359). Subphenotypic levels of reduction of ccm1 and rap1b in zebrafish cause brain hemorrhage.

3. Mechanisms of ICH and BMH

In patients with hypertension, the cause of ICH is arteriolosclerosis of the small penetrating arteries that tend to arise from large conducting cerebral arteries. (Auer, R N, Sutherland, G R (2005) "Primary intracerebral hemorrhage: pathophysiology," Can. J. Neurol. Sci. 32 Suppl. 2: 3-12). The only currently available treatment is prophylactic treatment of hypertension. Guidelines for management of patients once they have a hypertensive ICH are published, and recommend surgical evacuation of space-occupying cerebellar ICH and general medical supportive care. (Hemphill J C, 3rd, Greenberg S M, Anderson C S, Becker K, Bendok B R, Cushman M, et al. Guidelines for the management of spontaneous intracerebral hemorrhage: A guideline for healthcare professionals from the American Heart Association/American Stroke Association. Stroke. 2015; 46:2032-2060).

There are different theories as to why statins increase the risk of ICH. For example, statin-associated ICH and other types of ICH/BMH may be due to defects in the HMGCR pathway (Eisa-Beygi S, Hatch G, Noble S, Ekker M, Moon T W (2013) "The 3-hydroxy-3-methylglutaryl-CoA reductase (HMGCR) pathway regulates developmental cerebral-vascular stability via prenylation-dependent signaling pathway," Dev Biol 373:258-266). Inhibition of HMGCR or of other downstream molecules such as geranylgeranyltransferase 1 (GGTase 1) causes ICH/BMH in zebrafish embryos (Id). Flaster and colleagues suggested that statins could cause changes in platelets or in the interactions between clotting and fibrinolytic cascades that could promote ICH, although there is no evidence for this thus far (Flaster M, Morales-Vidal S, Schneck M J, Biller J (2011) "Statins in hemorrhagic stroke," Expert Rev Neurother 11:1141-1149).

There are at least 2 mutations that cause ICH in zebrafish. Bubblehead is a loss of function mutation of βpix (p isoform of the p21-activating kinase (Pak)-interacting exchange factor) (Liu J, Zeng L, Kennedy R M, Gruenig N M, Childs S J (2012) "betaPix plays a dual role in cerebral vascular stability and angiogenesis, and interacts with integrin alphavbeta8," Dev Biol 363:95-105). βpix regulates vascular stability and βpix mutation is the cause of vascular fragility and ICH in the bbh$^{m292}$ mutant. (Liu J, Fraser S D, Faloon P W, Rollins E L, Vom B J, Starovic-Subota O, et al (2007) "A betaPix Pak2a signaling pathway regulates cerebral vascular stability in zebrafish," Proc Natl Acad Sci USA 104:13990-13995). βpix also is involved in focal adhesion complexes, which contain integrins and cadherins (Frank S R, Hansen S H (2008) "The PIX-GIT complex: a G protein signaling cassette in control of cell shape," Semin Cell Dev Biol 19:234-244). Another zebrafish mutant, redhead, is rhd$^{mi149}$ that has a mutation pak2a (p21 protein [Cdc42/Rac]-activated kinase 2a) Liu J, Fraser S D, Faloon P W, Rollins E L, Vom B J, Starovic-Subota O, et al (2007) "A betaPix Pak2a signaling pathway regulates cerebral vascular stability in zebrafish," Proc Natl Acad Sci USA 104:13990-13995). pak2a is a kinase acting downstream of Cdc42 and Rac, and may be involved in a complex with βPix, paxillin and GIT1. Since Cdc42 also is required for interaction of VE-cadherin and the actin cytoskeleton, the defect in the bbh$^{m292}$ mutant could also be due to defects in this latter interaction. In mice, germ-line or endothelial cell specific Pak2 knockout is embryonic lethal likely due to impaired blood vessel formation. (Radu M, Semenova G, Kosoff R, Chernoff J (2014) "PAK signalling during the development and progression of cancer," Nat Rev Cancer 14:13-25). Both are transmembrane proteins that connect the intracellular cytoskeleton to the extracellular matrix (Frank S R, Hansen S H (2008) "The PIX-GIT complex: a G protein signaling cassette in control of cell shape," Semin Cell Dev Biol 19:234-244; van der Flier A, Sonnenberg A (2001) "Function and interactions of integrins," Cell Tissue Res 305:285-298). They are important in angiogenesis and vascular stability. For example, homozygous integrin $α_v$ or $β_8$ null mice die perinatally or before from ICH (Zhu J, Motejlek K, Wang D, Zang K, Schmidt A, Reichardt L F (2002) "$β_8$ integrins are required for vascular morphogenesis in mouse embryos," Development 129:2891-2903). Targeted inactivation of VE-cadherin and truncation of the β-catenin-binding cytosolic domain of VE-cadherin in mice induces endothelial cell-specific apoptosis, in addition to defective remodeling and maturation of the vasculature and early lethality (Carmeliet P, Lampugnani M G, Moons L, Breviario F, Compernolle V, Bono F, et al (1999) "Targeted deficiency or cytosolic truncation of the VE-cadherin gene in mice impairs VEGF-mediated endothelial survival and angiogenesis," Cell 98:147-157). Most recently, we demonstrated that by delivering anti-$β_3$ integrin antibody into pregnant mice could induce ICH in mouse embryos and neonatal mice. (Yougbaré, I, Lang S, Yang H, Chen P, Zhao X, Tai W S, Zdravic D, Vadasz B, Li C, Piran S, Marshall A, Zhu G, Tiller H, Killie M K, Boyd S, Leong-Poi H, Wen X Y, Skogen B, Adamson S L, Freedman J and Ni H (2015) "Maternal anti-platelet β3 integrin antibodies impair angiogenesis and cause intracranial hemorrhage in fetal and neonatal alloimmune thrombocytopenia," J. Clinical Investigation (JCI), 125:1545-56). Morpholino-induced reduction of cdh5, the zebrafish homologue of the VE-cadherin gene in humans, causes vascular instability, defective lumen formation and ICH by 48 hpf (Montero-Balaguer M, Swirsding K, Orsenigo F, Cotelli F, Mione M, Dejana E (2009) "Stable vascular connections and remodeling require full expression of VE-cadherin in zebrafish embryos," PLoS ONE 4:e5772). It is known that integrins are linked to βPix in focal adhesions by proteins including G protein-coupled receptor kinase interacting target (GIT1), which is an Arf GTPase activating protein (GAP) (Liu J, Zeng L, Kennedy R M, Gruenig N M, Childs S J (2012) "betaPix plays a dual role in cerebral vascular stability and angiogenesis, and interacts with integrin alphavbeta8," Dev Biol 363:95-105). Mice without GIT1 have increased pulmonary vascular density and pulmonary hemorrhage. In zebrafish GIT1 is initially ubiquitously expressed but it becomes restricted to the head by 48 hpf. Knock down of GIT1 expression with MOs causes increases in ICH. Liu, et al., conducted a series of experiments in zebrafish that suggest that βPix interacts with $α_v$ and $β_8$ integrins and GIT 1 to stabilize the cerebral vasculature, and inhibiting expression of any of the components causes ICH (Liu J, Zeng L, Kennedy R M, Gruenig N M, Childs S J (2012) "betaPix plays a dual role in cerebral vascular stability and angiogenesis, and interacts with integrin alphavbeta8," Dev Biol 363:95-105).

CCM1, 2 and 3 may form a multiprotein complex that also includes integrin β1-binding protein (ICAP-1), the GTPases Rac and Rap1 and MAPK kinase kinase MEKX3 Chrzanowska-Wodnicka M (2013) "Distinct functions for Rap1 signaling in vascular morphogenesis and dysfunction," Exp Cell Res 319:2350-2359; Liu J, Fraser S D, Faloon P W, Rollins E L, Vom B J, Starovic-Subota O, et al (2007) "A betaPix Pak2a signaling pathway regulates cerebral vascular stability in zebrafish. Proc Natl Acad Sci USA 104:13990-13995). This complex modulates adherens junctions by interacting with β catenin and VE-cadherin mainly in endothelial cells (but probably other perivascular cells) and achieving vascular stability. Effects of knockouts of the ccm genes in zebrafish and mice are not fully explored but show that embryonic germ-line knockouts tend not to resemble the human phenotype, although in some cases, conditional, endothelial cell specific knockouts do. In zebrafish, knockdown of rap1b leads to ICH, but also sub-phenotype levels of reduction in rap1b combined with ccm1 leads to ICH.

It is likely that the cellular localization and other factors influence the effect of GTPase signaling on vascular stability and ICH/BMH because in mice with mutations in germ-line or endothelial cell-specific mutations in CCM2, statin inhibition of HMGCR, which reduces Rho GTPase prenylation, improves endothelial integrity and prevents the increased vascular permeability. In zebrafish, however, inhibition of HMGCR with statins or mutation and MO-induced loss of function of proteins that activate Rho GTPase signaling increase vascular permeability (Liu J, Fraser S D, Faloon P W, Rollins E L, Vom B J, Starovic-Subota O, et al (2007) "A betaPix Pak2a signaling pathway regulates cerebral vascular stability in zebrafish," Proc Natl Acad Sci USA 104:13990-13995). The discrepancy is likely due to cell-specific effects, age of the organisms, species differences, differential effects on RhoA and cdc42 (that tend to have opposing effects, RhoA destabilizing cdc42 stabilizing vasculature) or differences between wild-type and CCM2 animals.

Statement of the Problem

Intracerebral hemorrhage, BMH and cavernous malformations share common elements of vascular instability in blood vessels in the brain that lead to intracranial hemorrhage, to brain injury and to death and disability. Intracerebral hemorrhage is the most lethal and devastating type of stroke. There is no pharmacologic treatment available to reduce this and there is a high unmet medical need. Therefore, a need exists for a pharmaceutical composition comprising a therapeutic amount of a vascular stabilizing agent, in some embodiments formulated as a sustained release preparation, that when administered, is effective to prevent or reduce the incidence ICH, BMH and ICH from various causes including brain cavernous malformations.

SUMMARY OF THE INVENTION

According to one aspect, the described invention provides a method for reducing incidence of vascular leakage comprising administering a pharmaceutical composition containing a small molecule therapeutic compound, a therapeutic amount of which is effective to reduce incidence of bleeding in the brain by at least 30% relative to a control.

According to one embodiment, the small molecule therapeutic compound is selected from the group consisting of artemether or a derivative of artemether. According to another embodiment, the derivative of artemisinin is dihydroartemisinin, artemesinin, or artesunate. According to another embodiment, the small molecule therapeutic compound is selected from the group consisting of benidipine, lacidipine, ethynylestradiol or triptolide.

According to one embodiment, the vascular leakage is induced by a statin, by a lipopolysaccharide, or both. According to another embodiment, the statin is atorvastatin.

According to one embodiment, the vascular leakage is a spontaneous intracerebral hemorrhage. According to another embodiment, the spontaneous intracerebral hemorrhage occurs in association with a mutation of one or more genes selected from beta-pix, Pak2a, cdh5, ccm1, ccm2, ccm3, Rap1b, Pggt1b, Hmgcrb, and beta3 integrin.

According to one embodiment, the vascular leakage includes a brain microhemorrhage. According to another embodiment, the brain microhemorrhage occurs in association with administration of a statin.

According to one embodiment, the vascular leakage comprises a brain vascular malformation. According to another embodiment, the brain vascular malformation is a cerebral cavernous malformation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 shows examples of results from drug efficacy assays in the zebrafish bbh model for two compounds, ART, artesunate; and ARM, artemether. Results are plotted as percent hemorrhage (y-axis) vs. log (drug nmol/L); n=30 larvae per condition.

FIG. 5 shows examples of results from drug efficacy assays in zebrafish hmgcrb morphants using artesunate (ART), and artemether (ARM). Results are plotted as percent hemorrhage (y-axis) vs. log (drug nmol/L); n=15-20 larvae per condition.

FIG. 8 shows that artemether (ARM) rescues LPS-induced brain microbleeds in mice. Panel A shows data from a stereomicroscope count of surface microbleeds in brains from LPS treated mice (n=8) or LPS+ artemether-treated mice (n=8). The left panel shows representative images from each of the two groups; arrows indicate microbleeds. The right panel shows a statistical analysis (*P<0.05, two-tailed t-test with Welch correction); data is expressed as mean±SD. As compared to LPS treated animals, brains from ARM treated mice showed a robust reduction in total surface microbleeds. Panel B shows data from quantification of microbleeds on brain slices stained by hematoxylin and eosin. The left panel shows representative images of stained brain slices from each of the two groups; the arrows indicate microbleeds on the slices; the right panel chart shows a statistical analysis of microbleeds count (**P<0.01, unpaired two-tailed t-test with Welch's correction). Data is expressed as mean±SD, n=8 for both LPS treated and LPS+ARM treated groups. Similar to the surface microbleed counts, ARM treatment significantly reduced the total number of microbleeds inside the mouse brains.

FIG. 13 shows the HMGCR molecular pathway that leads to vascular stability in zebrafish. Panels A & B: Schematics illustrating stable EC junctions are maintained by a Cdc42-dependent and VE-cadherin-mediated cell-cell adhesion. Panel C shows that splice-inducing morpholinos designed against cdh5 induced intracerebral hemorrhage in zebrafish at 36-48 hpf (lateral images are shown).

FIG. 15 shows that LPS induces brain hemorrhage in developing zebrafish embryo and artemether have protective effects on LPS-induced mortality. (A) Survival curves of developing zebrafish embryos when LPS is delivered in fish water at 24 hours post fertilization (hpf). (B) shows that artemether in fish water had a protective effect on fish survival. (C) shows that LPS treatment of 24 hpf embryos resulted in 52% of embryos (n=120) with brain hemorrhage (arrow points to hemorrhage). (D) Bar graph representing percent (%) cerebral hemorrhage in (C).

DETAILED DESCRIPTION OF THE INVENTION

Glossary

Figure 1:
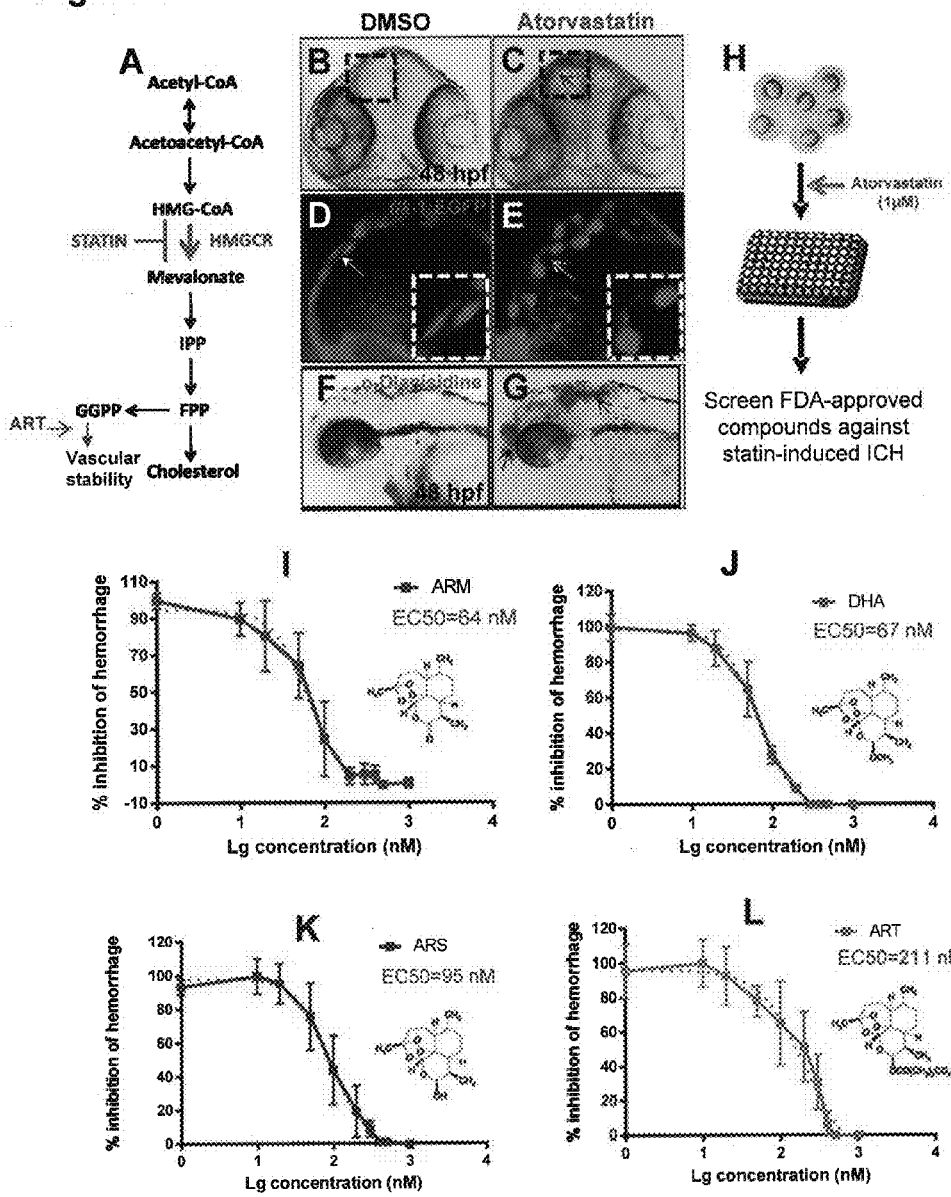
FIG. 1 shows the results of experiments using an atorvastatin-induced intracerebral hemorrhage (ICH) model in zebrafish for chemical screening. Panel (A) is a schematic diagram showing the molecular pathway where statins act. Panels B-G: ICH was induced by application of 1 μM atorvastatin at 2 hours post fertilization (hpf) of embryos from adult wild type or Tg (flk-1:eGFP) and Tg (gata-1: DsRed) zebrafish, and arrayed into 96-well plates that contain the drug compounds. Panels B, D and F (embryos treated with DMSO control); panels C, E and G, (embryos treated with atorvastatin). Panels B, D and F show no extravasations of red blood cells in vehicle DMSO-treated control embryos. Atorvastatin treated embryos show hemorrhage in the brain (≈80% panels C and G), and increased junction between endothelial cells (compare Panel E to panel D). Panel H is a schematic showing the scheme of the screening process. Panels I to L show EC50 experiments for four compounds from the ART family, two of which were identified from the NCC library. Data is expressed as mean±SEM from 3 to 4 experiments. ARM, artemether; DHA, dihydro-artemisinin; ARS, artemisinin; ART, artesunate.

The term "active" as used herein refers to the ingredient, component or constituent of the compositions of the described invention responsible for the intended therapeutic effect. The term "administer" as used herein means to give or to apply. The term "administering" as used herein includes in vivo administration, as well as administration directly to cells or a tissue ex vivo.

The term "agonist" as used herein refers to a chemical substance capable of activating a receptor to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A super-agonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The term "amplification" as used herein refers to a replication of genetic material that results in an increase in the number of copies of that genetic material.

Anatomical Terms:

When referring to animals, that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal"; a point farther away is "distal". Three basic reference planes are used in zoological anatomy. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is a Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, lateral structures are further from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

The term "antagonist" as used herein refers to a substance that counteracts the effects of another substance.

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways.

The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the tumor necrosis factor receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. Tumor necrosis factor family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis. Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway (Loberg, R D, et al. (2002) J. Biol. Chem. 277 (44): 41667-673). It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon agregation and mitochondrial localization, induces cytochrome c release. Akt is a critical regulator of GSK-3, and phosphorylation and inactivation of GSK-3 may mediate some of the antiapoptotic effects of Akt.

The term "appearance" as used herein refers to an outward aspect or presentation of oneself.

The term "apply" as used herein refers to placing in contact with or to lay or spread on.

The term "assay marker" or "reporter gene" (or "reporter") refers to a gene that can be detected, or easily identified and measured. The expression of the reporter gene may be measured at either the RNA level, or at the protein level. The gene product, which may be detected in an experimental assay protocol, includes, but is not limited to, marker enzymes, antigens, amino acid sequence markers, cellular phenotypic markers, nucleic acid sequence markers, and the like. Researchers may attach a reporter gene to another gene of interest in cell culture, bacteria, animals, or plants. For example, some reporters are selectable markers, or confer characteristics upon on organisms expressing them allowing the organism to be easily identified and assayed. To introduce a reporter gene into an organism, researchers may place the reporter gene and the gene of interest in the same DNA construct to be inserted into the cell or organism. For bacteria or eukaryotic cells in culture, this may be in the form of a plasmid. Commonly used reporter genes may include, but are not limited to, fluorescent proteins, luciferase, β-galactosidase, and selectable markers, such as chloramphenicol and kanomycin.

The term "associate" and its various grammatical forms as used herein refers to joining, connecting, or combining to, either directly, indirectly, actively, inactively, inertly, non-inertly, completely or incompletely.

The term "in association with" as used herein refers to a relationship between two substances that connects, joins or links one substance with another The term "biomarkers" (or "biosignatures") as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention. The term "indicator" as used herein refers to any substance, number or ratio derived from a series of observed facts that may reveal relative changes as a function of time; or a signal, sign, mark, note or symptom that is visible or evidence of the existence or presence thereof. Once a proposed biomarker has been validated, it may be used to diagnose disease risk, presence of disease in an individual, or to tailor treatments for the disease in an individual (choices of drug treatment or administration regimes). In evaluating potential drug therapies, a biomarker may be used as a surrogate for a natural endpoint, such as survival or irreversible morbidity. If a treatment alters the biomarker, and that alteration has a direct connection to improved health, the biomarker may serve as a surrogate endpoint for evaluating clinical benefit. Clinical endpoints are variables that can be used to measure how patients feel, function or survive. Surrogate endpoints are biomarkers that are intended to substitute for a clinical endpoint; these biomarkers are demonstrated to predict a clinical endpoint with a confidence level acceptable to regulators and the clinical community.

The term "cDNA" refers to DNA synthesized from a mature mRNA template. cDNA most often is synthesized from mature mRNA using the enzyme reverse transcriptase. The enzyme operates on a single strand of mRNA, generating its complementary DNA based on the pairing of RNA base pairs (A, U, G, C) to their DNA complements (T, A, C, G). There are several methods known for generating cDNA to obtain, for example, eukaryotic cDNA whose introns have been spliced. Generally, these methods incorporate the following steps: a) a eukaryotic cell transcribes the DNA (from genes) into RNA (pre-mRNA); b) the same cell processes the pre-mRNA strands by splicing out introns, and adding a poly-A tail and 5' methyl-guanine cap; c) this mixture of mature mRNA strands are extracted from the cell; d) a poly-T oligonucleotide primer is hybridized onto the poly-A tail of the mature mRNA template (reverse transcriptase requires this double-stranded segment as a primer to start its operation); e) reverse transcriptase is added, along with deoxynucleotide triphosphates (A, T, G, C); f) the reverse transcriptase scans the mature mRNA and synthesizes a sequence of DNA that complements the mRNA template. This strand of DNA is complementary DNA (see also Current Protocols in Molecular Biology, John Wiley & Sons, incorporated in its entirety herein).

The term "cell" is used herein to refer to the structural and functional unit of living organisms and is the smallest unit of an organism classified as living.

The term "cell culture" as used herein refers to establishment and maintenance of cultures derived from dispersed cells taken from original tissues, primary culture, or from a cell line or cell strain.

The term "cell line" as used herein refers to an immortalized cell, which have undergone transformation and can be passed indefinitely in culture.

The term "compatible" as used herein means that the components of a composition are capable of being combined with each other in a manner such that there is no interaction that would substantially reduce the efficacy of the composition under ordinary use conditions.

The terms "composition" and "formulation" are used interchangeably herein to refer to a product of the described invention that comprises all active and inert ingredients. The terms "pharmaceutical composition" or "pharmaceutical formulation" as used herein refer to a composition or formulation that is employed to prevent, reduce in intensity, cure or otherwise treat a target condition or disease.

The term "contacting" as used herein refers to bring or put in contact, to be in or come into contact. The term "contact" as used herein refers to a state or condition of touching or of immediate or local proximity. Contacting a composition to a target destination, such as, but not limited to, an organ, a tissue, or a cell, may occur by any means of administration known to the skilled artisan.

The terms "deletion" and "deletion mutation" are used interchangeably herein to refer to that in which a base or bases are lost from the DNA.

The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative." Derivatives can include chemical modifications of the peptide, such as akylation, acylation, carbamylation, iodination or any modification that derivatizes the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides that contain one or more naturally occurring amino acid derivative of the twenty standard amino acids, for example, 4-hydroxyproline, 5-hydroxylysine, 3-methylhistidine, homoserine, ornithine or carboxyglutamiate, and can include amino acids that are not linked by peptide bonds. Such peptide derivatives can be incorporated during synthesis of a peptide, or a peptide can be modified by well-known chemical modification methods (see, e.g., Glazer et al. (1975), Chemical Modification of Proteins, Selected Methods and Analytical Procedures, Elsevier Biomedical Press, New York).

The term "detectable marker" encompasses both selectable markers and assay markers. The term "selectable markers" refers to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like. When a nucleic acid is prepared or altered synthetically, advantage can be taken of known codon preferences of the intended host where the nucleic acid is to be expressed.

The term "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

The term "differentiation" as used herein refers to a property of cells to exhibit tissue-specific differentiated properties in culture.

The term "effective amount" refers to the amount necessary or sufficient to realize a desired biologic effect.

The term "EC50" as used herein refers to the concentration (expressed in molar units or g/L) of a drug that produces 50% of the maximal possible effect of that drug.

The term "expression system" refers to a genetic sequence, which includes a protein encoding region operably linked to all of the genetic signals necessary to achieve expression of the protein encoding region. Traditionally, the expression system will include a regulatory element such as, for example, a promoter or enhancer, to increase transcription and/or translation of the protein encoding region, or to provide control over expression. The regulatory element may be located upstream or downstream of the protein encoding region, or may be located at an intron (non-coding portion) interrupting the protein encoding region. Alternatively, it also is possible for the sequence of the protein encoding region itself to comprise regulatory ability.

The term "hpf" as used herein refers to hours post fertilization.

The term "hybridization" refers to the process of combining complementary, single-stranded nucleic acids into a single molecule. Nucleotides will bind to their complement under normal conditions, so two perfectly complementary strands will bind (or 'anneal') to each other readily. However, due to the different molecular geometries of the nucleotides, a single inconsistency between the two strands will make binding between them more energetically unfavorable. Measuring the effects of base incompatibility by quantifying the rate at which two strands anneal can provide information as to the similarity in base sequence between the two strands being annealed. The term "specifically hybridizes" as used herein refers to the process whereby a nucleic acid distinctively or definitively forming base pairs with complementary regions of at least one strand of DNA that was not originally paired to the nucleic acid. A nucleic acid that selectively hybridizes undergoes hybridization, under stringent hybridization conditions, of the nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 70%, at least 75%, at least 80%, at least 85%, at least 90%, at least 95%, at least 96%, at least 97%, at least 98%, or at least 99% sequence identity, or 100% sequence identity (i.e., complementary) with each other.

The term "hypomorphic mutation" as used herein refers to a type of mutation in which the altered gene product possesses a reduced level of activity, or in which the wild-type gene product is expressed at a reduced level.

The terms "inhibiting", "inhibit" or "inhibition" are used herein to refer to reducing the amount or rate of a process, to stopping the process entirely, or to decreasing, limiting, or blocking the action or function thereof. Inhibition may include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "inhibitor" as used herein refers to a molecule that binds to an enzyme thereby decreasing enzyme activity. Enzyme inhibitors are molecules that bind to enzymes thereby decreasing enzyme activity. The binding of an inhibitor may stop substrate from entering the active site of the enzyme and/or hinder the enzyme from catalyzing its reaction. Inhibitor binding is either reversible or irreversible. Irreversible inhibitors usually react with the enzyme and change it chemically, for example, by modifying key amino acid residues needed for enzymatic activity. In contrast, reversible inhibitors bind non-covalently and produce different types of inhibition depending on whether these inhibitors bind the enzyme, the enzyme-substrate complex, or both. Enzyme inhibitors often are evaluated by their specificity and potency.

An "isolated molecule" is a molecule that is substantially pure and is free of other substances with which it is ordinarily found in nature or in vivo systems to an extent practical and appropriate for its intended use. In particular, the compositions are sufficiently pure and are sufficiently free from other biological constituents of host cells so as to be useful in, for example, producing pharmaceutical preparations or sequencing if the composition is a nucleic acid, peptide, or polysaccharide. Because compositions may be admixed with a pharmaceutically-acceptable carrier in a pharmaceutical preparation, the compositions may comprise only a small percentage by weight of the preparation. The composition is nonetheless substantially pure in that it has been substantially separated from the substances with which it may be associated in living systems or during synthesis. As used herein, the term "substantially pure" refers purity of at least 75%, at least 80%, at least 85%, at least 90%, at least 95% or at least 99% pure as determined by an analytical protocol. Such protocols may include, for example, but are not limited to, fluorescence activated cell sorting, high performance liquid chromatography, gel electrophoresis, chromatography, and the like.

The term "minimizing progression" as used herein refers to reducing the amount, extent, size, or degree of development of a sequence or series of events.

The term "modulate" as used herein means to regulate, alter, adapt, or adjust to a certain measure or proportion.

The term "morpholino oligonucleotides (MO)" as used herein refer to nonionic DNA analogs with a phosphorodiamidate molecular backbone, which blocks access of other molecules to specific sequences within antisense nucleic acid sequences. Although they possess altered backbone linkages compared with DNA or RNA, morpholinos bind to complementary nucleic acid sequences by Watson-Crick base-pairing. This binding is no tighter than binding of analogous DNA and RNA oligomers, necessitating the use of relatively long 25-base morpholinos for antisense gene inhibition. The backbone makes morpholinos resistant to digestion by nucleases. Also, because the backbone lacks negative charge, it is thought that morpholinos are less likely to interact nonselectively with cellular proteins; such interactions often obscure the observation of informative phenotypes (Corey, D. R. and J. M. Abrams (2001) "Morpholino antisense oligonucleotides: tools for investigating vertebrate development," Genome Biol. 2(5): 1015.1-1015.3). Duplex formation between MOs and mRNA prevents translation through MO hybridization near the mRNA translation initiation codon and disrupts correct splicing by targeting the splice donor site Wada, T. et al (2012) "Antisense morpholino targeting just upstream from a poly(A) tail junction of material mRNA remoes the tail and inhibits translation," Nucleic Acids Res. 40 (22): e173).

The term "mutation" as used herein refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "nucleic acid" is used herein to refer to a DNA or RNA polymer in either single- or double-stranded form, and unless otherwise limited, encompasses known analogues having the essential nature of natural nucleotides in that they hybridize to single-stranded nucleic acids in a manner similar to naturally occurring nucleotides (e.g., MO oligonucleotides).

The term "nucleotide" is used herein to refer to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The phrase "operably linked" refers to a first sequence(s) or domain being positioned sufficiently proximal to a second sequence(s) or domain so that the first sequence(s) or domain can exert influence over the second sequence(s) or domain or a region under control of that second sequence or domain.

The term "polynucleotide" refers to a DNA, RNA or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide may be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The term "pharmaceutical composition" as used herein refers to a composition that is employed to prevent, reduce in intensity, cure or otherwise treat a target condition, syndrome, disorder or disease.

The term "pharmaceutically acceptable carrier" as used herein refers to any substantially non-toxic carrier conventionally useable for administration of pharmaceuticals in which the isolated polypeptide of the present invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The term "primer" refers to a nucleic acid which, when hybridized to a strand of DNA, is capable of initiating the synthesis of an extension product in the presence of a suitable polymerization agent. The primer is sufficiently long to uniquely hybridize to a specific region of the DNA strand. A primer also may be used on RNA, for example, to synthesize the first strand of cDNA.

The term "promoter" refers to a region of DNA upstream, downstream, or distal, from the start of transcription and involved in recognition and binding of RNA polymerase and other proteins to initiate transcription. For example, T7, T3 and Sp6 are RNA polymerase promoter sequences. In RNA synthesis, promoters are a means to demarcate which genes should be used for messenger RNA creation and by extension, control which proteins the cell manufactures. Promoters represent critical elements that can work in concert with other regulatory regions (enhancers, silencers, boundary elements/insulators) to direct the level of transcription of a given gene.

The term "reduced" or "to reduce" as used herein refer to a diminishment, a decrease, an attenuation or abatement of the degree, intensity, extent, size, amount, density or number of.

The term "refractory" as used herein refers to the state of being unaffected, unresponsive, resistant or not fully responsive.

The term "restriction digestion" refers to a procedure used to prepare DNA for analysis or other processing. Also known as DNA fragmentation, it uses a restriction enzyme to selectively cleave strands of DNA into shorter segments.

The term "restriction enzyme" (or restriction endonuclease) refers to an enzyme that cuts double-stranded DNA.

The term "restriction sites" or "restriction recognition sites" refer to particular sequences of nucleotides that are recognized by restriction enzymes as sites to cut a DNA molecule. The sites are generally, but not necessarily, palindromic, (because restriction enzymes usually bind as homodimers) and a particular enzyme may cut between two nucleotides within its recognition site, or somewhere nearby.

The term "Rho" as used herein refers to a subfamily of proteins related to the RAS subgroup thought to be involved in cell transformation and the regulation of morphology and function of dendritic cells. Non-limiting examples of Rho proteins include RhoA, RhoB and RhoC, RhoG, RhoH, RhoQ, RhoU RhoV, Rnd1, 2 and 3 (e.g., RhoE), and RAC1, 2, 3 and 4.

Sequence:

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity".

The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman (1981), Adv. Appl. Math. 2:482; by the homology alignment algorithm of Needleman and Wunsch (1970), J. Mol. Biol. 48:443; by the search for similarity method of Pearson and Lipman (1988), Proc. Natl. Acad. Sci. 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp (1988), Gene 73:237-244; Higgins and Sharp (1989) CABIOS 5:151-153; Corpet, et al. (1988) Nucleic Acids Research 16:10881-90; Huang, et al. (1992) Computer Applications in the Biosciences 8:155-65, and Pearson, et al. (1994) Methods in Molecular Biology 24:307-331. The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters (Altschul et al. (1997) Nucleic Acids Res. 25:3389-3402). Software for performing BLAST analyses is publicly available, e.g., through the National Center for Biotechnology-Information (http://www.hcbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen (1993), Comput. Chem., 17:149-163) and XNU (Claverie and States (1993) Comput. Chem., 17:191-201) low-complexity filters may be employed alone or in combination.

The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller (1988) Computer Applic. Biol. Sci., 4:11-17, e.g., as implemented in the program PC/GENE (Intelligenetics, Mountain View, Calif., USA).

The term "percentage of sequence identity" as used herein means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The terms "substantial identity" in the context of a peptide indicates that a peptide comprises a sequence with at least 70% sequence identity to a reference sequence, at least 80%, at least 85%, at least 90% or 95% sequence identity to the reference sequence over a specified comparison window. Optionally, optimal alignment is conducted using the homology alignment algorithm of Needleman and Wunsch (1970) J. Mol. Biol. 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

The term "subject" or "individual" or "patient" are used interchangeably to refer to a member of an animal species of vertebrate origin, e.g., a zebrafish, to mammalian origin, including but not limited to, mouse, rat, cat, goat, sheep, horse, hamster, ferret, pig, dog, platypus, guinea pig, rabbit and a primate, such as, for example, a monkey, ape, or human.

The phrase "subject in need thereof" as used herein refers to a patient that (i) susceptible to ICH, BMH or CCM that will be administered a therapeutic agent according to the described invention to treat the ICH, BMH or CCM, (ii) is receiving a therapeutic agent according to the described invention to treat ICH/BMH or CCM; or (iii) has received a therapeutic agent according to the described invention to treat ICH/BMH or CCM, unless the context and usage of the phrase indicates otherwise.

The term "substitution" is used herein to refer to that in which a base or bases are exchanged for another base or bases in DNA. Substitutions may be synonymous substitutions or nonsynonymous substitutions. As used herein, "synonymous substitutions" refer to substitutions of one base for another in an exon of a gene coding for a protein, such that the amino acid sequence produced is not modified. The term "nonsynonymous substitutions" as used herein refer to substitutions of one base for another in an exon of a gene coding for a protein, such that the amino acid sequence produced is modified.

The term "susceptible" as used herein refers to a member of a population at risk.

The term "therapeutic agent" as used herein refers to a drug, molecule, nucleic acid, protein, composition or other substance that provides a therapeutic effect. The term "active" as used herein refers to the ingredient, component or constituent of the compositions of the present invention responsible for the intended therapeutic effect. The terms "therapeutic agent" and "active agent" are used interchangeably herein. The active agent may be a therapeutically effective amount of at least one of an active agent itself, a mimic, a derivative, an agonist of that active agent, or a pharmaceutically acceptable salt thereof.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the $ED_{50}$, which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect also may include, directly or indirectly, the arrest reduction or elimination of the progression of a disease manifestation.

The terms "therapeutic amount", an "amount effective", or "pharmaceutical amount" of one or more of the active agents and used interchangeably to refer to an amount that is sufficient to provide the intended benefit of treatment.

The intensity of effect of a drug (y-axis) can be plotted as a function of the dose of drug administered (X-axis) (Goodman & Gilman's The Pharmacological Basis of Therapeutics, Ed. Joel G. Hardman, Lee E. Limbird, Eds., 10th Ed., McGraw Hill, New York (2001), p. 25, 50). These plots are referred to as dose-effect curves. Such a curve can be resolved into simpler curves for each of its components. These concentration-effect relationships can be viewed as having four characteristic variables: potency, slope, maximal efficacy, and individual variation.

The location of the dose-effect curve along the concentration axis is an expression of the potency of a drug (Id).

The slope of the dose-effect curve reflects the mechanism of action of a drug. The steepness of the curve dictates the range of doses useful for achieving a clinical effect.

The terms "maximal efficacy" or "clinical efficacy" as used interchangeably herein refer to the maximal effect that can be produced by a drug. Maximal efficacy is determined principally by the properties of the drug and its receptor-effector system and is reflected in the plateau of the curve. In clinical use, a drug's dosage may be limited by undesired effects.

The term "biological variability" as used herein refers to an effect of varying intensity that may occur in different individuals at a specified concentration of a drug. It follows that a range of concentrations may be required to produce an effect of specified intensity in all subjects.

Lastly, different individuals may vary in the magnitude of their response to the same concentration of a drug when the appropriate correction has been made for differences in potency, maximal efficacy and slope.

The duration of a drug's action is determined by the time period over which concentrations exceed the minimum effective concentration (MEC). Following administration of a dose of drug, its effects usually show a characteristic temporal pattern. A plot of drug effect versus time illustrates the temporal characteristics of drug effect and its relationship to the therapeutic window. A lag period is present before the drug concentration exceeds the MEC for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. The therapeutic window reflects a concentration range that provides efficacy without unacceptable toxicity. Accordingly another dose of drug should be given to maintain concentrations within the therapeutic window.

The term "transcription termination signal" refers to a section of genetic sequence that marks the end of gene or operon on genomic DNA for transcription. In prokaryotes, two classes of transcription termination signals are known: 1) intrinsic transcription termination signals where a hairpin structure forms within the nascent transcript that disrupts the mRNA-DNA-RNA polymerase ternary complex; and 2) Rho-dependent transcription termination signal that require Rho factor, an RNA helicase protein complex to disrupt the nascent mRNA-DNA-RNA polymerase ternary complex. In eukaryotes, transcription termination signals are recognized by protein factors that co-transcriptionally cleave the nascent RNA at a polyadenlyation signal (i.e, "poly-A signal" or "poly-A tail") halting further elongation of the transcript by RNA polymerase. The subsequent addition of the poly-A tail at this site stabilizes the mRNA and allows it to be exported outside the nucleus. Termination sequences are distinct from termination codons that occur in the mRNA and are the stopping signal for translation, which also may be called nonsense codons.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The terms "variants", "mutants", and "derivatives" are used herein to refer to nucleotide sequences with substantial identity to a reference nucleotide sequence. The differences in the sequences may by the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence.

The term "vascular leakage" as used herein refers to a pathologic increase in vascular permeability.

The term "vascular permeability" as used herein refers to the net amount of a solute, typically a macromolecule that has crossed a vascular bed and accumulated in the interstitium in response to a vascular permeabilizing agent or at a site of pathological angiogenesis.

The term "vascular stability" as used herein includes the control of endothelial cell cytoskeleton and junction proteins and the interaction of endothelial cells with mural cells.

The term "wild-type" as used herein refers to the typical form of an organism, strain, gene, protein, nucleic acid, or characteristic as it occurs in nature. Wild-type refers to the most common phenotype in the natural population. The terms "wild-type" and "naturally occurring" are used interchangeably.

According to one aspect, the described invention provides a method for reducing incidence of bleeding in the brain by administering a pharmaceutical composition containing a small molecule therapeutic compound, a therapeutic amount of which is effective to reduce incidence of bleeding in the brain by at least 30%, at least 35%, at least 40%, at least 45%, at least 50%, at least 55%, by 60% or less, by 55% or less, by 50% or less, by 45% or less, by 40% or less, by 35% or less, by 30% or less, relative to a control.

According to some embodiments, the small molecule therapeutic compound is selected from the group consisting of artemether or a derivative of artemether. According to some embodiments, the derivative of artemisinin is dihydroartemisinin, artemesinin, or artesunate.

According to some embodiments, the small molecule therapeutic compound is selected from the group consisting of benidipine, lacidipine, ethynylestradiol or triptolide.

According to some embodiments, the bleeding in the brain is induced by a statin, by a lipopolysaccharide, or both.

According to some embodiments, the statin is atorvastatin.

According to some embodiments the bleeding in the brain is a spontaneous intracerebral hemorrhage.

According to some embodiments, the spontaneous intracerebral hemorrhage occurs in association with administration of a statin.

According to some embodiments, the bleeding in the brain is a brain microhemorrhage.

According to some embodiments, the brain microhemorrhage occurs in association with administration of a statin.

According to some embodiments, the bleeding in the brain comprises a brain vascular malformation.

According to some embodiments, the brain vascular malformation is a cerebral cavernous malformation.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

Zebrafish Husbandry

All zebrafish (*Danio rerio*) experiments were conducted under St. Michael's Hospital Animal Care Committee (Toronto, Ontario, Canada) approved protocol ACC403. The zebrafish were housed in the Li Ka Shing Knowledge Institute (St. Michael's Hospital, Toronto, Ontario, Canada) research vivarium and maintained and staged as previously described (Avdesh A, Chen M, Martin-Iverson M T et al. Regular care and maintenance of a zebrafish (*Danio rerio*) laboratory: an introduction. J Vis Exp 2012; e4196). In short, the fish were housed under a 14 h light: 10 h dark cycle at 28° C. Embryos were produced by pair mating and raised in 1×E3 embryo medium (5 mM NaCl, 0.17 mM KCl, 0.33 mM $CaCl_2$, 0.33 mM $MgSO_4$. Strains used in this study included Tg(Flk:GFP; Gata:dsRed) and bbh(m292); kdrl: mCherry −/−). The collection of fertilized eggs was obtained through pair-wise breeding according to the standard method previously described (Id.).

Statin-induced Brain Hemorrhage in Zebrafish

Zebrafish as a model for hemorrhagic stroke has been proposed previously (Butler M G, Gore A V, Weinstein B M. Zebrafish as a model for hemorrhagic stroke. Methods Cell Biol 2011; 105:137-161). In addition to genetic models of brain hemorrhage, statins have been used to induce brain hemorrhage in zebrafish (Gjini E, Hekking L H, Kuchler A et al. Zebrafish Tie-2 shares a redundant role with Tie-1 in heart development and regulates vessel integrity. Dis Model Mech 2011; 4:57-66; Eisa-Beygi S, Hatch G, Noble S, Ekker M, Moon T W. The 3-hydroxy-3-methylglutaryl-CoA reductase (HMGCR) pathway regulates developmental cerebralvascular stability via prenylation-dependent signalling pathway. Dev Biol 2013; 373:258-266). A statin-induced model was adopted for our NIH drug library screening project.

Zebrafish were set up the night before the experiment day. In the morning of the experimental day, we put breeders together for mating and fertilization. 6 hours post-fertilization (hpf), statins was added into a 96-well plate holding 100 µl water with 7 to 8 fish eggs in each well, which was optimized through a serial pilot experiments. Statins were dissolved in DMSO and diluted with 0.5% of DMSO water into a working solution. 100 µl water containing 0.5% of DMSO was the medium for all wells in the final assessment.

Initially, we tested both simvastatin and atorvastatin for induction of brain hemorrhage. Simvastatin was tested in final concentrations of 10, 25, 50, 100, and 200 nmol/L, and atorvastatin (ATV) was tested in concentrations of 50, 150, 300, 500 nmol/L and 1 µM. After several batches of experiments, we found that ATV at 1 µM gave the best reproducible brain hemorrhage in more than 80% of the larvae fish. Therefore, all subsequent screening work was done with 1 µM ATV to induce brain hemorrhage in larvae zebrafish. Simvastatin (MW 558.6) was purchased from Cayman Chemical (Ann Arbor, Mich.) and atorvastatin calcium salt (MW 604.69) was purchased from Sigma (St Louis, Mo.).

For screening NIH compound libraries, 5 µM of each of the drugs from the library was added at 24 hpf into wells containing fish eggs treated with 1 µM ATV since 6 hpf. Hemorrhage positive control wells were treated with ATV but not treated with any drugs. Negative controls were not treated with any chemicals (fish with 0.5% of DMSO water). Geranylgeranyl pyrophosphate (GGPP, 4 mg/L) was used as positive rescue control.

Brain hemorrhage was assessed 72 hpf (66 hours after addition of statins) using stereomicroscopy by two observers. Percentage of brain hemorrhage was used as final readout. Compounds showing more than 70% of rescue of the brain hemorrhages in the initial test were re-tested to generate a final list of hits from the library.

Four other compounds plus artesunate and artemether were independently identified as positive hits from the library. Their derivatives (artemisinin and dihydro-artimisinin) were acquired (Sequoia Research Products, Pangbourne, U K) and tested positive in the same ATV zebrafish model. All subsequent EC50 assays of positive compounds were performed with protocols established and optimized during the screening.

Morpholino Injection

Morpholino oligonucleotides (MOs) were custom-synthesized by Gene Tools (Carvalis, Oreg.); their sequences are shown in Table 1.

TABLE 1

Morpholino sequences

| Morpholino | Sequence | SEQ ID NO: |
|---|---|---|
| Rap1bEx3 | 5'-AAATGATGCAGAACTTGCCTTTCTG-3' | SEQ ID NO: 1 |
| cdh5exon2 | 5'-TACAAGACCGTCTACCTTTCCAATC-3' | SEQ ID NO: 2 |
| βPixexon6 | 5'-GCGCATCTCTCTTACCACATTATAG-3 | SEQ ID NO: 3 |
| pak2aexon8 | 5'-AATAGAGTACAACATACCTCTTGGC-3' | SEQ ID NO: 4 |
| Hmgcrb-splice | 5'-AACTGCATTCATAAACTCACCCAGT-3' | SEQ ID NO: 5 |
| Pggt1-MO/ggtaseI splice | 5'-CACGCGGTGTGTGGACTCACGGTCA-3' | SEQ ID NO: 6 |
| Liss Std Control | 5'-CCTCTTACCTCAGTTACAATTTATA-3' | SEQ ID NO: 7 |

Figure 14:
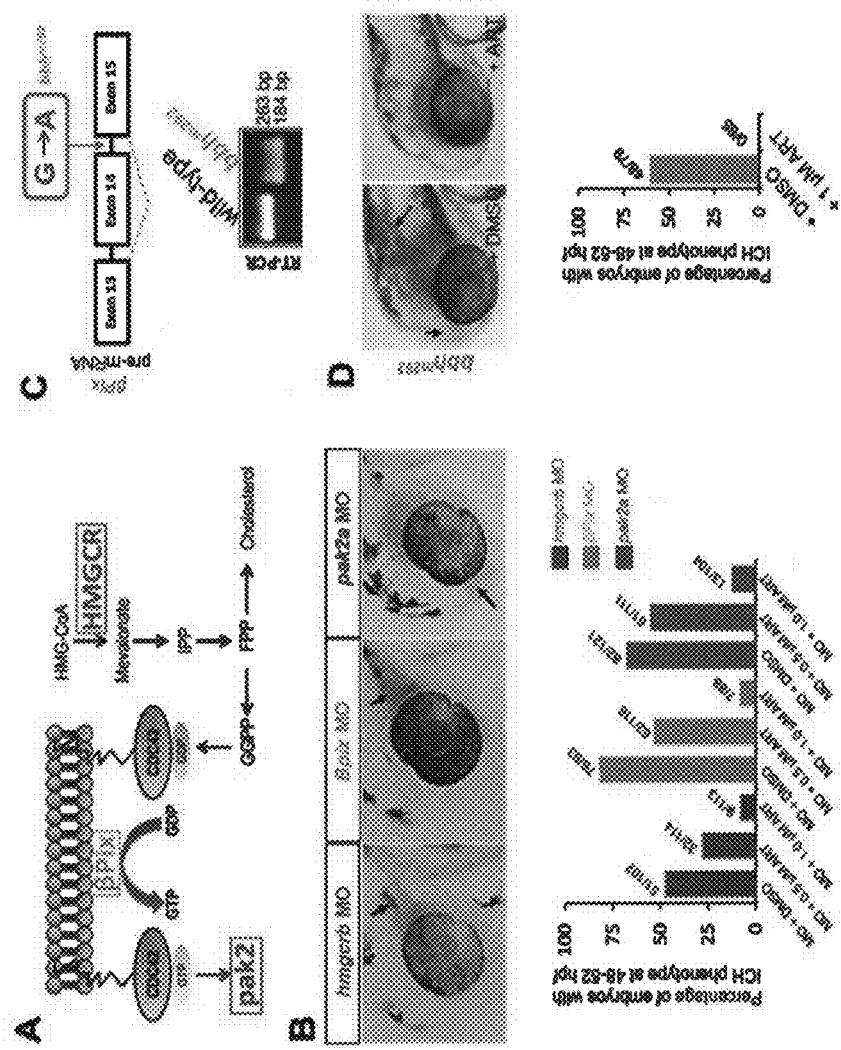
FIG. 14 Panels (A-B) shows that artesunate dose-dependently rescues hemorrhage phenotype induced by morpholinos targeting membrane stability of brain vessels in zebrafish. (A) Schematic diagram showing the target sites of the three morpholinos studied. (B) Artesunate dose-dependently rescues all three morpholinos-induced brain hemorrhage in zebrafish. Panels (C-D) Artesunate rescues the ICH phenotype underlying the bbh$^{m292}$ mutation. (C) Upper panel, partial exon-intron organization of bPix gene showing the point mutation effecting splicing of the gene. Lower panel, RT-PCR analysis of wild-type and bbh$^{m292}$ mutant cDNA with primers flanking exon-14. (D) Upper panel, the phenotypes of bbh$^{m292}$ mutants treated with DMSO or artesunate and imaged at 48 hpf. The arrows denote sites of hemorrhage. Lower panel, percentages of bbh$^{m292}$ embryos with brain hemorrhage rescued by artesunate.

Danieau buffer (58 mM NaCl, 0.7 mM KCl, 0.4 mM MgSO$_4$, 0.6 mM Ca(NO$_3$)$_2$, 5.0 mM HEPES, pH 7.6) was used to dilute the MO solutions to 0.2 mM final concentration. Individual wells were placed on a 1.0% agarose plate, in which the embryos were positioned. Afterwards, the MO solution was injected through the cell yolk into embryos of 1 to 4 cell-stage. The injected quantities varied from 0.5 to 15 ng.

bbhm292 zebrafish mutant has a hypomorphic mutation in βPix, resulting in ICH/BMH and hydrocephalus. The MO is βPixexon6-MO which blocks splicing of exon 6 and results in premature protein termination. Injection of 0.2 ng of βPixexon6-MO resulted in ICH in 61% of embryos. Higher doses of βPixexon6-MO (up to 8 ng) result in a lack of blood circulation, and therefore no ICH/BMH was detected. Injection of 8 ng results in complete missplicing of βPix and therefore a null phenotype, whereas lower doses retain some normally spliced βPix. The βPixexon6-MO sequence is 5'-GCGCATCTCTCTTACCACATTATAG-3' [SEQ ID NO: 1]. 3Pixexon6-MO was injected into the embryos at the 1-2 cell stage, and compounds were added 12 hpf. Artesunate, 5 μmol/L, prevented ICH (FIG. 14).

Another MO was designed to block the splice-donor sites after exon 8 in pak2a. Pak2a is the gene mutated in the rhdmi149 zebrafish mutant that develops ICH/BMH. The pak2a-MO sequence is 5'-AATAGAGTACAACATAC-CTCTTGGC-3' (SEQ ID NO: 2). Eight pg of pak2a-MO was injected per embryo, resulting in ~80% of embryos with ICH/BMH with low mortality (FIGS. 12 and 14).

Figure 12:
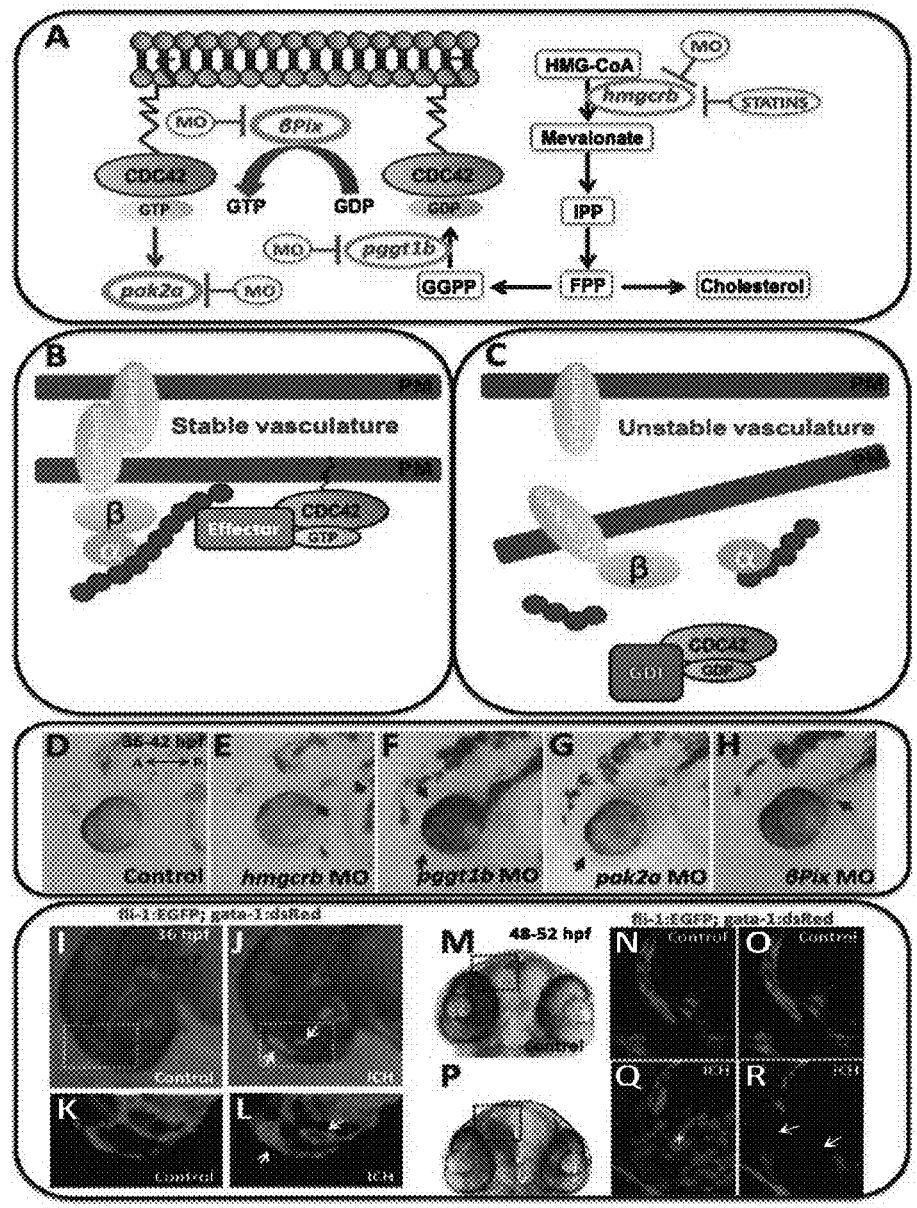
FIG. 12 shows the pharmacological and genetic induction of loss of cerebrovascular stabilization in developing zebrafish. (A) Schematic representation of genetic pathways involved in cerebrovascular stabilization. (B) Schematic representation of VE-cadherin-mediated cell-cell adhesion regulated in part by Cdc42. (C) Schematic representation illustrating that unprenylated Cdc42 remains inactive (GDP-bound) and associated with guanine nucleotide dissociation inhibitor (GDI). (D) Photograph depicting un-injected embryos. (E) Photograph depicting embryos injected with MOs targeting hmgcrb (E). (F) Photograph depicting embryos injected with MOs targeting pggt1b. (G) Photograph depicting embryos injected with MOs targeting βpix. (H) Photograph depicting embryos injected with MOs targeting pak2a. Arrows denote the sites of abnormal accumulation of blood. (I, K) are representative photomicrographs of Tg(fli1:EGFP);(gata-1:DsRed) embryos incubated in DMSO. (J, L) are representative photomicrographs of Tg(fli1:EGFP);(gata-1:DsRed) embryos incubated in atorvastatin. The arrows in (J) indicate areas where stagnant DsRed-positive erythrocyte accumulation is observed. The arrows in (L) denote distended cerebral vessels in the same fish. (M, P) are photographs depicting hemorrhages associated with the fragmentation of the underlying vasculature. (N, O) depict representative bright-field photomicrographs of Tg (fli1:EGFP);(gata-1:DsRed) embryos incubated in DMSO. (Q, R) depict representative bright-field photomicrographs of Tg (fli1:EGFP);(gata-1:DsRed) embryos incubated in atorvastatin. The asterisk denotes the hemorrhage and the black dotted area shows the field of interest. Z-stack projections of the black dotted area in the same Tg(fli1:EGFP);(gata-1:DsRed) embryos. The white asterisk denotes DsRed-positive erythrocytes and the white arrows show regions where vascular disintegration is observed. Anterior is to the left as shown in (I-R).

FIG. 12 depicts the pharmacological and genetic induction of loss of cerebrovascular stabilization in developing zebrafish. (A) The putative relationship between the HMGCR (hmgcrb)-mediated metabolic pathway and Rho GTPase (CDC42) signalling in zebrafish is shown. The process of geranylgeranylation, catalysed by GGTase I (pggt1b), facilitates translocation of CDC42 to the plasma membrane. The membrane-bound CDC42 functions as a molecular switch by alternating between a GDP-bound (inactive) state and a GTP-bound (active) state. βpix is a guanine exchange factor (GEF), as it activates CDC42 by stimulating GDP release and increasing enzyme affinity for GTP. The p21-activated kinase 2a (pak2a) is a binding partner for βPix. Pak2a is serine/threonine kinase acting downstream of Rho GTPase signalling and are involved in the transduction of this pathway. HMGCR function was inhibited using a splice inducing anti-sense morpholino oligonucleotide (MO) or water-borne exposure of embryos to statins (0.5 mg/L). The functions of pggt1b, βpix, or pak2a were reduced using gene-specific MOs. (B) VE-cadherin-mediated cell-cell adhesion is regulated in part by CDC42. When CDC42 is prenylated and in its GTP-bound active form, it interacts with the the α and β-catenins to maintain the VE-cadherin-catenin complex, hence conferring stability. (C) By contrast, the unprenylated CDC42 remains inactive (GDP-bound) and associated with guanine nucleotide dissociation inhibitor (GDI). This condition confers the weak adhesive activity, hence disrupted cell-cell stability. (D-H) Loss of the hmgcrb, pggt1b, βpix or pak2a genes precipitate cerebral hemorrhages. As compared with un-injected embryos in (D), those injected with MOs targeting hmgcrb (E), pggt1b (F), βpix (G), or pak2a (H) exhibited ICH phenotype at 36-52 hpf. Arrows denote the sites of abnormal accumulation of blood. Representative images are shown. Anterior is to the left. (I-L) Hemorrhages arise due to vascular defects in the brain. (I and J) Representative photomicrographs of Tg(fli1:EGFP);(gata-1:DsRed) embryos incubated in DMSO or 0.5 mg/L atorvastatin at 2 hpf and imaged at 36 hpf. The arrows in (J) indicate areas where stagnant DsRed-positive erythrocyte accumulation is observed. The arrows in (L) denote the unusually distended cerebral vessels in the same fish. Anterior is to the left. (M-R) Hemorrhages are associated with the fragmentation of the underlying vasculature. (M and P) Representative bright-field photomicrographs of Tg (fli1:EGFP); (gata-1:DsRed) embryos incubated in DMSO or 0.5 mg/L atorvastatin at 2 hpf and imaged at 48-52 hpf. The asterisk denotes the hemorrhage and the black dotted area shows the field of interest. Anterior is to the left and dorsal to the top. (N-R) Representative composite confocal Z-stack projections of the black dotted area in the same Tg(fli1:EGFP); (gata-1:DsRed) embryos. The white asterisk denotes DsRed-positive erythrocytes and the white arrows show regions where vascular disintegration is observed.

Measuring the Expression of Cellular Junction Proteins qRT-PCR was used to assess relative expression of selected genes (an average of two biological trial and three technical replicates and each trial is a pool of 60 larvae/treatment), using β-actin as the housekeeping gene control. 3 dpf, Tg(Flk:GFP; Gata:dsRed) zebrafish larvae were used for RNA extraction and cDNA synthesis. Atorvastatin and drug treatment were performed as previously mentioned in drug screening. Total RNA was extracted from these larvae (a pool of 50-60 larvae/treatment) using the RNeasy extraction kit (Qiagen, Mississauga, ON, CAN) and treated with DNase. The concentration of total RNA was determined spectrophotometrically at 260/280 nm using a NanoDrop™ spectrophotometer. First-strand cDNA was synthesized from 1 μg of total RNA using random hexamer primers.

PCR conditions: The genes of interest and the primer pairs used are shown in Table 2. In each case, forward primer is shown on the top and reverse primer on the bottom.

TABLE 2

Primer sequences for selected genes to perform qPCR.

| Protein name | Gene name | Primer Sequences (5'-3') | SEQ ID NO: |
| --- | --- | --- | --- |
| VE-Cadherin | Cdh5 | ACGATGTCTCCATCCTGTCT | SEQ ID NO: 8 |
| | | TAGTGATTCGGTTCCCTCAT | SEQ ID NO: 9 |
| CCM1 | Ccm1 | TCACGCTATTCCTGCTCTGT | SEQ ID NO: 10 |
| | | ACTGCAGATCTGAGCCGTAC | SEQ ID NO: 11 |
| CCM2 | Ccm2 | GGACAGCCAGCATTTTGAGA | SEQ ID NO: 12 |
| | | GTCTGAAATCATGCGGTCCC | SEQ ID NO: 13 |
| CCM3 | Ccm3 | CATGATTGACAGGCCCGAG | SEQ ID NO: 14 |
| | | TGATTGTCTGCAGGAATCGG | SEQ ID NO: 15 |
| Integrin β3 | Itgb3 | TCACTGTGGACTTTGCTTGC | SEQ ID NO: 16 |
| | | CACATTCACAGAACGGACCC | SEQ ID NO: 17 |

Amplification of cDNA was achieved with an initial denaturation at 94° C. for 2 min followed by 40 cycles of denaturation (94° C. for 30 sec), annealing (60° C. for 30 sec) and extension (72° C. for 1 min) followed by a final extension period of 10 min at 72° C. before termination. PCR was carried out in a 20 μl total volume and included 1×PCR buffer, 1.25 mM $MgCl_2$, 0.25 mM dNTP, 1 U Taq polymerase, 0.5 μmol/L forward, and reverse primers and 1 μl cDNA.

Toxicity Assay

The embryos were collected and distributed into a 96-well plate in 0.5% DMSO, similar to efficacy assays. Drugs were added at 24 hpf from a range of 50 nmol/L to 100 μmol/L. 3 days postfertilization (dpf), larvae were observed for heart beat, blood flow and cardiac edema; the drug treated larvae were compared to non-treated samples in 0.5% DMSO. Heart beat and blood flow were ranked from 3 (normal heart beat or blood flow) to 0 (no heart beat or blood flow). Cardiac edema was ranked from 0 (normal heart without edema) to -3 (severe cardiac edema). TC50 is the concentration of the drug at 50% of maximum toxicity. The ratio of TC50/EC50 was calculated in each case.

Mouse Model Work

Animals and Animal Husbandry

All mice were housed in individually ventilated microisolator cages at St. Michael's Hospital vivarium facility. Rooms were kept at an ambient temperature of 21° C. and subjected to a 12 hour light/dark cycles. Humidity was kept between 30-50%. All mice had access to autoclaved food and water ad libitum. Virox was used as disinfectant. Environmental Enrichment was provided for mice in each cage. The Animal Care Committee at St. Michael's Hospital approved all protocols and procedures in this study.

Lipopolysaccharide (LPS)-induced Microbleeding Model

An LPS-mediated micro bleeding model was created similar to that described in Lui et al (Liu S, Grigoryan M M, Vasilevko V et al. Comparative analysis of H&E and Prussian blue staining in a mouse model of cerebral microbleeds. J Histochem Cytochem 2014; 62:767-773). 9-10 week old C57BL/6 mice of both sexes were purchased from Charles River, and randomly assigned to control or treatment groups in equal numbers. LPS from Salmonella enterica (Sigma Aldrich, St Louis, Mo.) was reconstituted with PBS to a final concentration of 5 mg/ml. Both control (n=16) and drug treatment (n=16) groups received injections of 5 mg/kg LPS at times 0 and 24 hrs. The drug treatment group, further divided into high dose (n=4) and low dose (n=12), received intraperitoneal injections of artemether (ARM) (25 mg/kg for Low dose and 100 mg/kg for High dose) at time points -72, -48, -24, 0 and 24 hrs of LPS treatment. All mice were sacrificed at 48 hrs after the first LPS injection.

The brains were used for either histological studies or MRI study.

Anti-β3 Integrin Model of Intracerebral Hemorrhage (ICH)

An anti-β3 integrin model of intracerebral hemorrhage (ICH) was generated according to our previously reported methods (Yougbare I, Lang S, Yang H et al. Maternal anti-platelet beta3 integrins impair angiogenesis and cause intracranial hemorrhage. J Clin Invest 2015; 125:1545-1556). Briefly, serum containing anti-β3 antibodies was generated by immunizing β3-/- female mice with gel-filtered wild type platelets via tail-vein injections twice a week. To detect anti-β3 antibody, blood was collected from the saphenous vein of immunized female mice and left to clot. Serum was extracted by centrifuging blood at 9600 g for 5 minutes, incubated with FITC-conjugated anti-mouse IgG, and assayed by flow cytometer (FACSCalibur, BD Biosciences, Mississauga, ON).

To generate β3+/− mice, 6-8 week old β3−/− female mice were crossed with wild type male BALB/c. The resulting pups were randomly assigned to either control (n=29, without any treatment) or drug treatment group (n=24). To induce ICH in the pups, each mouse was injected intraperitoneally with either 50 μL of the anti-β3 sera (the Control group) or 50 μL anti-β3 sera with 25 mg/kg ARM (Drug Treatment group) at postnatal day 2 (P2). All Neonates were sacrificed by decapitation at P3.

Histological Studies on Mouse Brains

All histological studies are done according to our established protocols (D'Abbondanza J A, Ai J, Lass E et al. Robust effects of genetic background on responses to subarachnoid hemorrhage in mice. J Cereb Blood Flow Metab 2016; 36:1942-19547-13; Sabri M, Kawashima A, Ai J, Macdonald R L. Neuronal and astrocytic apoptosis after subarachnoid hemorrhage: a possible cause for poor prognosis. Brain Res 2008; 1238:163-171; Sabri M, Jeon H, Ai J et al. Anterior circulation mouse model of subarachnoid hemorrhage. Brain Res 2009; 1295:179-185; Sabri M, Ai J, Macdonald R L. Dissociation of vasospasm and secondary effects of experimental subarachnoid hemorrhage by clazosentan. Stroke 2011; 42:1454-1460; Sabri M, Ai J, Marsden P A, Macdonald R L. Simvastatin re-couples dysfunctional endothelial nitric oxide synthase in experimental subarachnoid hemorrhage. PLoS One 2011; 6:e17062; Sabri M, Ai J, Lakovic K, D'Abbondanza J, Ilodigwe D, Macdonald R L. Mechanisms of microthrombi formation after experimental subarachnoid hemorrhage. Neuroscience 2012; 224:26-37; Sabri M, Ai J, Lass E, D'Abbondanza J, Macdonald R L. Genetic elimination of eNOS reduces secondary complications of experimental subarachnoid hemorrhage. J Cereb Blood Flow Metab 2013; 33:1008-1014).

LPS-induced microbleeding model: All mice in the LPS study were deeply anesthetized with ketamine and xylazine and perfused through the left cardiac ventricle with NaCl, 0.9%, followed by 4% paraformaldehyde (PFA) in 1×PBS buffer and 2 mM Gadoteridol contrast agent for 24 hours. Each brain was transferred into a 1×PBS+0.02% sodium azide and 2 mM Gadoteridol contrast agent. Brains were kept in this immersion solution for 14 days before imaging to ensure proper contrast diffusion in the brain for magnetic resonance imaging (MRI) scan. For non-MRI scan brains, after gross examination, brains were fixed with 4% paraformaldehyde (PFA) in 1×PBS buffer for 24 hours and then transferred into a 1×PBS+0.02% sodium azide for storage before processing for histology. For histology, brains were cut in a mouse brain matrix (Zivic Instruments, Pittsburgh, Pa.). Three (3) coronal cuts were made at −6 mm from bregma, middle line of cerebellum), then 4 mm anterior (−2 mm from bregma) and then 3 mm anterior to the second cut (+1 from bregma). Blocks were embedded in paraffin and 7 μm sections cut using a microtome.

Anti-β3 ICH model: For a subset of mice (n=16) intended for MRI, the whole head was severed from the neck and was immediately fixed with 4% paraformaldehyde (PFA) in 1×PBS buffer and 2 mM Gadoteridol contrast agent for 24 hours. Each brain was transferred into a 1×PBS+0.02% sodium azide and 2 mM Gadoteridol contrast agent. Heads were kept in this immersion solution for 14 days before imaging to ensure proper contrast diffusion in the brain. For non-MRI brains, after gross examination, brains were fixed with 4% paraformaldehyde (PFA) in 1×PBS buffer for 24 hours and then transferred into a 1×PBS+0.02% sodium azide for storage before processed for histology.

Hematoxylin and Eosin Staining

Brain blocks were processed and embedded in paraffin. Seven micron sections were cut using a microtome. Sections were deparaffinized in xylene and rehydrated through a decreasing gradient of ethanol solutions. Slides were stained with hematoxylin and eosin, coverslipped with xylene-based mounting medium (Permount, Sigma Chemical Company, St. Louis, Mo.) and viewed under a light microscope.

Fluoro-Jade Staining

Fluoro-jade B (Histo-Chem Inc., Jefferson, Ark.) was used to assess neuronal degeneration. Brain sections were deparaffinized and rehydrated. Following incubation with deionized water, the slides were incubated in 0.06% potassium permanganate (Sigma-Aldrich) for 15 minutes. Slides were then rinsed in deionized water and immersed for 30 minutes in 0.001% Fluoro-jade B working solution (0.1% acetic acid). Slides were washed and dried (60° C.) for 15 minutes, then cleared in xylene and coverslipped with a non-aqueous, low fluorescence, styrene based mounting media (DPX, Sigma-Aldrich). Slides were viewed under a fluorescent light microscope (Olympus BX50, Olympus, Richmond Hill, ON, Canada) and images were taken using constant parameters (exposure time and contrast values).

Gross Examination

For the integrin ICH model, brains were taken out of the skull, cut at the mid-coronal position and assessed in a binary manner for whether or not there was any evidence of ICH. Brains were immediately fixed following assessment. For the LPS model, brains were extracted after perfusion fixation, and images were taken for the whole brain to examine the appearance of microbleeding spots.

Contrast Enhanced Magnetic Resonance Imaging

Brains were scanned using 7T Burker MRI with 16-channel solenoid coils. Pulse sequence utilized was a FLASH T2* gradient echo (GRE) sequence with the following parameters: TR=30.2 ms and TE=12 ms. matrix=250×200×200. FOV=FOV=2.5×2.0×2.0 gcrush=6 tcrush=0.002. FA was 11°. (Liu S, Grigoryan M M, Vasilevko V et al. Comparative analysis of H&E and Prussian blue staining in a mouse model of cerebral microbleeds. J Histochem Cytochem 2014; 62:767-773). Voxel size was 100*100*100 μm. Following the reconstruction of images and applying image distortion correction algorithms, all brains were processed and analyzed for total volume of brain and total volume of hemorrhage. Quantification was done using percentage of bleeding (normalized to each brain size). Experimental blinding was done to ensure unbiased work at all levels of preparation and analysis. First, samples were prepared and coded not knowing which group they belong to. Secondly, a separate technician blinded to groups scanned the brains. Lastly, quantification was done in a blinded fashion. All quantifications and 3D reconstructions were performed using a combination of Display and Amira processing software.

Spectrophotometer Analysis of Hemoglobin Concentration

Drabkin's reagent (Sigma Aldrich) was used for calorimetric quantification of hemoglobin concentration at 540 nm. C57BL/6 mice were randomly assigned to three groups (each n=4): Control, Low-dose ARM, and High-dose ARM. For ARM groups, three days of 25 mg/kg/day and 100 mg/kg/day ARM were administered for low and high dose, respectively. Blood from saphenous vein were collected at day 4 and tested for hemoglobin concentration using UV 3600 Shimadzu spectrophotometer. A standard curve was generated using a known standard solution of cyanmethemoglobin, and blood concentrations of Hb was compared to the standard curve.

Data Analysis and Statistics

A-priori power analysis was done to estimate the number of samples in each group for a two-tailed, unpaired two-sample t-test with a power of 0.8 and α of 0.05 to detect a 1 standard deviation difference in bleeding volume. P values were determined by unpaired, two-tailed t-test with Welch correction, analysis of variance (ANOVA). All bar graphs and Dose-Response curves are expressed as mean±SEM or SD.

Chemicals

For all mouse model work, artemether (80 mg·ml-1) was obtained from Dafra Pharma and diluted 1:15 in fractionated coconut oil, and was administered intraperitoneally. For zebrafish work, artesunate were purchased from Guilin Pharmaceutical (Guangxi, China), together with artemether from Dafra are named GMP drugs. Both ART compounds were also purchased from Sigma Aldrich (Sigma) for comparison studies with GMP drugs.

Example 1

Zebrafish Screen to Identify Lead Compounds

Several models of ICH/BMH in zebrafish have been used, including statins, $bbh^{m292}$ and $rhd^{mi149}$ mutants and MOs to reduce expression of pak2a, βPix, Rap1b and cdh5. In addition, low doses of LPS were determined to induce ICH in zebrafish, consistent with the mouse BMH model. LPS destabilizes the vasculature and causes vascular leakage throughout the fish, including in the brain.

FIG. 1 shows the results of experiments conducted using an atorvastatin-induced intracerebral hemorrhage (ICH) model in zebrafish for chemical screening. Panel (A) is a schematic diagram showing the molecular pathway where statins act. Panels (B)-(G): ICH was induced by application of 1 μmol/atorvastatin at 2 hours post fertilization of embryos from adult wild type or Tg (flk-1:eGFP) and Tg (gata-1:DsRed) zebrafish, and arrayed into 96-well plates that contained the drug compounds. ICH phenotype rescue was measured. No extravasation of red blood cells was observed in vehicle DMSO treated control embryos (panels B, D and F). Atorvastatin treated embryos show hemorrhage in the brain (≈80% panels C and G), and increased junction between endothelial cells (panel E as compared to panel D). Panel H is a schematic showing the scheme of the screening process. Panels I to L show EC50 experiments for four compounds from the ART family, two of which were identified from the NCC library. Data is expressed as mean±SEM from 3-4 experiments. ARM, artemether; DHA, dihydro-artemisinin; ARS, artemisinin; ART, artesunate.

Screening of NCC libraries. The National Institutes of Health (NIH) Clinical Collections 1 and 2 consist of 727 compounds including many Food and Drug Administration-approved drugs for drug repurposing (www.nihclinicalcollection.com). These compounds are mostly drugs that have been in phase 1 to 3 clinical trials and are not represented on other arrayed collections. They have favorable properties such as purity, solubility and commercial availability. Many have known safety profiles.

After optimizing the brain hemorrhage model with 1 μmol/L atorvastatin, 727 compounds in NIH compound libraries 1 and 2 (http://nihsmr.evotec.com/evotec/sets/ncc) were screened using the conditions described (96 well plates with 7 embryos per well, and atorvastatin, 1 μmol/L). Six active compounds from four families (two dihydropyridine calcium channel blockers (benidipine and lacidipine), ethynylestradiol, triptolide, two anti-malaria drugs (artesunate and artemether)) were identified independently from the libraries. Chemical structure and properties of these six active compounds plus two of the derivatives of ART family compounds are summarized in Table 3 and FIGS. 1 and 2.

Figure 2:
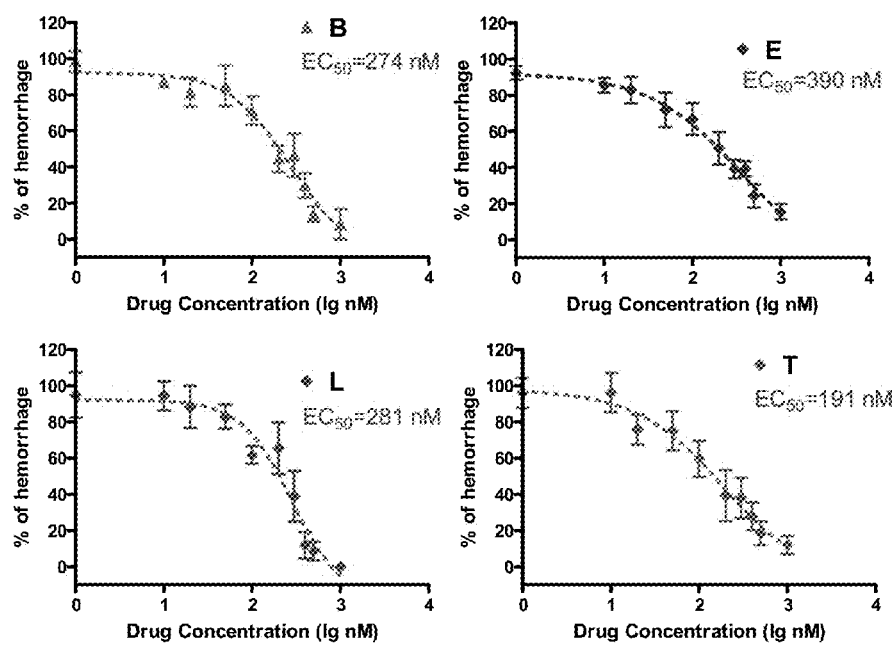
FIG. 2 shows inhibition of brain hemorrhage induced by 1 μM atorvastatin in zebrafish for four active compounds identified from NCC libraries. Plots are % hemorrhage (y axis) vs. drug concentration (lg nmol/L) (x-axis). EC50 is concentration of the drug at 50% of efficacy. Data is expressed as mean±SEM from 3 to 4 experiments. B is benidipine; E is ethynylestradiol; L is lacidipine, and T is triptolide.

FIG. 2 shows inhibition of brain hemorrhage induced by E 1 μmol/L atorvastatin in zebrafish by four active compounds identified from NCC libraries, where EC50 is the concentration of the drug at 50% of efficacy. Data is expressed as mean±SEM from 3 to 4 experiments. Data was normalized to that of vehicle-treated controls, and fitted with sigmoidal fit with variable slope in GraphPad Prism 4 software. B is benidipine; E is ethynylestradiol; L is lacidipine, and T is triptolide.

TABLE 3

| Name of Compound | Chemical Structure | Efficacy on atorvastatin Hemorrhage | Efficacy on β-Pix MO Hemorrhage | Property or Clinical Application | $EC_{50}$ (in nmol/L) on atorfvastatin model (μmol/L) |
| --- | --- | --- | --- | --- | --- |
| Artemisinin | [structure] | +++++ | +++++ | Anti-malaria | 95 |
| Dihydroartemisinin | [structure] | +++++ | +++++ | Anti-malaria | 67 |

TABLE 3-continued

| Name of Compound | Chemical Structure | Efficacy on atorvastatin Hemorrhage | Efficacy on β-Pix MO Hemorrhage | Property or Clinical Application | EC$_{50}$ (in nmol/L) on atorfvastatin model (μmol/L) |
|---|---|---|---|---|---|
| Artemether (NGP-104-6-F5) | 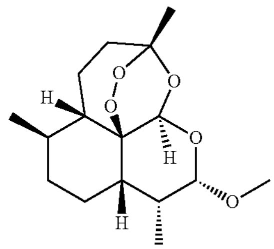 | +++++ | +++++ | Anti-malaria | 64 |
| Artesunate (NGP-104-2-E7) | 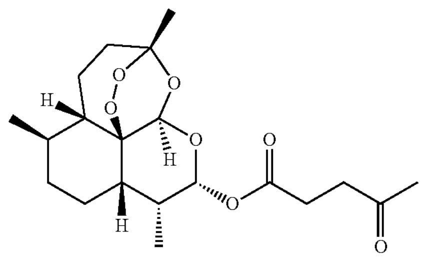 | +++++ | +++++ | Anti-malaria | 211 |
| Benidipine (NGP-104-30B7) | 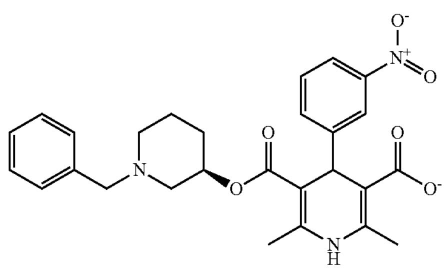 [SMILES: CC1=C(C(=O)[O-])C(c2cccc([N+](=O)[O-])c2)C(C(=O)O[C@@H]2CCCN(Cc3ccccc3)C2)=C(C)N1] | ++++ | ++++ | Hyper-tension | |
| Lacidipine (NGP-104-6-C2) | 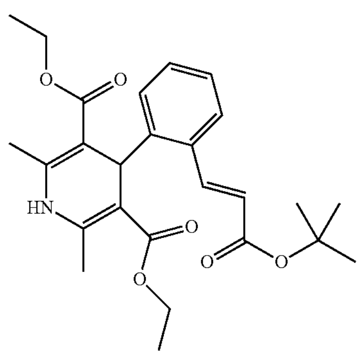 [SMILES: CCOC(=O)C1=C(C)NC(C)=C(C(=O)OCC)C1c1ccccc1/C=C/C(=O)OC(C)(C)C] | ++++ | Not tested | Hyper-tension | |
| Ethynylestradiol (NGP-104-1-E10) | 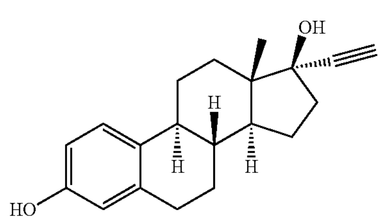 | +++ | Not tested | Contra-ceptive | |

TABLE 3-continued

| Name of Compound | Chemical Structure | Efficacy on atorvastatin Hemorrhage | Efficacy on β-Pix MO Hemorrhage | Property or Clinical Application | $EC_{50}$ (in nmol/L) on atorfvastatin model (μmol/L) |
|---|---|---|---|---|---|
| Tripolide (NGP-104-3-G7) | 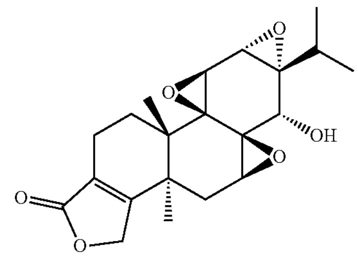 [SMILES: CC(C)[C@]12O[C@H]1[C@@H]1O[C@]13[C@]1(O[C@H]1C[C@@]1(C)C4=C(CC[C@]31C)C(=O)OC4)[C@H]2O] | ++++ | No effect | Not used in clinic; anti-cancer, immunosuppressive and anti-inflammatory | |

Active compounds identified from NIH clinical collections (NGP-104 library).
The ATV model was induced by 1 μmol/L atorvastatin.
One + sign represents 20% inhibition on 1 μmol/L ATV or β-Pix MO-induced hemorrhage.

Three of the four ART compounds showed high potency with EC50 less than 100 nmol/L. Due to the moderate potency of the other four compounds (EC50 ranging 191 to 290 nmol/L), we did not investigate them further.

Example 2

Studies on Mechanisms of Action of ART Compounds in Zebrafish

Figure 3:
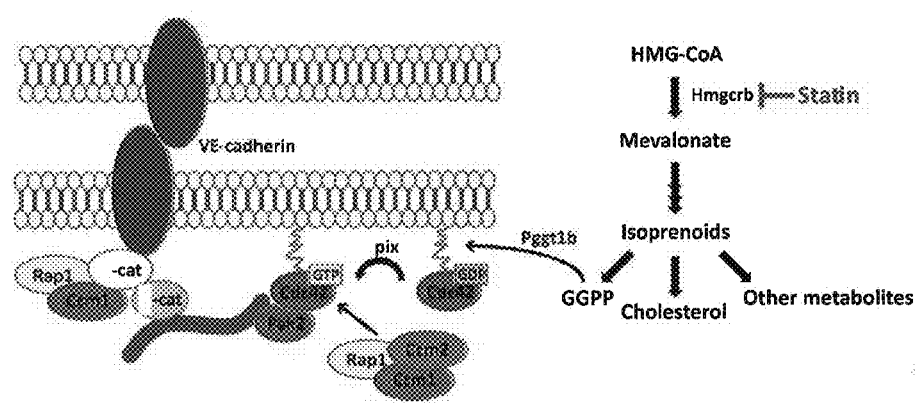
FIG. 3 shows the relationship between the HMGCR-mediated metabolic pathway, the Rho GTPase (Cdc42)-cadherin signaling pathway, and cerebral cavernous malformation (Ccm) pathways in zebrafish. By inhibiting HMG-CoA, statin treatment may lead to vascular instability and brain hemorrhage in zebrafish through the CDC42-cadherin pathway. ART family compounds are shown to be effective in rescuing brain hemorrhage caused by genetic knockdown of several key molecules of this pathway (e.g., pak2, βpix). This suggests that ART compounds act on a downstream target that is vital for vascular stability in the brain.

Clinical studies have disclosed a link between cholesterol-lowering 3-hydroxy-methylglutaryl-coenzyme A reductase (HMGCR) inhibitors (statins) and increased risk of ICH. The HMGCR pathway is connected to components of the Rho guanosine triphosphatase (GTPase) signaling pathway by prenylation of Cdc42/Rac (FIG. 3). Many proteins in this pathway are responsible for vascular stability. We hypothesized that some ICH/BMB are secondary to vascular instability that is mediated by impaired protein prenylation; and that any defect induced in the proteins (such as mutation or changes in expression) might cause hemorrhage. To address the pathways and proteins that are involved and to better understand the mechanism by which a drug rescues the hemorrhage, we decided to induce hemorrhage by genetic modification and to test whether it could be rescued by the ART drugs.

1. ART Compounds Rescued Bbh Genetic Model of Brain Hemorrhage.

A specific zebrafish line with a gene mutation called bubblehead (bbh) was used. This line has spontaneous ICH. Bubblehead phenotype is caused by a mutation in βPix. Adult homozygous zebrafish were viable and fertile. Bubblehead embryos develop ICH and brain edema 36 to 52 hours postfertilization (hpf) (Liu J, Zeng L, Kennedy R M, Gruenig N M, Childs S J. betaPix plays a dual role in cerebral vascular stability and angiogenesis, and interacts with integrin alphavbeta8. Dev Biol 2012; 363:95-105; Liu J, Fraser S D, Faloon P W et al. A betaPix Pak2a signaling pathway regulates cerebral vascular stability in zebrafish. Proc Natl Acad Sci USA 2007; 104:13990-13995). More than 85% of zebrafish larvae display an ICH phenotype. Interestingly, we found that treating with the ART drugs could completely rescue the hemorrhage in bbh mutants. FIG. 4 shows results from drug efficacy assays in the bbh model for two compounds, artesunate (ART), and artemether (ARM). Table 4 shows EC50 values measured for the various drugs.

TABLE 4

Comparison of efficacy (EC50 values) of different drugs to rescue brain hemorrhage in statin and bbh models. For the statin model, n = 15-20 larvae per condition; the experiment was performed three times per compound. For the bbh mutant model, n = 15-20 larvae per condition; the experiment was performed 1-3 times per compound.

| Drug | Statin Model (nmol/L) | bbh Mutant Model (nmol/L) |
|---|---|---|
| ART (GMP) | 182.2 | 126.9 |
| ART (Sigma) | 105.0 | 140.3 |
| ARM (Sigma) | 24.7 | 37.5 |
| ARS (Sigma) | 81.3 | 176.6 |
| DHA (Sigma) | 80.8 | 107.1 |

The obtained EC50 values of the ART drugs from the bbh mutant model and from the atorvastatin-induced ICH model were comparable. This confirms the validity of the statin model which was used for initial screening (Table 3).

2. ART Compounds Rescued ICH Induced by Gene Knockdown of Key Proteins in the HMBCR/Rho Kinase Pathway Besides using bbh, the other method to induce ICH in zebrafish is genetic gene knockdown. We used specific morpholinos to knock down some key genes in both HMGCR and Rho guanosine triphosphatase (GTPase) signaling pathways (FIG. 3). The morpholinos for the following genes were used:

1) Pak2a: p21 protein (Cdc42/Rac)-activated kinase 2a regulates activity of Rho GTPases, Rac and Cdc42, and may be involved in a complex with βPix.

2) βPix: Pak-interacting exchange factor α facilitates conversion of GDP-Rho GTPases (Rac and Cdc42) to GTP-RhoGTPase.

3) HMGCR: 3-hydroxy-3-methylglutaryl-coenzyme A reductase catalyzes conversion of HMG-Co A to mevalonate.

4) VE-Cadherin: Vascular Endothelial Cadherin is a transmembrane protein that connects the intracellular cytoskeleton to the extracellular matrix.

5) Rap1b: Ras GTPase effector protein facilitates recruiting of CCM proteins to the cell membrane.

6) GGTase 1: geranylgeranyltransferase 1 post-translationally modifies Rac and Cdc42 by adding a mevalonate-derived GGPP which is required to activate these GTPases.

FIG. 14 (A-B) shows that artesunate dose-dependently rescues hemorrhage phenotype induced by morpholinos targeting membrane stability of brain vessels in zebrafish. (A) Schematic diagram showing the target sites of the three morpholinos studied. (B) Artesunate dose-dependently rescues all three morpholinos-induced brain hemorrhage in zebrafish. (C-D) Artesunate rescues the ICH phenotype underlying the bbh$^{m292}$ mutation. (C) Upper panel, partial exon-intron organization of bPix gene showing the point mutation effecting splicing of the gene. Lower panel, RT-PCR analysis of wild-type and bbh$^{m292}$ mutant cDNA with primers flanking exon-14. (D) Upper panel, the phenotypes of bbh$^{m292}$ mutants treated with DMSO or artesunate and imaged at 48 hpf. The arrows denote sites of hemorrhage. Lower panel, percentages of bbh$^{m292}$ embryos with brain hemorrhage rescued by artesunate.

Artesunate dose-dependently reduced ICH/BMH after treatment with pak2a-MO (FIGS. 12 and 14). MO-mediated inhibition of hmgcrb, the zebrafish enzyme inhibited by statins, caused embryos to have ICH/BMH which also were prevented by artesunate (FIG. 14).

Finally, a role for the VE-cadherin homologue in zebrafish, cdh5, was demonstrated in that MO-knockdown of cdh5 induced ICH in zebrafish (FIG. 13). FIG. 13 shows the HMGCR molecular pathway that leads to vascular stability in zebrafish. Panels A & B: Stable EC junctions are maintained by a Cdc42-dependent and VE-cadherin-mediated cell-cell adhesion. VE cadherins are found on the surfaces of EC cell-cell junctions. VE-cadherins are associated with β- and α-catenins at their cytoplasmic domains, which connect them to the actin-based cytoskeleton (blue circles). Cdc42 belongs to the Rho-family of small guanosine triphosphatases (GTPases), which are the main regulators of VE-cadherin-based cell-cell adhesion. The functions of hmgcrb, βPix, and pak2a in regulating junctional stability in zebrafish are shown. HNGCR mediated GGPP biosynthesis regulates Cdc42 prenylation. βPix is a GEF that increases CDC42 affinity for GTP. Pak2 is an effector of Cdc42, which regulates actin filament organization. Panel C shows that splice-inducing morpholinos designed against cdh5, the zebrafish ortholog of the VE-cadherin gene, induced intracerebral hemorrhage in zebrafish at 36-48 hpf (lateral images are shown).

We found that injection of any of the above morpholinos causes hemorrhage in 3 dpf zebrafish larvae indicating the important roles these genes play in vascular stability. Next, optimum amount of each morpholino was determined. The goal was to induce an acceptable percentage of hemorrhage (ideally between 40-80%), without having toxicity from morpholino injection. The results are summarized in Table 5.

TABLE 5

Optimizing the amount of injected morpholinos, n = 150-250 larvae per condition; the experiment was performed at least two times.

| Morpholino | Optimum amount (ng) | Hemorrhage |
| --- | --- | --- |
| βPix - exon6 | 0.8 | 72.1% |
| Pak2a - exon8 | 5.0 | 43.7% |
| Hmgcrb - splice | 2.0 | 67.9% |
| Cdh5 - exon2 | 1.0 | 39.4% |
|  |  | 35.0% (Cardiac Edema) |
| Rap1b - exon3 | 9.0 | 30.8% (Faint) |
| GGTase1 | 2.5 | 11.4% (Faint) |

The first three morpholino pairs were good for the efficacy study. Efficacy assays were performed using Artemether (ARM, Sigma) and artemesunate (ART, GMP). The results showed that defects induced by Pak2a, βPix, and HMGCR morpholinos could induce hemorrhage in independent experiments. Treating these morphants with the drugs rescued the ICH phenotype. FIG. 5 shows an example of a drug efficacy study on hmgcrb morphants using artesunate (ART), and artemether (ARM); n=15-20 larvae per condition; the experiment was performed two times per compound. EC50 values calculated for the first three aforementioned morphants are shown in Table 6.

TABLE 6

Efficacy comparison (EC50) of ARM (Sigma) and ART (GMP) to rescue the hemorrhage induced by different morpholinos; n = 150-250 larvae per condition, and the experiment was performed at least two times.

| Morpholino | ARM (Sigma) (nmol/L) | ART (GMP) (nmol/L) |
| --- | --- | --- |
| βPix - exon6 | 51.6 ± 11.7 | 95.6 ± 27.9 |
| Pak2a - exon8 | 39.1 ± 8.0 | 169.2 ± 39.5 |
| Hmgcrb - splice | 62.5 ± 8.3 | 166.7 ± 9.3 |
| Cdh5 - exon2 | Rescue effect | Rescue effect |

Suppression of VE-cadherin induces hemorrhage. However, cardiac edema was observed in some morphants. The efficacy assays were performed using ARM and ART, and in both cases rescue was observed.

Consistent with what we found in the atorvastatin-induced ICH model and bbh mutant model, ARM showed the highest efficacy to rescue the hemorrhage in morphants (Table 4 and Table 6).

Studies on Toxicity of ART Compounds in Zebrafish

Figure 7:
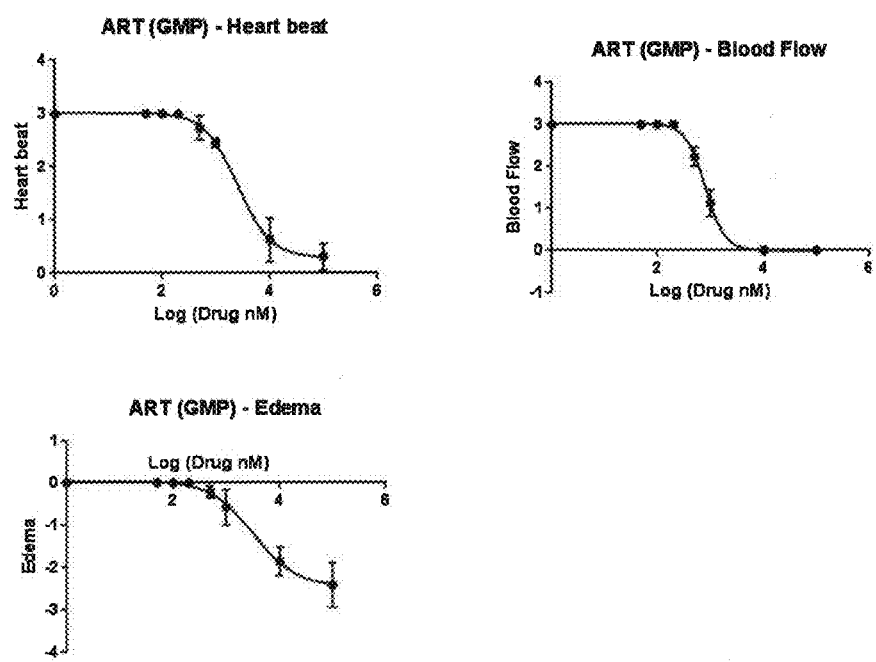
FIG. 7 shows the results of toxicity assays for artesunate (ART (GMP)) on heart beat, blood flow and heart edema. Heart beat and blood flow were ranked from 3 (normal heart beat or blood flow) to 0 (no heart beat or blood flow). Cardiac edema was ranked from 0 (normal heart without edema) to −3 (severe cardiac edema). TC50 is the concentration of the drug at 50% of maximum toxicity. Data is expressed as mean±SEM from 3 experiments.

Toxicity assays were performed to measure TC50 values considering three parameters: heartbeat, blood flow and cardiac edema As an example, FIG. 7 shows the results of toxicity assays for ART (GMP). Heart beat and blood flow were ranked from 3 (normal heart beat or blood flow) to 0 (no heart beat or blood flow). Cardiac edema was ranked from 0 (normal heart without edema) to −3 (severe cardiac edema). TC50 is the concentration of the drug at 50% of maximum toxicity. Data is expressed as mean±SEM from 3 experiments. TC50 values for all drugs as well as the TC50/EC50 ratio are summarized in Table 7.

TABLE 7

Comparison of toxicity (TC50 values) of different drugs. TC50/EC50 ratio is in parenthesis; n = 15-20 larvae per condition, and the experiment was performed three times per compound.

| Drug | Company | TC50 (Heart beat) [nmol/L] | TC50 (Blood flow) [nmol/L] | TC50 (Edema) [nmol/L] |
| --- | --- | --- | --- | --- |
| Artemisinin (ARS) | Sigma | 8501 (104.5) | 1058 (13) | 34134 (419) |
| Artesunate (ART) | Sigma | 8884 (84.6) | 741.5 (7.1) | 5367 (51.1) |
| Artemether (ARM) | Sigma | 2328 (94.3) | 975.3 (39.5) | 19564 (87.1) |
| Dihydroartemisinin (DHA) | Sigma | 5.011e+0.11 (6.2e+009) | 890 (11.0) | 748.5 (9..2) |
| Artemisinin (ARS) | Sequoia Rsearch (UK) | 1.217e+010 4.6e+007) | 5340 (20.4) | 6347 24.2) |
| Artesunate (ART) | Sequoia Research (UK) | 9539 (59.5) | 1036 (6.5) | 937.8 (5.9) |
| Artemether (ARM) | Sequoia Research (UK) | 1.084e+013 (1.3e+011) | 746.3 (9.2) | 5.253e+012 (6.5e+010) |
| Dihydroartemisinin (DHA) | Sequoia Research (UK) | 1.110e+008 (8.3e+005) | 979.5 (7.3) | 1021 (7.6) |
| Artesunate (ART) | GMP-Artesunate | 2525 (13.9) | 794.4 (4.4) | 3196 (17.5) |
| ZA102 | Life Chemicals | 376 (2.1) | 695.3 (3.8) | 24444 (135) |
| ZA113 | Life Chemicals | 2283 (17.3) | 572.3 (4.3) | 5883 (44.5) |
| ZA123 | Life Chemicals | 6.491e+007 (5.2e+005) | 989.3 (7.9) | 55912 (445.5) |

We found ARM to be a safe drug, as its EC50 is much lower than TC50 (Table 7) in zebrafish embryos.

3) ART Compounds Upregulate Key Proteins Vital for Vascular Stability

We considered a list of 20 genes that are potentially involved in ICH mechanism, and evaluated the changes in transcription of five of them after in atorvastatin-induced brain hemorrhage model and treated with ART drugs. These genes are: VE-Cadherin (Cdh5), Integrin (Itgb3a) and three cerebral cavernous malformation genes (ccm1, ccm2 and ccm3).

Figure 6:
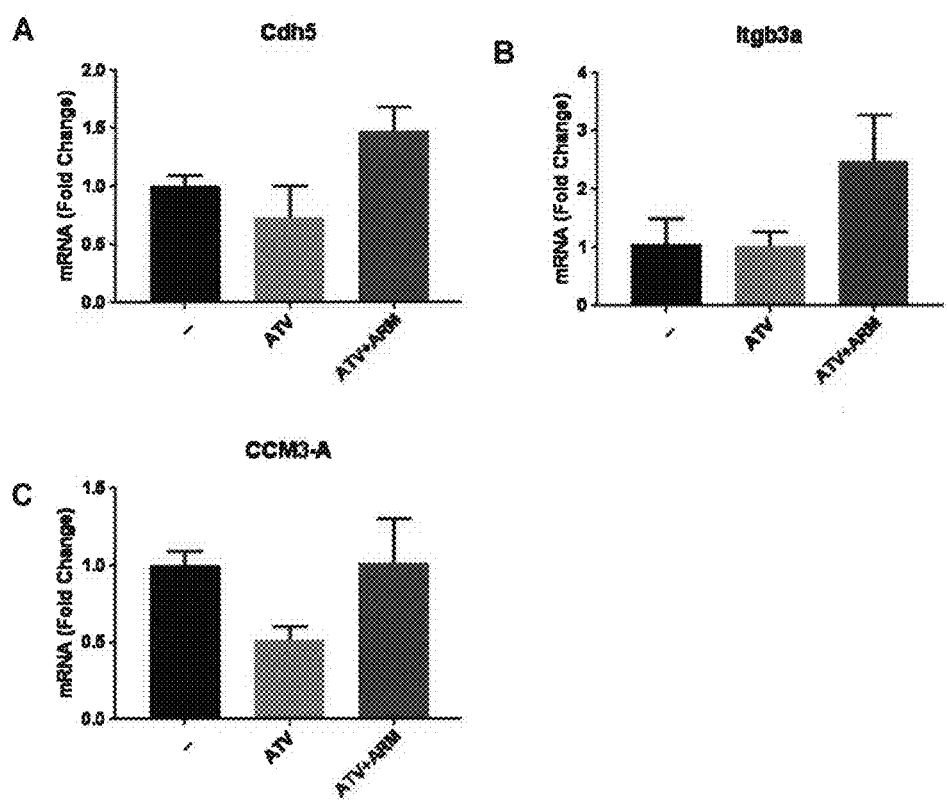
FIG. 6 shows mRNA changes upon treatment with atorvastatin (ATV) and with atorvastatin plus artemether (ATV+ARM). qRT-PCR analysis was used to evaluate the mRNA level of gene expression of VE-cadherin (panel A), β3-integrin (panel B), and CCM3 (Panel C), in zebrafish treated with 1 μM atorvastatin (ATV), with ATV plus 500 nmol/L of artemether (ARM) as shown, n=3.

FIG. 6 shows the changes in gene transcription upon adding statin (ATV) and artemether (ARM) at 500 nmol/L. qRT-PCR analysis was used to evaluate the mRNA level of gene expression of A, VE-Cadherin; B, 33-Integrin, C CCM3, in zebrafish treated with 1 μmol/L atorvastatin (ATV) and 500 nmol/L of Artemether (ARM), n=3. At this concentration, no hemorrhage was observed. Each figure shows the experiment results of 50-60 of 3 dpf embryos.

The results showed that in the statin-induced ICH model, upregulation at the transcription level occurs for Integrin β3 and VE-cadherin upon treatment with ARM. CCM3 showed a decrease after inducing hemorrhage with atorvastatin. Upon treatment with ARM, the transcription level returned to normal in parallel with hemorrhage rescue in zebrafish larvae.

Example 3

Other Zebrafish Models to Validate Anti-ICH Efficacy of Compounds Identified from Statin-derived Embryonic Screens Experiment 1: LPS-induced ICH/BMH in zebrafish embryos. The lead compounds will be tested in a LPS model of ICH/BMH to determine if rescue of the ICH/BMH phenotype is a general property of these compounds or it is specific to statin-induced ICH/BMH. Preliminary data suggested that artemether reduced mortality from LPS (FIG. 15). FIG. 15 shows that LPS induces brain hemorrhage in developing zebrafish embryo and artemether have protective effects on LPS-induced mortality. Panel A shows survival curves of developing zebrafish embryos when LPS is delivered in fish water at 24 hours post fertilization (hpf). Panel B shows that 1 μmol/L artemether in fish water had a protective effect on fish survival. LPS concentration used was 200 mg/mL. Panel C shows that 25 mg/mL LPS treatment of 24 hpf embryos resulted in no mortality but 52% of embryos (n=120) had brain hemorrhage. Experiments are ongoing to define the rescuing effects of artemether on LPS-induced brain hemorrhage. Double transgenic zebrafish (Gata1:DsRed/Flk1:GFP) with green fluorescent vessel and red fluorescent red blood cells are used. Arrow points to hemorrhage.

Example 4

Work in Mouse Models of ICH

We employed two models of brain hemorrhage. Our results show that in both LPS and Integrin models of ICH, ARM effectively prevented or ameliorated hemorrhage.

LPS-induced Microbleeding Mouse Model

1. ARM (GMP) Reduces Both Surface and Deep Brain Microbleeds Induced by LPS

LPS and its main receptor TLR4 have been extensively studied, and recent literature characterized a model of brain micro-bleeds that are both present on the surface cortical areas and in the deep lobar areas (Liu S, Grigoryan M M, Vasilevko V et al. Comparative analysis of H&E and Prussian blue staining in a mouse model of cerebral microbleeds. J Histochem Cytochem 2014; 62:767-773; Sumbria R K, Grigoryan M M, Vasilevko V et al. A murine model of inflammation-induced cerebral microbleeds. J Neuroinflammation 2016; 13:218). The number of surface micro-bleeds of each brain was counted using a stereomicroscope, and an average determined for LPS control and LPS+ARM treatment groups. FIG. 8 shows that artemether (ARM) rescues LPS-induced brain microbleeds in mice. Panel A shows data from a stereomicroscope count of surface microbleeds in brains from LPS treated mice (n=8) or LPS+ artemether-treated mice (n=8). The left panel shows representative images from each of the two groups; arrows indicate microbleeds. The right panel shows a statistical analysis (*P<0.05, two-tailed t-test with Welch correction); data is expressed as mean±SD. As compared to LPS treated animals, brains from ARM treated mice showed a robust reduction in total surface microbleeds.

To further assess microbeeding inside the brains, we quantified the numbers of microbleeds in H&E stained brain slides. Panel B shows data from quantification of microbleeds on brain slices stained by hematoxylin and eosin. The left panel shows representative images of stained brain slices with microbleeds from each of the two groups; the arrows indicate microbleeds on the slices; the right panel chart shows a statistical analysis on microbleeds count (**P<0.01, unpaired two-tailed t-test with Welch's correction. Data is expressed as mean±SD, n=8 for both LPS treated and LPS+ARM treated groups.

Similar to the surface microbleed counts, ARM treatment significantly reduced the total number of microbleeds inside the mouse brains (FIG. 8B).

Figure 9:
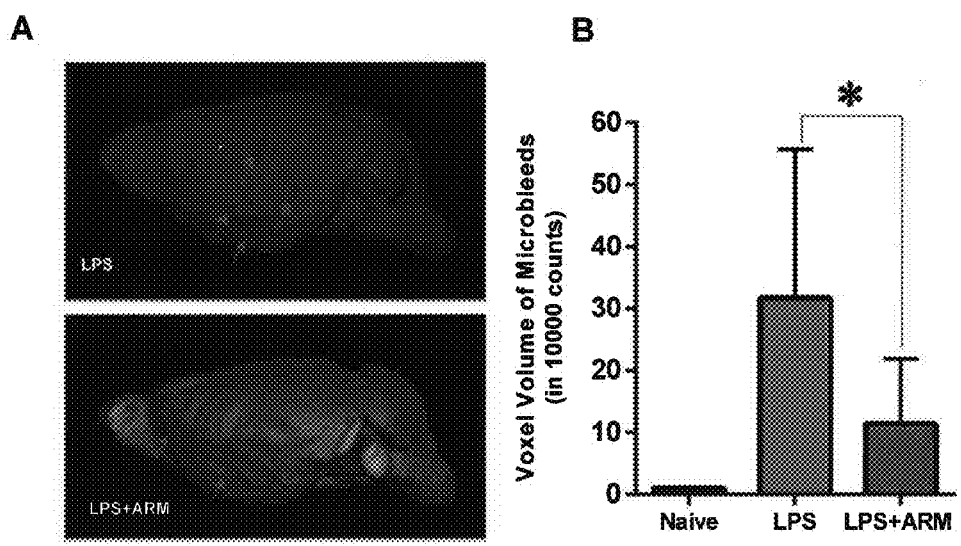
FIG. 9 shows that artemether (ARM) rescues microbleeding induced by lypopolysaccharide (LPS) in mice. Panel (A) shows representative 3-D reconstructed images from T2*—Weighted Gradient Echo (GRE) MRI sequence with high resolution detection, in mouse cerebral cortex two days after LPS injection or in LPS+ARM treated brains. Arrows indicate microbleeds. (B) is a bar graph showing the number of microbleedings per brain in a vehicle control group and a group treated with artemether (ARM). Quantification of total microbleed volume was calculated using semi-automated software (Display), normalized to total brain volume, and expressed as total voxel in 10000 counts. Data is expressed as mean±SD (*P<0.05, two-tailed t-test with Welch correction); n=8 for both LPS treated and LPS+ARM treated groups, 2 for naïve controls.

2. The Reduction of Total LPS-induced Microbleeds in Mouse Brains by ARM (GMP) is Verified by MRI To confirm the result from gross anatomy and histology, we examined the brains in the subsequent experiments using a MRI with 3D FLASH GRE sequence. Total volume of hemorrhage was quantified and percent bleeding was calculated for each brain. FIG. 9 shows that artemether (ARM) rescues microbleeding induced by lypopolysaccharide (LPS) in mice. Panel A shows representative 3D reconstructed images from T2*—Weighted Gradient Echo (GRE) MRI sequence with high resolution detection, showing microbleeds from LPS or LPS+ARM treated mouse brains. Arrows indicate the microbleeds. Panel B is a bar graph showing the number of microbleedings per brtain in a vehicle control group and a group treated with artemether (ARM). Quantification of total microbleeds volume was calculated using semi-automated software (Display), normalized to total brain volume, and expressed as total voxel in 10000 counts. Data is expressed as mean±SD (+P<0.05, two-tailed t-test with Welch correction), n=8 for both LPS treated and LPS+ARM treated groups, 2 for naïve controls.

The data confirm that there is a significant reduction of bleeding (about ⅔ reduction) in the ARM treated group in comparison to the model control group (FIG. 9).

3. LPS Did not Induce Significant Neuronal Cell Death or Hemosiderin Deposition

We did Fluoro-jade C and Perl's staining to detect neuronal degeneration and hemosiderin deposition, respectively. The results of both of these assays were negative for both control and treatment groups, suggesting that the observed micro-bleeds induced by LPS are acute and that the microbleeds did not cause neuronal cell death, at least in the time scale we tested on this model.

Integrin ICH Mouse Model

1. ARM (GMP) Reduces the Incidence Rate of ICH

Previous studies suggested that by forming a heterodimer with the αV subunit of integrin, β3 integrin plays a role in proliferating endothelial cells, specifically during angiogenesis (Yougbare I, Lang S, Yang H et al. Maternal anti-platelet beta3 integrins impair angiogenesis and cause intracranial hemorrhage. J Clin Invest 2015; 125:1545-1556). It has already been shown that using antibodies especially during the developmental stage creates vascular instability and improper angiogenesis and hence rapid ICH development. Id.

Figure 10:
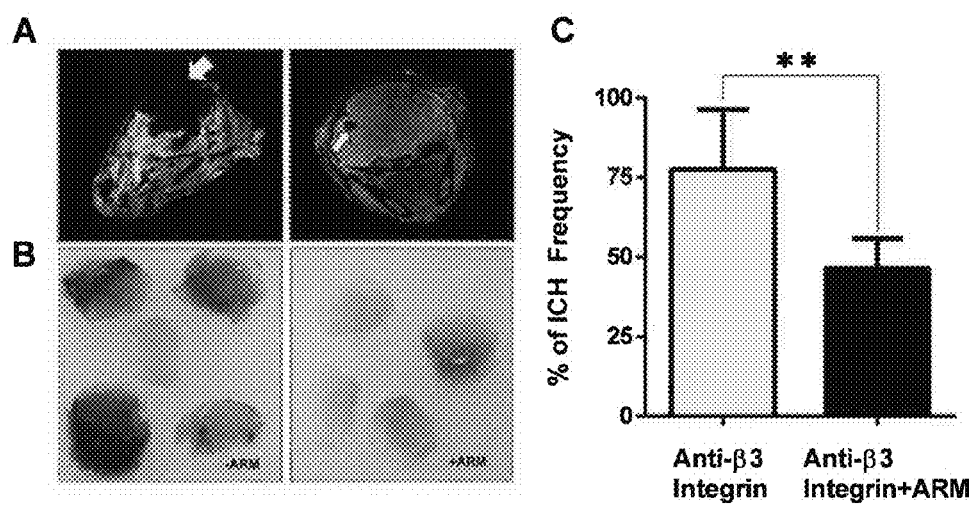
FIG. 10 shows that artemether (ARM) reduces ICH in an anti-β3 integrin mouse model of intracerebral hemorrhage. Panel A shows representative raw T2*—Weighted Gradient Echo (GRE) MRI images of brains of mice injected with anti-β3 integrin serum at post-natal day 2 alone (left) or treated with ARM (right). Panel B shows paraffin-embedded blocks of coronally-cut whole brains from anti-β3 serum injected mice without (left) or with (right) ARM treatment, respectively. Panel C shows quantification of frequency of intracerebral hemorrhage in mice injected with anti-β3 integrin serum alone or with ARM treatment. Data is expressed as mean±SD (**P<0.01, two-tailed t-test with Welch correction); n=29 and 24 for anti-β3 integrin serum injected mice without or with ARM treatment, respectively.

We employed two end points to examine the treatment effect of ARM in the anti-β3 integrin model of intracerebral hemorrhage. FIG. 10 shows that artemether (ARM) reduces ICH in an anti-β3 integrin mouse model of intracerebral hemorrhage. Panel A shows representative raw T2*—Weighted Gradient Echo (GRE) MRI images of brains of mice injected with anti-β3 integrin serum at post-natal day 2 alone (left) or treated with ARM (right). Panel B shows paraffin-embedded blocks of coronally-cut whole brains from anti-β3 serum injected mice without (left) or with (right) ARM treatment, respectively. Panel C shows quantification of frequency of intracerebral hemorrhage in mice injected with anti-β3 integrin serum alone or with ARM treatment. 77% of neonates showed ICH in the ICH model control group. In comparison, ARM reduced ICH incidence to 47%. Data is expressed as mean±SD (**P<0.01, two-tailed t-test with Welch correction), n=29 and 24 for anti-fβ3 integrin serum injected mice without or with ARM treatment, respectively.

2. ARM (GMP) Reduces the Total Volume of ICH Verified by MRI

Preliminary data shows that ARM reduced total volume of ICH as compared to controls. (data not shown).

To assess possible anemia effect from ARM treatment as some previous studies speculated, blood samples were tested for hemoglobin concentration after ARM treatment. Blood hemoglobin concentration was assessed using Drabkins' method. Spectrophotometer data was compared to a standard curve from standard cyanmethemoglobin concentrations. The control group received no drug. The Treatment Dose group received 3 days injection of low dose ARM (25 mg/kg), 4× Treatment Dose group received 3 days injection of high dose ARM (100 mg/kg).

Figure 11:
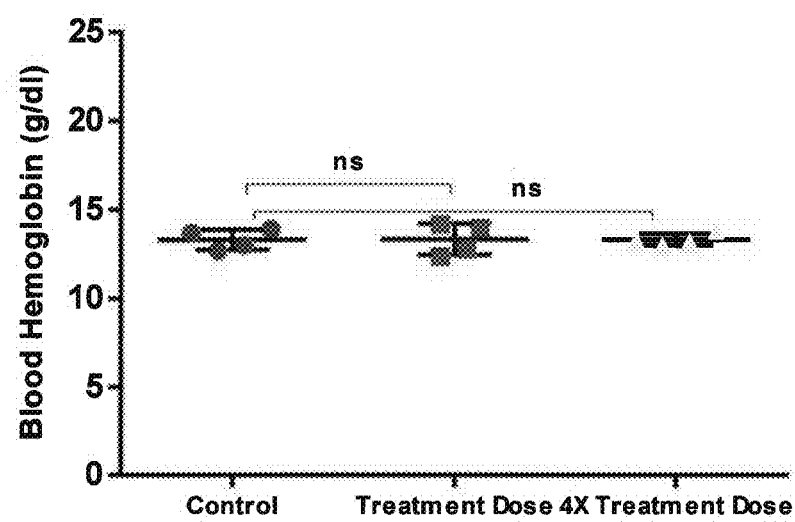
FIG. 11 shows a plot of blood hemoglobin (g/dl) (y-axis) for controls, and for mice treated with artemether (ARM) (Treatment Dose, and 4× Treatment Dose). ARM treatment for 3 days did not cause anemia in mice. Bloods were tested for hemoglobin concentration after ARM treatment. Blood hemoglobin concentration was assessed using Drabkins' method. Spectrophotometer data was compared to a standard curve from standard cyanmethemoglobin concentrations. The control group received no drug. The Treatment Dose group received 3 days injection of low dose ARM (25 mg/kg); 4× Treatment Dose group received 3 days injection of high dose ARM (100 mg/kg). Data is expressed as mean±SD (nsP>0.05, one-way ANOVA, n=4).

FIG. 11 shows that ARM treatment for 3 days did not cause anemia in mice. It is a plot of blood hemoglobin (g/dl) (y-axis) for controls, and for mice treated with artemether (ARM) (Treatment Dose, and 4× Treatment Dose). Bloods were tested for hemoglobin concentration after ARM treatment. Blood hemoglobin concentration was assessed using Drabkins' method. Spectrophotometer data was compared to a standard curve from standard cyanmethemoglobin concentrations. The control group received no drug. The Treatment Dose group received 3 days injection of low dose ARM (25 mg/kg); 4× Treatment Dose group received 3 days injection of high dose ARM (100 mg/kg). Data is expressed as mean±SD (nsP>0.05, one-way ANOVA, n=4). We did not find any statistical difference between the groups (FIG. 11).

Figure 16:
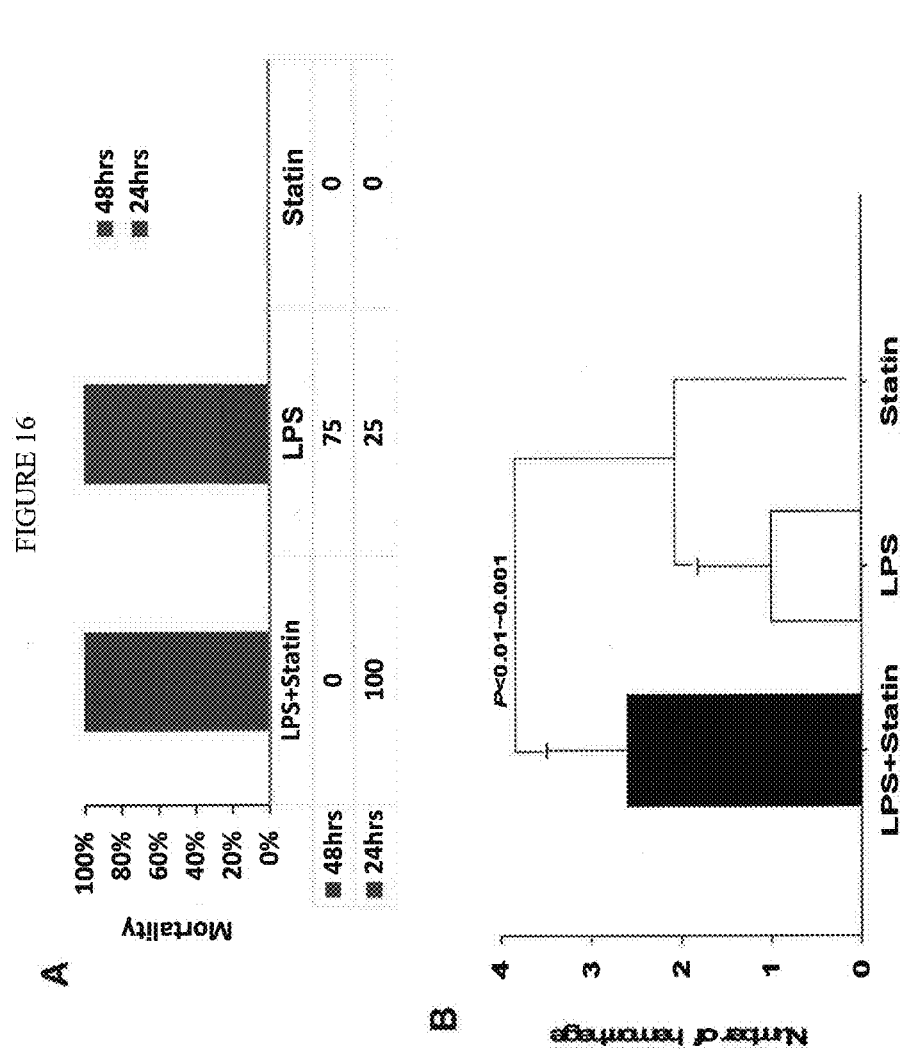
FIG. 16 shows that statin exacerbates LPS-induced intracerebral hemorrhage in mice. (A) Atorvastatin (50 mg/kg) treatment in addition to LPS (5 mg/kg), resulted in 100% mortality 24 hours after the treatments, while LPS treatment alone only result in 25% mortality at the same time examined, and statin alone did not cause any mortality (n=5). (B) Atorvastatin treatment significantly increased the number of large hemorrhages caused by LPS.

FIG. 16 shows that statin exacerbates LPS-induced intracerebral hemorrhage in mice. (A) Atorvastatin (50 mg/kg) treatment in addition to LPS (5 mg/kg), resulted in 100% mortality 24 hours after the treatments, while LPS treatment alone only result in 25% mortality at the same time examined, and statin alone did not cause any mortality (n=5). (B) Atorvastatin treatment significantly increased the number of large hemorrhages caused by LPS. While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for reducing incidence of brain vascular leakage comprising administering to a subject in need thereof a pharmaceutical composition containing a small molecule therapeutic compound selected from artemether or a derivative of artemether, a therapeutic amount of which is effective to reduce incidence of bleeding in the brain by at least 30% relative to a control wherein the brain vascular leakage is brain microhemorrhage induced by administration of a statin, or the brain vascular leakage is a spontaneous intracerebral hemorrhage.

2. The method according to claim 1, wherein the derivative of artemether is dihydroartemisinin, artemisinin, or artesunate.

3. The method according to claim 1, wherein the vascular leakage is brain microhemorrhage induced by administration of a statin.

4. The method according to claim 3, wherein the statin is atorvastatin.

5. The method according to claim 1, wherein the vascular leakage is a spontaneous intracerebral hemorrhage.

6. The method according to claim 5, wherein the spontaneous intracerebral hemorrhage occurs in association with a mutation of one or more genes selected from beta-pix, Pak2a, cdh5, ccm1, ccm2, ccm3, Rap1b, Pggt1b, Hmgcrb, and integrin beta3.

7. The method according to claim 1, wherein the spontaneous intracerebral hemorrhage is due to brain vascular malformation a brain vascular malformation.

8. The method according to claim 7, wherein the brain vascular malformation is a cerebral cavernous malformation.

* * * * *

UNITED STATES PATENT AND TRADEMARK OFFICE
CERTIFICATE OF CORRECTION

PATENT NO. : 10,292,991 B2  
APPLICATION NO. : 15/667423  
DATED : May 21, 2019  
INVENTOR(S) : Xiao-Yan Wen et al.

Page 1 of 1

It is certified that error appears in the above-identified patent and that said Letters Patent is hereby corrected as shown below:

On the Title Page

Item (73) under Assignee, replace Assignee listed as "UNITY HEALTH TORONTO (Toronto, CA)" with -- ZebraPeutics Inc. (Toronto, CA) --.

Signed and Sealed this  
Fifteenth Day of September, 2020

Andrei Iancu  
*Director of the United States Patent and Trademark Office*

SEQUENCE LISTING

<160> NUMBER OF SEQ ID NOS: 17

<210> SEQ ID NO 1
<211> LENGTH: 25
<212> TYPE: DNA
<213> ORGANISM: Artificial Sequence
<220> FEATURE:
<223> OTHER INFORMATION: Synthetic sequence

<400> SEQUENCE: 1
aaatgatgca gaacttgcct ttctg                                              25

<210> SEQ ID NO 2
<211> LENGTH: 25
<212> TYPE: DNA
<213> ORGANISM: Artificial Sequence
<220> FEATURE:
<223> OTHER INFORMATION: Synthetic sequence

<400> SEQUENCE: 2
tacaagaccg tctacctttc caatc                                              25

<210> SEQ ID NO 3
<211> LENGTH: 25
<212> TYPE: DNA
<213> ORGANISM: Artificial Sequence
<220> FEATURE:
<223> OTHER INFORMATION: Synthetic sequence

<400> SEQUENCE: 3
gcgcatctct cttaccacat tatag                                              25

<210> SEQ ID NO 4
<211> LENGTH: 25
<212> TYPE: DNA
<213> ORGANISM: Artificial Sequence
<220> FEATURE:
<223> OTHER INFORMATION: Synthetic sequence

<400> SEQUENCE: 4
aatagagtac aacatacctc ttggc                                              25

<210> SEQ ID NO 5
<211> LENGTH: 25
<212> TYPE: DNA
<213> ORGANISM: Artificial Sequence
<220> FEATURE:
<223> OTHER INFORMATION: Synthetic sequence

<400> SEQUENCE: 5
aactgcattc ataaactcac ccagt                                              25

<210> SEQ ID NO 6
<211> LENGTH: 25
<212> TYPE: DNA
<213> ORGANISM: Artificial Sequence
<220> FEATURE:
<223> OTHER INFORMATION: Synthetic sequence

<400> SEQUENCE: 6
cacgcggtgt gtggactcac ggtca                                              25

<210> SEQ ID NO 7
<211> LENGTH: 25
<212> TYPE: DNA
<213> ORGANISM: Artificial Sequence -continued

```
<220> FEATURE:
<223> OTHER INFORMATION: Synthetic sequence

<400> SEQUENCE: 7
cctcttacct cagttacaat ttata                                            25

<210> SEQ ID NO 8
<211> LENGTH: 20
<212> TYPE: DNA
<213> ORGANISM: Artificial Sequence
<220> FEATURE:
<223> OTHER INFORMATION: Synthetic sequence

<400> SEQUENCE: 8
acgatgtctc catcctgtct                                                  20

<210> SEQ ID NO 9
<211> LENGTH: 20
<212> TYPE: DNA
<213> ORGANISM: Artificial Sequence
<220> FEATURE:
<223> OTHER INFORMATION: Synthetic sequence

<400> SEQUENCE: 9
tagtgattcg gttccctcat                                                  20

<210> SEQ ID NO 10
<211> LENGTH: 20
<212> TYPE: DNA
<213> ORGANISM: Artificial Sequence
<220> FEATURE:
<223> OTHER INFORMATION: Synthetic sequence

<400> SEQUENCE: 10
tcacgctatt cctgctctgt                                                  20

<210> SEQ ID NO 11
<211> LENGTH: 20
<212> TYPE: DNA
<213> ORGANISM: Artificial Sequence
<220> FEATURE:
<223> OTHER INFORMATION: Synthetic sequence

<400> SEQUENCE: 11
actgcagatc tgagccgtac                                                  20

<210> SEQ ID NO 12
<211> LENGTH: 20
<212> TYPE: DNA
<213> ORGANISM: Artificial Sequence
<220> FEATURE:
<223> OTHER INFORMATION: Synthetic sequence

<400> SEQUENCE: 12
ggacagccag cattttgaga                                                  20

<210> SEQ ID NO 13
<211> LENGTH: 20
<212> TYPE: DNA
<213> ORGANISM: Artificial Sequence
<220> FEATURE:
<223> OTHER INFORMATION: Synthetic sequence

<400> SEQUENCE: 13
gtctgaaatc atgcggtccc                                                  20
```

```
<210> SEQ ID NO 14
<211> LENGTH: 19
<212> TYPE: DNA
<213> ORGANISM: Artificial Sequence
<220> FEATURE:
<223> OTHER INFORMATION: Synthetic sequence

<400> SEQUENCE: 14
catgattgac aggcccgag                                                  19

<210> SEQ ID NO 15
<211> LENGTH: 20
<212> TYPE: DNA
<213> ORGANISM: Artificial Sequence
<220> FEATURE:
<223> OTHER INFORMATION: Synthetic sequence

<400> SEQUENCE: 15
tgattgtctg caggaatcgg                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic sequence

<400> SEQUENCE: 16
cacattcaca gaacggaccc                                                 20

<210> SEQ ID NO 17
<211> LENGTH: 20
<212> TYPE: DNA
<213> ORGANISM: Artificial Sequence
<220> FEATURE:
<223> OTHER INFORMATION: Synthetic sequence

<400> SEQUENCE: 17
cacattcaca gaacggaccc                                                 20
```